United States Patent [19]

Selnick et al.

[11] Patent Number: 5,717,100

[45] Date of Patent: Feb. 10, 1998

[54] SUBSTITUTED IMIDAZOLES HAVING ANTI-CANCER AND CYTOKINE INHIBITORY ACTIVITY

[75] Inventors: Harold G. Selnick, Ambler; David A. Claremon, Maple Glen; Nigel J. Liverton, Harleysville, all of Pa.

[73] Assignee: Merck & Co., Inc., Rahway, N.J.

[21] Appl. No.: 717,955

[22] Filed: Sep. 23, 1996

Related U.S. Application Data

[60] Provisional application No. 60/005,063, Oct. 6, 1995, and provisional application No. 60/005,059, Oct. 6, 1995.

[51] Int. Cl.$^6$ .................. C07D 211/06; A61K 31/445
[52] U.S. Cl. ........................ 546/194; 514/318
[58] Field of Search ..................... 546/194; 514/318

[56] References Cited

U.S. PATENT DOCUMENTS

| | | | |
|---|---|---|---|
| 3,707,475 | 12/1972 | Lombardino et al. | 260/309 |
| 3,772,441 | 11/1973 | Lombardino et al. | 424/273 |
| 3,929,807 | 12/1975 | Fitzi | 260/298.4 R |
| 3,940,486 | 2/1976 | Fitzi | 424/263 |

FOREIGN PATENT DOCUMENTS

| | | |
|---|---|---|
| WO93/14081 | 7/1993 | WIPO |
| WO93/14082 | 7/1993 | WIPO |
| WO93/23381 | 11/1993 | WIPO |
| WO95/00501 | 1/1995 | WIPO |
| WO95/02591 | 1/1995 | WIPO |
| WO 95/03297 | 2/1995 | WIPO |
| WO96/03387 | 2/1996 | WIPO |

*Primary Examiner*—C. Warren Ivy
*Assistant Examiner*—Charanjit S. Aulakh
*Attorney, Agent, or Firm*—Richard C. Billups; Mark R. Daniel

[57] ABSTRACT

Compounds represented by formula I:

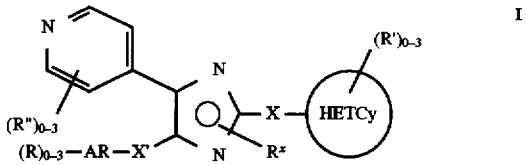

are disclosed. AR represents an aromatic group containing 6–10 atoms; and

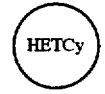

represents a 4 to 6 membered non-aromatic heterocycle containing only one N atom.

A pharmaceutical composition is also included.

Methods of treating cancer and cytokine mediated diseases are also included.

33 Claims, No Drawings

SUBSTITUTED IMIDAZOLES HAVING ANTI-CANCER AND CYTOKINE INHIBITORY ACTIVITY

This application claims priority of provisional application Ser. Nos. 60/005,063 and 60/005,059 filed on Oct. 6, 1995.

BACKGROUND OF THE INVENTION

The present invention relates to substituted imidazole compounds which have anti-cancer activity. Numerous anti-cancer compounds in unrelated chemical classes have been synthesized or derived from naturally occurring plants and organisms. None are presently available which demonstrate the anti-cancer activity that has been discovered with respect to the compounds of the present invention. The compounds of the present invention demonstrate anti-cancer activity through the antagonism of the kinase, Raf. The raf genes code for a family of proteins which can be oncogenically activated through N-terminal fusion, truncation or point mutations. RAF can be activated and undergoes rapid phosphorylation in response to PDGF, EGF, insulin, thrombin, endothelin, acidic FGF, CSF1 or TPA, as well as in response to oncoproteins v-fms, v-src, v-sis, Hras and polyoma middle T antigen. Antisense constructs which reduce cellular levels of c-Raf, and hence Raf activity, inhibit the growth of oncogene-transformed rodent fibroblasts in soft agar, while exhibiting little or no general cytotoxicity. Since inhibition of growth in soft agar is highly predictive of tumor responsiveness in whole animals, these studies suggest that the antagonism of RAF is an effective means by which to treat cancers in which RAF plays a role.

Examples of such cancers, where RAF is implicated through overexpression include cancers of the brain, genitourinary tract, lymphatic system, stomach, larynx and lung. More particularly, such examples include histiocytic lymphoma, lung adenocarcinoma and small cell lung cancers. Additional examples include cancers in which overexpression or activation of Raf-activating oncogenes (e.g., K-ras, erb-B) is observed. More particularly, such cancers include pancreatic and breast carcinoma.

Numerous compounds of the present invention also inhibit cytokines and the pathology which is associated with diseases wherein cytokines are present in high levels. Cytokine mediated diseases refers to diseases or conditions in which excessive or unregulated production or activity of one or more cytokines occurs. Interleukin-1 (IL-1) and Tumor Necrosis Factor (TNF) are cytokines produced by a variety of cells which are involved in immunoregulation and other physiological conditions.

There are many disease states in which IL-1 is implicated. Included among these diseases are rheumatoid arthritis, osteoarthritis, endotoxemia, toxic shock syndrome, acute and chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes.

Interleukin-1 has also been demonstrated to mediate a variety of biological activities thought to be important in immunoregulation and other physiological conditions. [See, e.g., Dinarello et al., Rev. Infect. Disease, 6, 51 (1984)]. The known biological activities of IL-1 include the activation of T helper cells, induction of fever, stimulation of prostaglandin or collagenase production, neutrophil cherootaxis, induction of acute phase proteins and the suppression of plasma iron levels.

Excessive or unregulated tumor necrosis factor (TNF) production or activity has likewise been implicated in mediating or exacerbating rheumatoid arthritis, rheumatoid spondylitis, osteoarthritis, gouty arthritis, and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejections, fever and myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Monokines, such as TNF, have also been shown to activate HIV replication in monocytes and/or macrophages [See Poli, et al., Proc. Natl. Acad. Sci., 87:782–784 (1990)], therefore, inhibition of monokine production or activity aids in limiting HIV progression. TNF has been implicated in various roles with other viral infections, such as the cytomegalovirus (CMV), influenza virus, and the herpes virus.

Interleukin-6 (IL-6) is a cytokine effecting the immune system and hematopoiesis. It is produced by several mammalian cell types in response to agents such as IL-1, and is correlated with disease states such as angiofollicular lymphoid hyperplasia.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, endothelial cells and ketainocytes. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD11b/CD 18) on neutrophils without de novo protein synthesis.

There remains a need for compounds which are effective for treating cancer in which RAF is implicated, as well as compounds which inhibit, suppress or antagonize the production or activity of cytokines such as IL-1, IL-6, IL-8 and TNF.

SUMMARY OF THE INVENTION

The present invention relates to a compound represented by formula I:

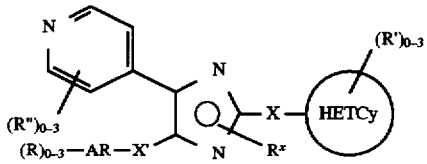

or a pharmaceutically acceptable salt thereof, wherein:

AR represents an aromatic group containing 6–10 atoms;
X and X' each independently represent —(CH$_2$)$_m$—Y—(CH$_2$)$_n$—, wherein m and n represent integers within the range of from 0–4, such that the sum of m and n is from 0–6; Y represents a member selected from the group consisting of: a direct bond; O; S(O)y, with y equal to 0, 1 or 2; $NR^{q'}$, with $R^{q'}$ as defined below; C(O); OC(O); C(O)O; $SO_xNR^{q'}$ with x equal to 1 or 2 and $R^{q'}$ as defined below; $NR^{q'}SO_x$; C(O)$NR^{q'}$ and $NR^{q'}C(O)$;

represents a 4 to 10 membered non-aromatic heterocycle containing at least one N atom, and optionally containing 1–2 additional N atoms and 0–1 O or S atom;

$R^x$ represents H, $C_{1-6}$alkyl($R^q$)$_3$, $OC_{1-6}$alkyl($R^q$)$_3$ or C(O) $C_{1-6}$alkyl($R^q$)$_3$;

each R and R" independently represents a member selected from the group consisting of: halo; hydroxy; $C_{1-6}$alkyl($R^q$)$_3$; $OC_{1-6}$ alkyl($R^q$)$_3$; $C_{3-8}$cycloalkyl($R^q$)$_3$; CN; $CONH_2$; $CONHC_{1-6}$ alkyl($R^q$)$_3$; CON($C_{1-6}$alkyl ($R^q$)$_3$)$_2$; $NH_2$; $NHC_{1-6}$alkyl($R^q$)$_3$; N($C_{1-6}$alkyl($R^q$)$_3$)$_2$; $CO_2H$; $CO_2C_{1-6}$alkyl($R^q$)$_3$; C(O)$C_{1-6}$ alkyl($R^q$)$_3$; aryl ($R^q$)$_3$; heteroaryl($R^q$)$_3$; $CF_3$; SH; $NO_2$; $SO_yC_{1-6}$ alkyl ($R^q$)$_3$, with y as defined above; $SO_2NH_2$; $SO_2NHC_{1-6}$ alkyl($R^q$)$_3$; $SO_2N(C_{1-6}$alkyl($R^q$)$_3$)$_2$; $NHSO_2C_{1-6}$alkyl ($R^q$)$_3$, $NHSO_2$aryl($R^q$)$_3$, $NHSO_2$heteroary($R^q$)$_3$, N($R^{q'}$) C(O)$C_{1-6}$alkyl($R^q$)$_3$; $NR^{q'}C(O)NH(C_{1-6}$alkyl($R^q$)$_3$); $C_{2-4}$alkenyl($R^q$)$_{2-3}$ and $C_{2-4}$ alkynyl($R^q$)$_{1-3}$;

each R' independently represents a member selected from the group consisting of: hydroxy; $C_{1-6}$alkyl($R^q$)$_3$; $C_{3-8}$cycloalkyl($R^q$)$_3$; $OC_{1-6}$alkyl($R^q$)$_3$; $OC_{3-8}$cycloalkyl($R^q$)$_3$; heterocyclyl($R^q$)$_3$; CN; NH(Rq"); $NHC_{1-6}$alkyl($R^q$)$_3$; N($C_{1-6}$alkyl($R^q$)$_3$)$_2$; $NHC_{3-8}$cycloalkyl($R^q$)$_3$; N($C_{3-8}$cycloalkyl($R^q$)$_3$)$_2$; $CF_3$; SH; $NO_2$; $C_{2-4}$alkenyl($R^q$)$_{2-3}$, aryl($R^q$)$_3$, heteroaryl($R^q$)$_3$; $C_{2-4}$alkynyl($R^q$)$_{1-3}$; —OC(O)$C_{3-8}$cycloalkyl($R^q$)$_3$; $SO_2NH_2$; $SO_2NHC_{1-6}$alkyl($R^q$)$_3$; $SO_2N(C_{1-6}$alkyl($R^q$)$_3$)$_2$; $NHSO_2C_{1-6}$alkyl($R^q$)$_3$, $NHSO_2$aryl($R^q$)$_3$, $NHSO_2$heteroary($R^q$)$_3$, —OC(O)heterocyclyl($R^q$)$_3$; N($R^{q'}$)C(O)$OC_{1-6}$alkyl($R^q$)$_3$; $NR^{q'}C(O)NH(C_{1-6}$alkyl ($R^q$)$_3$); —OC(O)$C_{1-6}$alkyl($R^q$)$_3$; —OC(O)aryl($R^q$)$_3$, —OC(O)heteroaryl($R^q$)$_3$; —C(=$NR^{q'}$)$NH_2$; —C(=$N^q$)$NHC_{1-6}$alkyl($R^q$)$_3$, —C(=$N^q$)N($C_{1-6}$alkyl ($R^q$)$_3$)$_2$; $CONH_2$; $CONHC_{1-6}$alkyl($R^q$)$_3$; CON($C_{1-6}$alkyl($R^q$)$_3$)$_2$; $CONHC_{3-8}$ cycloalkyl($R^q$)$_3$; CON($C_{3-8}$-cycloalkyl($R^q$)$_3$)$_2$; $CO_2H$; $CO_2C_{1-6}$ alkyl($R^q$)$_3$; C(O) $C_{1-6}$alkyl($R^q$)$_3$; $CO_2C_{3-8}$cycloalkyl($R^q$)$_3$; C(O)$C_{3-8}$cycloalkyl($R^q$)$_3$; —[C(O)(CH$_2$)$_j$—$CR^5R^6$—(CH$_2$)$_k$— $NR^7$]$_p$—$R^8$; —C(O)$C_{3-8}$cycloalkyl($R^q$)$_3$; —C(O) heterocyclyl($R^q$)$_3$; —CON[$C_{1-6}$alkyl($R^q$)$_3$][$C_{3-8}$cycloalkyl($R^q$)$_3$]; —C(O)aryl($R^q$)$_3$, —C(O)heteroaryl ($R^q$)$_3$;

and

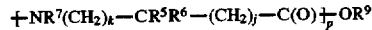

j and k independently represent integers of from 0–3;

$R^5$ and $R^6$ are independently H, aryl, $C_{1-6}$alkyl($R^q$)$_3$, or $CR^5R^6$ in combination represents a 3, 4, 5 or 6 membered cycloalkyl or heterocyclyl group, an aryl group or a heteroaryl group;

p represents 1, 2 or 3, with the proviso that when p represents 1, $CR^5R^6$ represents a 3, 4, 5 or 6 membered cycloalkyl group or a heterocyclyl group, an aryl group or a heteroaryl group, and at least one of j and k is 1, 2 or 3;

$R^7$ and $R^8$ are independently H, $C_{1-6}$alkyl or aryl;

$R^9$ represents H, a negative charge balanced by a positively charged group or a protecting group;

$R^q$ represents a member selected from the group consisting of: $R^{q'}$; CN; $CO_2H$; $CO_2C_{1-4}$alkyl; C(O)$C_{1-4}$alkyl; NH($R^{q'}$); aryl($R^a$)$_3$; heteroaryl($R^a$)$_3$; $NHC_{1-4}$alkyl; N($C_{1-4}$alkyl)$_2$; $CONH_2$; SH; S(O)$_y$ $C_{1-6}$alkyl($R^a$)$_3$; C(O)$NHC_{1-6}$alkyl($R^a$)$_3$; C(O)N($C_{1-6}$ alkyl($R^a$)$_3$)$_2$; NHC(NH)$NH_2$; -heteroalkyl($R^a$)$_3$; —NHC(O)$NH_2$;

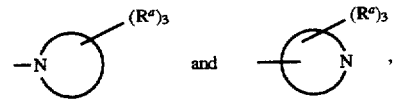

wherein independently represent mono or bicyclic ring systems, non-aromatic or partially aromatic, containing from 5–10 ring atoms, 1–4 of which are N and 0–1 of which are O or S(O)$_y$, with y equal to 0, 1 or 2, optionally containing 1–2 carbonyl groups;

each $R^a$ independently represents a member selected from the group consisting of: H, $C_{1-6}$alkyl, $OC_{1-6}$alkyl, aralkyl, substituted aralkyl, heteroaralkyl, substituted heteroaralkyl, aralkoxy, substituted aralkoxy, halo, hydroxy, CN, $CONH_2$, $CONHC_{1-6}$alkyl, CON($C_{1-6}$ alkyl)$_2$, $CO_2H$, $CO_2C_{1-6}$alkyl, C(O)$C_{1-6}$alkyl, phenyl, $CF_3$, SH, $NO_2$, $SO_yC_{1-6}$alkyl, with y as defined above; $SO_2NH_2$, $SO_2NHC_{1-6}$ alkyl, $NHSO_2$(substituted aryl), $NHSO_2$(substituted heteroaryl), $NHSO_2C_{1-6}$alkyl, $NHSO_2$aryl, $NHSO_2$heteroaryl, $NH_2$, $NHC_{1-6}$alkyl, N($C_{1-6}$alkyl)$_2$, $NHC(O)C_{1-6}$alkyl, $NHC(O)NH(C_{1-6}$alkyl), $C_{2-4}$ alkenyl and $C_{2-4}$alkynyl;

$R^{q'}$ represents H, OH, $C_{1-4}$alkyl, —$OC_{1-4}$alkyl, aryl or C(O)$OC_{1-4}$alkyl, and $R^{q''}$ represents H, OH or $OC_{1-4}$alkyl.

A pharmaceutical composition is also included in the invention described herein, which is comprised of a compound of formula I as defined above in combination with a pharmaceutically acceptable carrier.

A method of treating cancer is also included herein, which is comprised of administering to a mammalian patient in need of such treatment a compound of formula I as defined above, in an amount which is effective to treat cancer.

Also include in the invention is a method of treating a cytokine mediated disease in a mammal, comprising administering to a mammalian patient in need of such treatment an amount of a compound of formula I which is effective to treat said cytokine mediated disease.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

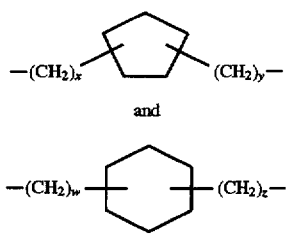

wherein: x and y=from 0–10; and w and z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

Heteroalkyl means an alkyl group containing from 2–15 carbon atoms and being interrupted by from 1–4 heteroatoms selected from O, S and N.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one or two groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups.

Heteroaryl thus includes aromatic and partially aromatic groups which contain one or more heteroatoms. Examples of this type are thiophene, purine, imidazopyridine, pyridine, oxazole, thiazole, oxazine, pyrazole, tetrazole, imidazole, pyridine, pyrimidine, pyrazine and triazine. Examples of partially aromatic groups are tetrahydroimidazo[4,5-c] pyridine, phthalidyl and saccharinyl, as defined below.

Each $R^a$ independently represents a member selected from the group consisting of: H, $C_{1-6}$alkyl, $OC_{1-6}$alkyl, aralkyl, substituted aralkyl, heteroaralkyl, substituted heteroaralkyl, aralkoxy, substituted aralkoxy, halo, hydroxy, CN, $CONH_2$, $CONHC_{1-6}$alkyl, $CON(C_{1-6}$alkyl$)_2$, $CO_2H$, $CO_2C_{1-6}$alkyl, $C(O)C_{1-6}$alkyl, phenyl, $CF_3$, SH, $NO_2$, $SO_yC_{1-6}$alkyl, with y as defined above; $SO_2NH_2$, $SO_2NHC_{1-6}$alkyl, $NHSO_2$(substituted aryl), $NHSO_2$(substituted heteroaryl), $NHSO_2C_{1-6}$alkyl, $NHSO_2$aryl, $NHSO_2$heteroaryl, $NH_2$, $NHC_{1-6}$alkyl, $N(C_{1-6}$alkyl$)_2$, $NHC(O)C_{1-6}$alkyl, $NHC(O)NH(C_{1-6}$alkyl$)$, $C_{2-4}$ alkenyl and $C_{2-4}$alkynyl. In substituted aralkyl, substituted heteroaralkyl and substituted aralkoxy, the aryl, heteroaryl or alkyl portions thereof can be substituted as appropriate.

Substituted alkyl, aryl and heteroaryl, and the substituted portions of aralkyl, aralkoxy, heteroaralkyl, heteroaralkoxy and like groups are substituted with from 1–3 groups selected from the group consisting of: halo, hydroxy, cyano, acyl, acylamino, aralkoxy, alkylsulfonyl, arylsulfonyl, alkylsulfonylamino, arylsulfonylamino, alkylaminocarbonyl, alkyl, alkoxy, aryl, aryloxy, aralkoxy, amino, alkylamino, dialkylamino, and sulfonylamino.

The terms "heterocycloalkyl" and "heterocyclyl" refer to a cycloalkyl group (nonaromatic) in which one of the carbon atoms in the ring is replaced by a heteroatom selected from O, $S(O)_y$ or N, and in which up to three additional carbon atoms may be replaced by said heteroatoms. When three heteroatoms are present in the heterocycle, they are not all linked together.

Examples of heterocyclyls are piperidinyl, morpholinyl, pyrrolidinyl, tetrahydrofuranyl, imidazolinyl, piperazinyl, pyrolidine-2-one, piperidine-2-one and the like.

Acyl as used herein refers to —$C(O)C_{1-6}$alkyl and —$C(O)$— aryl.

Acylamino refers to the group —$NHC(O)C_{1-6}$alkyl and —$NHC(O)$aryl.

Aralkoxy refers to the group —$OC_{1-6}$alkylaryl.

Alkylsulfonyl refers to the group —$SO_2C_{1-6}$alkyl.

Alkylsulfonylamino refers to the group —$NHSO_2C_{1-6}$alkyl.

Arylsulfonylamino refers to the group —$NHSO_2$aryl.

Alkylaminocarbonyl refers to the group —$C(O)NHC_{1-6}$alkyl.

Aryloxy refers to the group -O-aryl.

Sulfonylamino refers to the group —$NHSO_3H$.

Halo means Cl, F, Br and I selected on an independent basis.

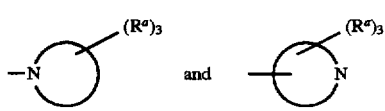

are optional substituents linked to the HETCy group.

independently represent mono or bicyclic ring systems, non-aromatic or partially aromatic, containing from 5–10 ring atoms, 1–4 of which are N and 0–1 of which are O or $S(O)_y$, with y equal to 0, 1 or 2, and when partially aromatic, the non-aromatic portion thereof optionally containing 1–2 carbonyl groups. Hence, these ring systems can be heteroaryl or heterocyclic as defined above.

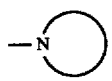

is linked to HETCy through a nitrogen atom contained in the ring system, either directly or through a linking group which is part of R'. Examples include phthalidyl and saccharinyl, as further defined below.

is likewise linked to HETCy, but through a carbon atom contained in the ring system.

The term phthalidyl refers to the heteroaryl

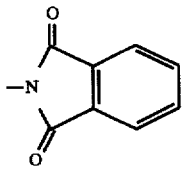

group:

The term saccharinyl refers to the heteroaryl

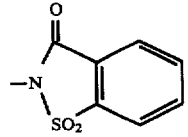

group:

The group

—O$\pm$C(O)—(CH$_2$)$_j$—CR$^5$R$^6$—(CH$_2$)$_k$—NR$^7$$\frac{}{p}$R$^8$ means —O—C(O)—(CH$_2$)$_j$—CR$^5$R$^6$—(CH$_2$)$_k$—NR$^7$—R$^8$, —O—C(O)—(CH$_2$)$_j$—CR$^5$R$^6$—(CH$_2$)$_k$—NR$^7$C(O)(CH$_2$)$_j$CR$^5$R$^6$(CH$_2$)$_k$NR$^7$R$^8$ and —OC(O)(CH$_2$)$_j$CR$^5$R$^6$(CH$_2$)$_k$NR$^7$C(O)(CH$_2$)$_j$CR$^5$R$^6$(CH$_2$)$_k$NR$^7$C(O)(CH$_2$)$_j$CR$^5$R$^6$(CH$_2$)$_k$NR$^7$R Within —[C(O)(CH$_2$)$_j$—CR$^5$R$^6$—(CH$_2$)$_k$—NR$^7$]$_p$—R$^8$, there may be from 1 to 3 groups —[C(O)(CH$_2$)$_j$—CR$^5$R$^6$—(CH$_2$)$_k$—NR$^7$]—. Thus, —[C(O)(CH$_2$)$_j$—CR$^5$R$^6$—(CH$_2$)$_k$—NR$^7$]$_p$—R$^8$ with p equal to 1, 2 or 3 means the following:

—C(O)(CH$_2$)$_j$—CR$^5$R$^6$—(CH$_2$)$_k$—NR$^7$—R$^8$;

—C(O)(CH$_2$)$_j$—CR$^5$R$^6$—(CH$_2$)$_k$—NR$^7$—C(O)(CH$_2$)$_j$—CR$^5$R$^6$—(CH$_2$)$_k$—NR$^7$R$^8$; and —C(O)(CH$_2$)$_j$CR$^5$R$^6$(CH$_2$)$_k$NR$^7$C(O)(CH$_2$)$_j$CR$^5$R$^6$—(CH$_2$)$_k$NR$^7$C(O)(CH$_2$)$_j$CR$^5$R$^6$(CH$_2$)$_k$NR$^7$R$^8$.

Likewise, the group $+$NR$^7$(CH$_2$)$_k$—CR$^5$R$^6$—(CH$_2$)$_j$—C(O)$\frac{}{p}$OR$^9$ means —NR$^7$—(CH$_2$)$_k$—CR$^5$R$^6$—(CH$_2$)$_j$—C(O)—OR$^9$, NR$^7$(CH$_2$)$_k$CR$^5$R$^6$(CH$_2$)$_j$CO$_2$R$^9$ or —NR$^7$(CH$_2$)$_k$CR$^5$R$^6$(CH$_2$)$_j$C(O)NR$^7$(CH$_2$)$_k$CR$^5$R$^6$(CH$_2$)$_j$C(O)NR$^7$(CH$_2$)$_k$CR$^5$R$^6$(CH$_2$)$_j$CO$_2$R$^9$.

The variables are determined independently within each group. Thus, e.g., when more than one j is present, they may be the same or different. The values of $R^5$ and $R^6$ can be H, $C_{1-6}$alkyl($R^9$)$_3$ or aryl, or $CR^5R^6$ taken in combination represents a 3–6 membered cycloalkyl or heterocyclyl group, an aryl group or a heteroaryl group. Examples of suitable $CR^5R^6$ groups include:

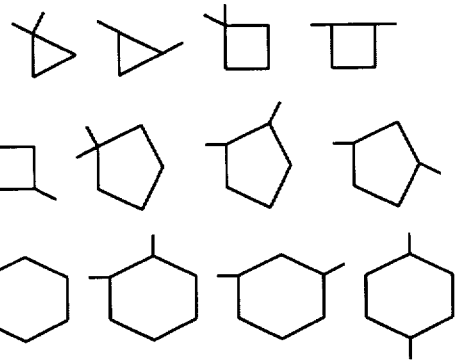

The patterns of attachment noted above can also include heteroatoms as appropriate. When an aryl or heteroaryl group is represented by $CR^5R^6$, attachment cannot be through the same carbon atom.

The term "TNF mediated disease or disease state" refers to disease states in which TNF plays a role, either by production or increased activity levels of TNF itself, or by causing another monokine to be released, such as but not limited to IL-1 or IL-6. A disease state in which IL-1, for instance is a major component, and whose production or action, is exacerbated or secreted in response to TNF, would therefore be considered a disease state mediated by TNF.

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor-beta (TNF-b).

By the term "cytokine interfering or cytokine suppresive amount" is mean an effective amount of a compound of formula I which will cause a decrease in the in vivo activity or level of the cytokine to normal or sub-normal levels, when given to the patient for the prophylaxis or therapeutic treatment of a disease state which is exacerbated by, or caused by, excessive or unregulated cytokine production or activity.

The compounds of the present invention may contain one or more asymmetric carbon atoms and may exist in racemic and optically active forms. All are within the scope of the present invention.

One subset of compounds of the present invention which is of interest relates to compounds of formula I wherein one or two R" are present, each independently representing a member selected from the group consisting of: $NH_2$, $NHC_{1-6}alkyl(R^q)_3$, $N(C_{1-6}alkyl)_2$, $N(R^{q'})C(O)C_{1-6}alkyl(R^q)_3$ and $NR^qC(O)NHC_{1-6}alkyl(R^q)^3$.

Another subset of compounds of the present invention which is of interest relates to compounds of formula I wherein AR represents a phenyl ring unsubstituted or substituted with one or two R groups.

Another subset of compounds of the present invention which is of interest relates to compounds of formula I wherein AR is phenyl and one or two R groups are present which are selected from the group consisting of: hydroxyl, halo, $C_{1-6}alkyl(R^q)_3$, $OC_{1-6}alkyl(R^q)_3$, $NH_2$, $CF_3$ and $NO_2$.

Another subset of compounds of the present invention which is of interest relates to compounds of formula I wherein each R represents halo, hydroxy or $CF_3$.

Another subset of compounds of the present invention which is of interest relates to compounds of formula I wherein HETCy represents a 5–6 membered non-aromatic heterocycle with 1–2 nitrogen atoms contained therein.

Another subset of compounds of the present invention which is of interest relates to compounds of formula I wherein each R' is selected from the group consisting of: $C_{1-6}alkyl(R^q)_3$, $OC_{1-6}alkyl(R^q)_3$, CN and $NO_2$.

Another subset of compounds of the present invention which is of interest relates to compounds of formula I wherein $R^q$ is selected from $R^{q'}$, CN, $NH(R^{q''})$

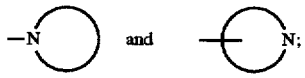

$R^{q'}$ represents H, $C_{1-4}alkyl$, OH or aryl;
$R^{q''}$ represents H or OH;

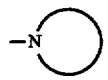

represents a bicyclic partially aromatic group selected from phthalidyl and saccharinyl, and

represents piperidinyl.

Another subset of compounds of the present invention which is of interest relates to compounds of formula I wherein each R' represents a member selected from the group consisting of: $—OC(O)C_{3-8}cycloalkyl(R^q)_3$, $—OC(O)heterocyclyl(R^q)_3$, $N(R^{q'})C(O)C_{1-6}$ alkyl$(R^q)_3$, $—N(R^{q'})C(O)NH(C_{1-6}alkyl(R^q)_3$, $—OC(O)C_{1-6}alkyl(R^q)_3$, $—OC(O)aryl(R^q)_3$, $—OC(O)heteroaryl(R^q)_3$, $—O[C(O)(CH_2)_j—CR^5R^6—(CH_2)_k—NR^7]_pR^8$, and $—[NR^7—(CH_2)_kCR^5R^6—(CH_2)_j—C(O)]_p—OR^9$.

Another subset of compounds of the present invention which is of interest relates to compounds of formula I wherein $R^q$ represents H, $C_{1-4}alkyl$ or $OC_{1-4}alkyl$;

$R^{q''}$ represents H or $C_{1-4}alkyl$;

p is 1 or 2; when p is 1, j represents 1 and k represents 0, 1 or 2; when p is 2, j represents 0 or 1, and k represents 0, 1 or 2;

$R^5$ and $R^6$ represent H or $C_{1-6}alkyl(R^q)_3$ or one of $R^5$ and $R^6$ represents aryl and the other is H or $C_{1-6}alkyl(R^q)_3$;

$R^7$ and $R^8$ represent H or $C_{1-6}alkyl(R^q)_3$, and $R^9$ represents H.

Another subset of compounds of the present invention which is of interest relates to compounds of formula I wherein each R' represents a member selected from the group consisting of:

$CONH_2$; $CONHC_{1-6}alkyl(R^q)_3$; $CON(C_{1-6}alkyl(R^q)_3)_2$; $CONHC_{3-8}cycloalkyl(R^q)_3$; $CON(C_{3-8}cycloalkyl(R^q)_3)_2$; $CO_2H$; $CO_2C_{1-6}$ alkyl$(R^q)_3$; $C(O)C_{1-6}alkyl(R^q)_3$; $CO_2C_{3-8}cycloalkyl(R^q)_3$; $C(O)C_{3-8}cycloalkyl(R^q)_3$; $—[C(O)(CH_2)_j—CR^5R^6—(CH_2)_k—NR^7]_p—R^8$; $—C(O)C_{3-8}cycloalkyl(R^q)_3$; $—C(O)heterocyclyl(R^q)_3$; $CON[C_{1-6}alkyl(R^q)_3][C_{3-8}cycloalkyl(R^q)_3]$; $C(O)aryl(R^q)_3$ and $C(O)heteroaryl(R^q)_3$;

p represents 1, 2 or 3, and all other variables are as previously defined.

Another subset of compounds of the present invention which is of interest relates to compounds of formula I wherein each R' independently represents a member selected from the group consisting of:

$CONH_2$; $CONHC_{1-6}alkyl(R^q)_3$; $CON(C_{1-6}alkyl(R^q)_3)_2$; $CO_2H$; $CO_2C_{1-6}alkyl(R^q)_3$; $C(O)C_{1-6}alkyl(R^q)_3$; $—[C(O)(CH_2)_j—CR^5R^6—(CH_2)_k—NR^7]_pR^8$; $C(O)aryl(R^q)_3$ and $C(O)heteroaryl(R^q)_3$;

$R^q$ is $R^{q'}$, CN,

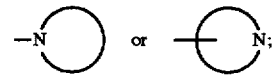

$R^{q'}$ represents H, $C_{1-4}alkyl$, OH or aryl;

represents a bicyclic partially aromatic group selected from phthalidyl and saccharinyl, and

represents piperidinyl.

Another subset of compounds of the present invention which is of interest relates to compounds of formula I wherein R' represents a member selected from the group consisting of: $CONH_2$; $CO_2H$; $CO_2C_{1-6}alkyl(R^q)_3$; $C(O)C_{1-6}alkyl(R^q)_3$; and $—[C(O)(CH_2)_j—CR^5R^6—(CH_2)_k—NR^7]_pR^8$;

$R^q$ represents H, $C_{1-4}alkyl$ or $OC_{1-4}alkyl$;

p represents 1;

j represents 0 or 1;

k represents 0, 1 or 2; and each $R^7$ and $R^8$ preferably represents H or $C_{1-6}alkyl(R^q)_3$.

Another subset of compounds of the present invention which is of interest relates to compounds of formula I wherein $R^x$ is H or $C_{1-6}$alkyl$(R^q)_3$.

Another subset of compounds of the present invention which is of interest relates to compounds of formula I wherein X' represents a direct bond.

Another subset of compounds of the present invention which is of interest relates to compounds of formula I wherein X represents —$(CH_2)_m$—Y—$(CH_2)_n$—, Y represents a direct bond, O, S or C(O); m represents 0 or 1 and n represents 0 or 1.

More particularly, another subset of compounds of the present invention which is of interest relates to compounds of formula I wherein X represents a direct bond.

More particularly, in a related aspect of the invention, a subset of compounds of the present invention which is of interest relates to compounds of formula I wherein:

AR represents phenyl or naphthyl;

X and X' represent —$(CH_2)_m$—Y—$(CH_2)_n$—, wherein m and n are zero and Y is a bond;

HETCy represents a pyrrolidinyl or piperidinyl group;

one or two R groups are present and are selected from the group consisting of: halo, hydroxy, $C_{1-6}$alkyl$(R^q)_3$, $OC_{1-6}$alkyl$(R^q)_3$, CN, $NH_2$, $CO_2H$, $CF_3$, $NO_2$ and $SO_2NH_2$;

one or two R' groups are present and are selected from the group consisting of $C_{1-6}$alkyl$(R^q)_3$, $OC_{1-6}$alkyl$(R^q)_3$, CN and $NO_2$;

$R^q$ represents $R^{q'}$, CN, $CO_2H$, $NH(R^{q'})$,

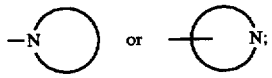

$R^{q'}$ represents H, $C_{1-4}$alkyl, OH or phenyl;
$R^{q''}$ represents H or OH;

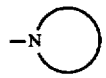

represents phthalidyl or saccharinyl, and

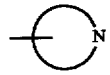

represents piperidinyl.

More particularly, another subset of compounds of the present invention which is of interest relates to compounds of formula I wherein:

AR represents an aromatic group containing 6–10 atoms;

X and X' each independently represent —$(CH_2)_m$—Y—$(CH_2)_n$—, wherein m and n represent integers within the range of from 0–4, such that the sum of m and n is from 0–6; Y represents a member selected from the group consisting of: a direct bond; O; $S(O)_y$, with y equal to 0, 1 or 2; $NR^{q'}$, with $R^{q'}$ as defined below; C(O); OC(O); C(O)O; $SO_xNR^{q'}$ with x equal to 1 or 2 and $R^{q'}$ as defined below; $NR^{q'}SO_x$; C(O)$NR^{q'}$ and $NR^{q'}$C(O);

represents a 4 to 10 membered non-aromatic heterocycle containing at least one N atom, and optionally containing 1–2 additional N atoms and 0–1 O or S atom;

$R^x$ represents H, $C_{1-6}$alkyl$(R^q)_3$, $OC_{1-6}$alkyl$(R^q)_3$ or C(O)$C_{1-6}$alkyl$(R^q)_3$;

each R independently represents a member selected from the group consisting of: halo; hydroxy; $C_{1-6}$alkyl$(R^q)_3$; $OC_{1-6}$ alkyl$(R^q)_3$; $C_{3-8}$cycloalkyl$(R^q)_3$; CN; $CONH_2$; $CONHC_{1-6}$ alkyl$(R^q)_3$; $CON(C_{1-6}$alkyl$(R^q)_3)_2$; $NH_2$; $NHC_{1-6}$alkyl$(R^q)_3$; $N(C_{1-6}$alkyl$(R^q)_3)_2$; $CO_2H$; $CO_2C_{1-6}$alkyl$(R^q)_3$; C(O)$C_{1-6}$ alkyl$(R^q)_3$; aryl$(R^q)_3$; heteroaryl$(R^q)_3$; $CF_3$; SH; $NO_2$; $NHSO_2C_{1-6}$alkyl$(R^q)_3$, $NHSO_2$aryl$(R^q)_3$, $NHSO_2$heteroary$(R^q)_3$, $N(R^{q'})$C(O)$C_{1-6}$alkyl$(R^q)_3$; $NR^{q'}$ C(O)NH$(C_{1-6}$alkyl$(R^q)_3)$; $C_{2-4}$alkenyl$(R^q)_{2-3}$ and $C_{2-4}$alkynyl$(R^q)_{1-3}$;

each R" independently represents a member selected from the group consisting of: halo; hydroxy; $C_{1-6}$alkyl$(R^q)_3$; $OC_{1-6}$ alkyl$(R^q)_3$; $C_{3-8}$cycloalkyl$(R^q)_3$; CN; $CONH_2$; $CONHC_{1-6}$ alkyl$(R^q)_3$; CON(Ci-6alkyl$(R^q)_3)_2$; $NH_2$; $NHC_{1-6}$alkyl$(R^q)_3$; $N(C_{1-6}$alkyl$(R^q)_3)_2$; $CO_2H$; $CO_2C_{1-6}$alkyl$(R^q)_3$; C(O)$C_{1-6}$ alkyl$(R^q)_3$; aryl$(R^q)_3$; heteroaryl$(R^q)_3$; $CF_3$; SH; $NO_2$; $SO_yC_{1-6}$ alkyl$(R^q)_3$, with y as defined above; $SO_2NH_2$; $SO_2NHC_{1-6}$alkyl$(R^q)_3$; $SO_2N(C_{1-6}$alkyl$(R^q)_3)_2$; $NHSO_2C_{1-6}$alkyl$(R^q)_3$, $NHSO_2$aryl$(R^q)_3$, $NHSO_2$heteroary$(R^q)_3$, $N(R^{q'})$C(O)$C_{1-6}$alkyl$(R^q)_3$; $NR^{q'}$C(O)NH$(C_{1-6}$alkyl$(R^q)_3)$; $C_{2-4}$alkenyl$(R^q)_{2-3}$ and $C_{2-4}$ alkynyl$(R^q)_{1-3}$;

each R' independently represents a member selected from the group consisting of: hydroxy; $C_{1-6}$alkyl$(R^q)_3$; $C_{3-8}$ cycloalkyl$(R^q)_3$; $OC_{1-6}$alkyl$(R^q)_3$; $OC_{3-8}$cycloalkyl $(R^q)_3$; heterocyclyl$(R^q)_3$; CN; NH(Rq"); $NHC_{1-6}$alkyl$(R^q)_3$; $N(C_{1-6}$alkyl$(R^q)_3)_2$; $NHC_{3-8}$cycloalkyl$(R^q)_3$; $N(C_{3-8}$cycloalkyl$(R^q)_3)_2$; $CF_3$; SH; $NO_2$; $C_{2-4}$alkenyl$(R^q)_{2-3}$, aryl$(R^q)_3$, heteroaryl$(R^q)_3$; $C_{2-4}$alkynyl$(R^q)_{1-3}$; —OC(O)$C_{3-8}$cycloalkyl$(R^q)_3$; $SO_2NH_2$; $SO_2NHC_{1-6}$alkyl$(R^q)_3$; $SO_2N(C_{1-6}$alkyl$(R^q)_3)_2$; $NHSO_2C_{1-6}$alkyl$(R^q)_3$, $NHSO_2$aryl$(R^q)_3$, $NHSO_2$heteroary$(R^q)_3$, —OC(O)heterocyclyl$(R^q)_3$; $N(R^{q'})$C(O)$C_{1-6}$alkyl$(R^q)_3$; $NR^{q'}$C(O)NH$(C_{1-6}$alkyl$(R^q)_3)$; —OC(O)$C_{1-6}$alkyl$(R^q)_3$; —OC(O)aryl$(R^q)_3$, —OC(O)heteroaryl$(R^q)_3$; —C(—$NR^{q'}$)$NH_2$; —C(=$N^{q'}$)$NHC_{1-6}$alkyl$(R^q)_3$, —C(=$N^{q'}$)$N(C_{1-6}$alkyl$(R^q)_3)_2$; $CONH_2$; $CONHC_{1-6}$alkyl$(R^q)_3$; $CON(C_{1-6}$alkyl$(R^q)_3)_2$; $CONHC_{3-8}$ cycloalkyl$(R^q)_3$; $CON(C_{3-8}$cycloalkyl$(R^q)_3)_2$; $CO_2H$; $CO_2C_{1-6}$ alkyl$(R^q)_3$; C(O)$C_{1-6}$alkyl$(R^q)_3$; $CO_2C_{3-8}$cycloalkyl$(R^q)_3$; C(O)$C_{3-8}$cycloalkyl$(R^q)_3$; —[C(O)(CH$_2$)$_j$—$CR^5R^6$—(CH$_2$)$_k$—$NR^7$]$_p$—$R^8$; —C(O)$C_{3-8}$cycloalkyl$(R^q)_3$; —C(O)heterocyclyl$(R^q)_3$; CON[$C_{1-6}$ alkyl$(R^q)_3$][$C_{3-8}$cycloalkyl$(R^q)_3$]; C(O)aryl$(R^q)_3$, C(O)heteroaryl$(R^q)_3$;

$$-O+C(O)-(CH_2)_j-CR^5R^6-(CH_2)_k-NR^7\}_p R^8$$

and $$+NR^7(CH_2)_k-CR^5R^6-(CH_2)_j-C(O)\}_p OR^9$$

j and k independently represent integers of from 0–3;
$R^5$ and $R^6$ are independently H, aryl, $C_{1-6}$alkyl$(R^q)_3$, or $CR^5R^6$ in combination represents a 3, 4, 5 or 6 membered cycloalkyl or heterocyclyl group, an aryl group or a heteroaryl group;

p represents 1, 2 or 3, with the proviso that when p represents 1, $CR^5R^6$ represents a 3, 4, 5 or 6 membered cycloalkyl group or a heterocyclyl group, an aryl group or a heteroaryl group, and at least one ofj and k is 1, 2 or 3;

$R^7$ and $R^8$ are independently H, $C_{1-6}$alkyl or aryl;

$R^9$ represents H, a negative charge balanced by a positively charged group or a protecting group;

$R^q$ represents a member selected from the group consisting of: $R^{q'}$; CN; $CO_2H$; $CO_2C_{1-4}$alkyl; $C(O)C_{1-4}$alkyl; $NH(R^{q'})$; aryl$(R^a)_3$; heteroaryl$(R^a)_3$; $NHC_{1-4}$alkyl; $N(C_{1-4}alkyl)_2$; $CONH_2$; SH; $S(O)_y$ $C_{1-6}$alkyl$(R^a)_3$; $C(O)NHC_{1-6}$alkyl$(R^a)_3$; $C(O)N(C_{1-6}$alkyl$(R^a)_3)_2$; $NHC(NH)NH_2$; -heteroalkyl$(R^a)_3$; $-NHC(O)NH_2$;

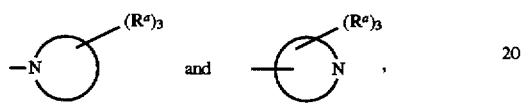

wherein

independently represent mono or bicyclic ring systems, non-aromatic or partially aromatic, containing from 5–10 ring atoms, 1–4 of which are N and 0–1 of which are O or $S(O)_y$, with y equal to 0, 1 or 2, optionally containing 1–2 carbonyl groups;

each $R^a$ independently represents a member selected from the group consisting of: H, $C_{1-6}$alkyl, $OC_{1-6}$alkyl, aralkyl, substituted aralkyl, heteroaralkyl, substituted heteroaralkyl, aralkoxy, substituted aralkoxy, halo, hydroxy, CN, $CONH_2$, $CONHC_{1-6}$alkyl, $CON(C_{1-6}$alkyl$)_2$, $CO_2H$, $CO_2C_{1-6}$alkyl, $C(O)C_{1-6}$alkyl, phenyl, $CF_3$, SH, $NO_2$, $SO_yC_{1-6}$alkyl, with y as defined above; $SO_2NH_2$, $SO_2NHC_{1-6}$ alkyl, $NHSO_2$(substituted aryl), $NHSO_2$(substituted heteroaryl), $NHSO_2C_{1-6}$alkyl, $NHSO_2$aryl, $NHSO_2$heteroaryl, $NH_2$, $NHC_{1-6}$alkyl, $N(C_{1-6}alkyl)_2$, $NHC(O)C_{1-6}$alkyl, $NHC(O)NH(C_{1-6}$alkyl), $C_{2-4}$ alkenyl and $C_{2-4}$alkynyl;

$R^{q'}$ represents H, OH, $C_{1-4}$alkyl, $-OC_{1-4}$alkyl, aryl or $C(O)C_{1-4}$alkyl, and $R^{q''}$ represents H, OH or $OC_{1-4}$alkyl.

Within this subset, another of the present invention which is of interest relates to compounds of formula I wherein X represents a bond.

More particularly, a subset of compounds of the present invention which is of interest, relates to compounds of formula Ia:

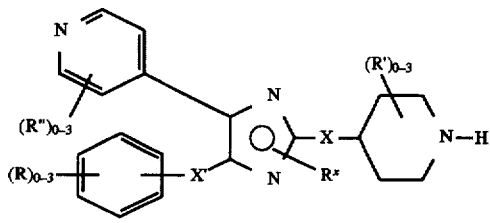

or a pharmaceutically acceptable salt thereof, wherein:

X and X' each independently represent $-(CH_2)_m-Y-(CH_2)_n-$, wherein m and n represent integers within the range of from 0–4, such that the sum of m and n is from 0–6; Y represents a member selected from the group consisting of: a direct bond; O; $S(O)_y$, with y equal to 0, 1 or 2; $NR^{q'}$, with $R^{q'}$ as defined below; C(O); OC(O); C(O)O; $SO_xNR^{q'}$ with x equal to 1 or 2 and $R^q$ as defined below; $NR^{q'}SO_x$; $C(O)NR^{q'}$ and $NR^{q'}C(O)$;

$R^x$ represents H, $C_{1-6}$alkyl$(R^q)_3$ or $OC_{1-6}$alkyl$(R^q)_3$;

each R independently represents a member selected from the group consisting of: halo; hydroxy; $C_{1-6}$alkyl$(R^q)_3$; $OC_{1-6}$ alkyl$(R^q)_3$; $C_{3-8}$cycloalkyl$(R^q)_3$; CN; $CONH_2$; $CONHC_{1-6}$ alkyl$(R^q)_3$; $CON(C_{1-6}$alkyl$(R^q)_3)_2$; $NH_2$; $NHC_{1-6}$alkyl$(R^q)_3$; $N(C_{1-6}$alkyl$(R^q)_3)_2$; $CO_2H$; $CO_2C_{1-6}$alkyl$(R^q)_3$; $C(O)C_{1-6}$ alkyl$(R^q)_3$; aryl$(R^q)_3$; heteroaryl$(R^q)_3$; $CF_3$; SH; $NO_2$; $NHSO_2C_{1-6}$ $_6$alkyl$(R^q)_3$, $NHSO_2$aryl$(R^q)_3$, $NHSO_2$heteroary$(R^q)_3$, $N(R^{q'})C(O)$ $C_{1-6}$alkyl$(R^q)_3$; $NR^{q'}C(O)NH(C_{1-6}$alkyl$(R^q)_3)$; $C_{2-4}$ alkenyl$(R^q)_{2-3}$ and $C_{2-4}$alkynyl$(R^q)_{1-3}$;

each R" independently represents a member selected from the group consisting of: halo; hydroxy; $C_{1-6}$alkyl$(R^q)_3$; $OC_{1-6}$ alkyl$(R^q)_3$; $C_{3-8}$cycloalkyl$(R^q)_3$; CN; $CONH_2$; $CONHC_{1-6}$ alkyl$(R^q)_3$; $CON(C_{1-6}$alkyl$(R^q)_3)_2$; $NH_2$; $NHC_{1-6}$alkyl$(R^q)_3$; $N(C_{1-6}$alkyl$(R^q)_3)_2$; $CO_2H$; $CO_2C_{1-6}$alkyl$(R^q)_3$; $C(O)C_{1-6}$ alkyl$(R^q)_3$; aryl$(R^q)_3$; heteroaryl $(R^q)_3$; $CF_3$; $SO_yC_{1-6}$alkyl$(R^q)_3$, with y as defined above; $SO_2NH_2$; $SO_2NHC_{1-6}$alkyl$(R^q)_3$; $SO_2N(C_{1-6}$alkyl$(R^q)_3)_2$; $NHSO_2C_{1-6}$alkyl$(R^q)_3$, $NHSO_2$aryl$(R^q)$ $_3$, $NHSO_2$heteroary$(R^q)_3$, $N(R^{q'})C(O)C_{1-6}$alkyl$(R^q)_3$; $NR^{q'}C(O)NH(C_{1-6}$alkyl$(R^q)_3)$; $C_{2-4}$alkenyl$(R^q)_{2-3}$ and $C_{2-4}$ alkynyl$(R^q)_{1-3}$;

each R' independently represents a member selected from the group consisting of: hydroxy; $C_{1-6}$alkyl$(R^q)_3$; $C_{3-8}$ cycloalkyl$(R^q)_3$; $OC_{1-6}$alkyl$(R^q)_3$; $OC_{3-8}$cycloalkyl $(R^q)_3$; heterocyclyl$(R^q)_3$; CN; $NH(R^{q'})$; $NHC_{1-6}$alkyl $(R^q)_3$; $N(C_{1-6}$ alkyl$(R^q)_3)_2$; $NHC_{3-8}$cycloalkyl$(R^q)_3$; $N(C_{3-8}$cycloalkyl$(R^q)_3)_2$; $CF_3$; $C_{2-4}$alkenyl$(R^q)_{2-3}$, aryl $(R^q)_3$, heteroaryl$(R^q)_3$; $C_{2-4}$ alkynyl$(R^q)_{1-3}$; $-OC(O)$ $C_{3-8}$cycloalkyl$(R^q)_3$; $SO_2NH_2$; $SO_2NHC_{1-6}$alkyl$(R^q)_3$; $SO_2N(C_{1-6}$alkyl$(R^q)_3)_2$; $-OC(O)$heterocyclyl$(R^q)_3$; $CONH_2$; $CONHC_{1-6}$alkyl$(R^q)_3$; $CON(C_{1-6}$alkyl$(R^q)_3)$ $_2$; $CONHC_{3-8}$cycloalkyl$(R^q)_3$; $CON(C_{3-8}$ cycloalkyl $(R^q)_3)_2$; C(O)aryl$(R^q)_3$, C(O)heteroaryl$(R^q)_3$;

$R^q$ represents a member selected from the group consisting of: $R^{q'}$; CN; $CO_2H$; $CO_2C_{1-4}$alkyl; $C(O)C_{1-4}$alkyl; $NH(R^{q'})$; aryl$(R^a)_3$; heteroaryl$(R^a)_3$; $NHC_{1-4}$alkyl; $N(C_{1-4}alkyl)_2$; $CONH_2$; SH; $S(O)_y$ $C_{1-6}$alkyl$(R^a)_3$; $C(O)NHC_{1-6}$alkyl$(R^a)_3$; $C(O)N(C_{1-6}$alkyl$(R^a)_3)_2$; $NHC(NH)NH_2$; -heteroalkyl$(R^a)_3$; $-NHC(O)NH_2$;

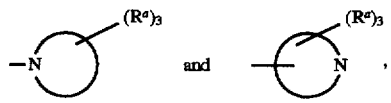

wherein

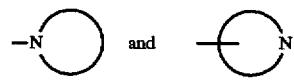

independently represent mono or bicyclic ring systems, non-aromatic or partially aromatic, containing from 5–10 ring atoms, 1–4 of which are N and 0–1 of which are O or S(O)$_y$, with y equal to 0, 1 or 2, optionally containing 1–2 carbonyl groups;

each R$^a$ independently represents a member selected from the group consisting of: H, C$_{1-6}$alkyl, OC$_{1-6}$alkyl, aralkyl, substituted aralkyl, heteroaralkyl, substituted heteroaralkyl, aralkoxy, substituted aralkoxy, halo, hydroxy, CN, CONH$_2$, CONHC$_{1-6}$alkyl, CON(C$_{1-6}$ alkyl)$_2$, CO$_2$H, CO$_2$C$_{1-6}$alkyl, C(O)C$_{1-6}$alkyl, phenyl, CF$_3$, SH, NO$_2$, SO$_y$C$_{1-6}$alkyl, with y as defined above; SO$_2$NH$_2$, SO$_2$NHC$_{1-6}$ alkyl, NHSO$_2$ (substituted aryl), NHSO$_2$(substituted heteroaryl), NHSO$_2$C$_{1-6}$alkyl, NHSO$_2$aryl, NHSO$_2$heteroaryl, NH$_2$, NHC$_{1-6}$alkyl, N(C$_{1-6}$alkyl)$_2$, NHC(O)C$_{1-6}$alkyl, NHC(O)NH(C$_{1-6}$alkyl), C$_{2-4}$ alkenyl and C$_{2-4}$alkynyl;

R$^{q'}$ represents H, OH, C$_{1-4}$alkyl, —OC$_{1-4}$alkyl, aryl or C(O)C$_{1-4}$alkyl, and R$^{q''}$ represents H, OH or OC$_{1-4}$alkyl.

More particularly, another subset of compounds of the present invention which is of interest relates to compounds of formula Ib:

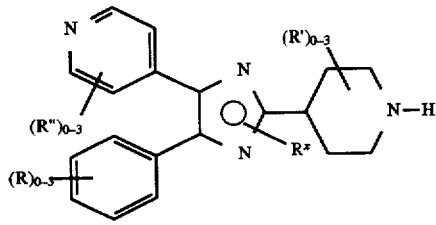

or a pharmaceutically acceptable salt thereof, wherein:

R$^x$ represents H, C$_{1-6}$alkyl(R$^q$)$_3$ or OC$_{1-6}$alkyl(R$^q$)$_3$;

each R independently represents a member selected from the group consisting of: halo; hydroxy; C$_{1-6}$alkyl(R$^q$)$_3$; OC$_{1-6}$ alkyl(R$^q$)$_3$; C$_{3-8}$cycloalkyl(R$^q$)$_3$; CN; CONH$_2$; CONHC$_{1-6}$ alkyl(R$^q$)$_3$; CON(C$_{1-6}$alkyl(R$^q$)$_3$)$_2$; NH$_2$; NHC$_{1-6}$alkyl(R$^q$)$_3$; N(C$_{1-6}$alkyl(R$^q$)$_3$)$_2$; CO$_2$H; CO$_2$C$_{1-6}$alkyl(R$^q$)$_3$; C(O)C$_{1-6}$ alkyl(R$^q$)$_3$; aryl(R$^q$)$_3$; heteroaryl (R$^q$)$_3$; CF$_3$; SH; NO$_2$; NHSO$_2$C$_{1-6}$alkyl(R$^q$)$_3$, NHSO$_2$aryl(R$^q$)$_3$, NHSO$_2$heteroary(R$^q$)$_3$, N(R$^{q'}$)C(O)C$_{1-6}$alkyl(R$^q$)$_3$; NR$^{q'}$C(O)NH(C$_{1-6}$alkyl(R$^q$)$_3$); C$_{2-4}$ alkenyl(R$^q$)$_{2-3}$ and C$_{2-4}$alkynyl(R$^q$)$_{1-3}$;

each R" independently represents a member selected from the group consisting of: halo; hydroxy; C$_{1-6}$alkyl(R$^q$)$_3$; OC$_{1-6}$ alkyl(R$^q$)$_3$; C$_{3-8}$cycloalkyl(R$^q$)$_3$; CN; CONH$_2$; CONHC$_{1-6}$ alkyl(R$^q$)$_3$; CON(C$_{1-6}$alkyl(R$^q$)$_3$)$_2$; NH$_2$; NHC$_{1-6}$alkyl(R$^q$)$_3$; N(C$_{1-6}$alkyl(R$^q$)$_3$)$_2$; CO$_2$H; CO$_2$C$_{1-6}$alkyl(R$^q$)$_3$; C(O)C$_{1-6}$ alkyl(R$^q$)$_3$; aryl(R$^q$)$_3$; heteroaryl (R$^q$)$_3$; CF$_3$; SO$_y$C$_{1-6}$alkyl(R$^q$)$_3$, with y as defined above; SO$_2$NH$_2$; SO$_2$NHC$_{1-6}$alkyl(R$^q$)$_3$; SO$_2$N(C$_{1-6}$alkyl(R$^q$)$_3$)$_2$; NHSO$_2$C$_{1-6}$alkyl(R$^q$)$_3$, NHSO$_2$aryl(R$^q$)$_3$, NHSO$_2$heteroary(R$^q$)$_3$, N(R$^{q'}$)C(O)C$_{1-6}$alkyl(R$^q$)$_3$; NR$^{q'}$C(O)NH(C$_{1-6}$alkyl(R$^q$)$_3$); C$_{2-4}$alkenyl(R$^q$)$_{2-3}$ and C$_{2-4}$ alkynyl(R$^q$)$_{1-3}$;

each R' independently represents a member selected from the group consisting of: hydroxy; C$_{1-6}$alkyl(R$^q$)$_3$; C$_{3-8}$ cycloalkyl(R$^q$)$_3$; OC$_{1-6}$alkyl(R$^q$)$_3$; OC$_{3-8}$cycloalkyl (R$^q$)$_3$; heterocyclyl(R$^q$)$_3$; CN; NH(R$^{q'}$); NHC$_{1-6}$alkyl (R$^q$)$_3$; N(C$_{1-6}$ alkyl(R$^q$)$_3$)$_2$; NHC$_{3-8}$cycloalkyl(R$^q$)$_3$; N(C$_{3-8}$cycloalkyl(R$^q$)$_3$)$_2$; CF$_3$; C$_{2-4}$alkenyl(R$^q$)$_{2-3}$, aryl (R$^q$)$_3$, heteroaryl(R$^q$)$_3$; C$_{2-4}$ alkynyl(R$^q$)$_{1-3}$; —OC(O) C$_{3-8}$cycloalkyl(R$^q$)$_3$; SO$_2$NH$_2$; SO$_2$NHC$_{1-6}$alkyl(R$^q$)$_3$; SO$_2$N(C$_{1-6}$alkyl(R$^q$)$_3$)$_2$; —OC(O)heterocyclyl(R$^q$)$_3$; CONH$_2$; CONHC$_{1-6}$alkyl(R$^q$)$_3$; CON(C$_{1-6}$alkyl(R$^q$)$_3$)$_2$; CONHC$_{3-8}$cycloalkyl(R$^q$)$_3$; CON(C$_{3-8}$ cycloalkyl (R$^q$)$_3$)$_2$; C(O)aryl(R$^q$)$_3$, C(O)heteroaryl(R$^q$)$_3$;

R$^q$ represents a member selected from the group consisting of: R$^{q'}$; CN; CO$_2$H; CO$_2$C$_{1-4}$alkyl; C(O)C$_{1-4}$alkyl; NH(R$^{q''}$); aryl(R$^a$)$_3$; heteroaryl(R$^a$)$_3$; NHC$_{1-4}$alkyl; N(C$_{1-4}$alkyl)$_2$; CONH$_2$; SH; S(O)$_y$ C$_{1-6}$alkyl(R$^a$)$_3$; C(O)NHC$_{1-6}$alkyl(R$^a$)$_3$; C(O)N(C$_{1-6}$alkyl(R$^a$)$_3$)$_2$; NHC(NH)NH$_2$; -heteroalkyl(R$^a$)$_3$; —NHC(O)NH$_2$;

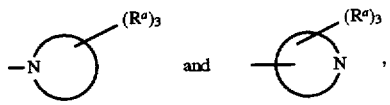

wherein

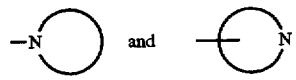

independently represent mono or bicyclic ring systems, non-aromatic or partially aromatic, containing from 5–10 ring atoms, 1–4 of which are N and 0–1 of which are O or S(O)$_y$, with y equal to 0, 1 or 2, optionally containing 1–2 carbonyl groups;

each R$^a$ independently represents a member selected from the group consisting of: H, C$_{1-6}$alkyl, OC$_{1-6}$alkyl, aralkyl, substituted aralkyl, heteroaralkyl, substituted heteroaralkyl, aralkoxy, substituted aralkoxy, halo, hydroxy, CN, CONH$_2$, CONHC$_{1-6}$alkyl, CON(C$_{1-6}$ alkyl)$_2$, CO$_2$H, CO$_2$C$_{1-6}$alkyl, C(O)C$_{1-6}$alkyl, phenyl, CF$_3$, SH, NO$_2$, SO$_y$C$_{1-6}$alkyl, with y as defined above; SO$_2$NH$_2$, SO$_2$NHC$_{1-6}$ alkyl, NHSO$_2$(substituted aryl), NHSO$_2$(substituted heteroaryl), NHSO$_2$C$_{1-6}$alkyl, NHSO$_2$aryl, NHSO$_2$heteroaryl, NH$_2$, NHC$_{1-6}$alkyl, N(C$_{1-6}$alkyl)$_2$, NHC(O)C$_{1-6}$alkyl, NHC(O)NH(C$_{1-6}$alkyl), C$_{2-4}$ alkenyl and C$_{2-4}$alkynyl;

R$^{q'}$ represents H, OH, C$_{1-4}$alkyl, —OC$_{1-4}$alkyl, aryl or C(O)C$_{1-4}$alkyl, and R$^{q''}$ represents H, OH or OC$_{1-4}$alkyl.

Representative examples of compounds of the present invention include the following species:

4-[5-(4-fluorophenyl)-4-pyridin-4-yl-1H-imidazol-2-yl]-piperidine-1-carboxylic acid tert-butyl ester;

4-benzyl-[4-(4-fluorophenyl)-5-pyridin-4-yl-1H-imidazol-2-yl]-piperidine-1-carboxylic acid tert-butyl ester;

3-[5-(4-fluorophenyl)-4-pyridin-4-yl-1H-imidazol-2-yl]-piperidine-1-carboxylic acid tert-butyl ester;

4-[5-(4-fluorophenyl)-4-pyridin-4-yl-1H-imidazol-2-yl]-1-acetylpiperidine;

4-[5-(4-fluorophenyl) -4-pyridin-4-yl-1H-imidazol-2-yl]-piperidine;

4-[5-(4-fluorophenyl)-4-pyridin-4-yl-1H-imidazol-2-yl]-1-methyl-piperidine;

4-[5-(4-fluorophenyl)-4-pyridin-4-yl-1H-imidazol-2-yl]-1-benzyl-piperidine;

4-[5-(4-fluorophenyl)-4-pyridin-4-yl-1H-imidazol-2-yl]-1-ethyl-piperidine;

4-[5-(3,4-dichlorophenyl)-4-pyridin-4-yl-1H-imidazol-2-yl]-piperidine;

4-[5-(3,4-dichlorophenyl)-4-pyridin-4-yl-1H-imidazol-2-yl]-1-methyl-piperidine;

2-(4-{4-[5-(3,4-dichlorophenyl)-4-pyridin-4-yl-1H-imidazol-2-yl]-pipeddin-1-yl}-butyl)-isoindole-1,3-dione;

2-(5-{4-[5-(3,4-dichlorophenyl)-4-pyridin-4-yl-1H-imidazol-2-yl]-pipeddin-1-yl}-pentyl)-isoindole-1,3-dione;

2-(6-{4-[5-(3,4-dichlorophenyl)-4-pyridin-4-yl-1H-imidazol-2-yl]-piperidin-1-yl}-hexyl)-isoindole-1,3-dione;

4-[5-(3,4-dichlorophenyl)-4-pyridin-4-yl-1H-imidazol-2-yl]-1-benzyl-piperidine;

2-(5-{4-[5-(3,4-dichlorophenyl)-4-pyridin-4-yl-1H-imidazol-2-yl]-piperidin-1-yl}-pentyl)-2,3-dihydro-isoindol-1-one;

4-(4-{4-[5-(3,4-dichlorophenyl)-4-pyridin-4-yl-1H-imidazol-2-yl]-piperidin-1-yl}-ethyl)-pyridine;

2-(5-{4-[5-(3,4-dichlorophenyl)-4-pyridin-4-yl-1H-imidazol-2-yl]-piperidin-1-yl}-pentyl)-1,1-dioxobenzo[d]isothiazol-3-one;

2-(4-{4-[5-(3,4-dichlorophenyl)-4-pyridin-4-yl-1H-imidazol-2-yl]-piperidin-1-yl}-butyl)-1,1-dioxobenzo[d]isothiazol-3-one;

4-[5-(3-hydroxyphenyl)-4-pyridin-4-yl-1H-imidazol-2-yl]-1-methyl-piperidine;

3-[5-(4-fluorophenyl)-4-pyridin-4-yl-1H-imidazol-2-yl]-piperidine;

3-[5-(4-fluorophenyl)-4-pyridin-4-yl-1H-imidazol-2-yl]-1-methyl-piperidine;

4-[5-(4-fluorophenyl)-4-pyridin-4-yl-1H-imidazol-2-yl]-1,4-dimethyl-piperidine;

4-benzyl-[4-(4-fluorophenyl)-5-pyridin-4-yl-1H-imidazol-2-yl]-piperidine-1-carboxylic acid tert-butyl ester;

4-benzyl-[4-(4-fluorophenyl)-5-pyridin-4-yl-1H-imidazol-2-yl]-piperidine;

2-amino-1-{5-[4-(3,4-dichlorophenyl)-4-pyridin-4-yl-1H-imidazol-2-yl]-piperidin-1-yl}-ethanone;

4-{5-(3,4-dichlorophenyl)-2-[1-(2-phenylethyl)-piperidin-4-yl]-1H-imidazol-4-yl}-pyridine;

4-{5-(3,4-dichlorophenyl)-2-[1-(3-phenylpropyl)-piperidin-4-yl]-1H-imidazol-4-yl}-pyridine;

2-(6-{4-[5-(3,4-dichlorophenyl)-4-pyridin-4-yl-1H-imidazol-2-yl]-piperidin-1-yl}-hexyl)-1,1-dioxobenzo[d]isothiazol-3-one;

2-(3-{4-[5-(3,4-dichlorophenyl)-4-pyridin-4-yl-1H-imidazol-2-yl]-piperidin-1-yl}-propyl)-1,1-dioxobenzo[d]isothiazol-3-one;

4-(5-{4-[5-(3,4-dichlorophenyl)-4-pyridin-4-yl-1H-imidazol-2-yl]-piperidin-1-yl-methyl}-imidazol-1-yl-methyl)-benzonitrile;

4-[2-[1-(4-benzyloxybenzyl)-piperidin-4-yl]-5-(3,4-dichlorophenyl)-1H-imidazol-4-yl-pyridine;

4-[4-fluorophenyl)-3-pyridin-yl-1H-imidazol-2-yl]-1-acetyl-piperidine;

3-[4-fluorophenyl)-3-pyridin-yl-1H-imidazol-2-yl]-1-acetyl-piperidine; and 2-(3-{4-[5-(3,4-dichlorophenyl)-4-pyridin-4-yl-1H-imidazol-2-yl]-piperidin-1-yl}-propyl)-isoindole-1,3-dione, as well as pharmaceutically acceptable salts thereof.

Additional examples of compounds of the present invention can be found in the following table:

| No. | Compound |
|---|---|
| 1 | |
| 2 | |
| 3 | |

-continued
| No. | Compound |
|---|---|
| 4 | 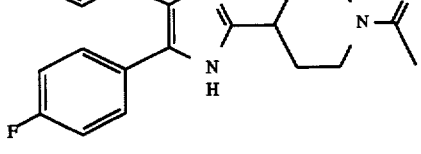 |
| 5 | 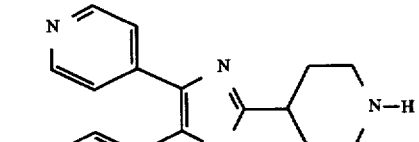 |
| 6 |  |
| 7 | 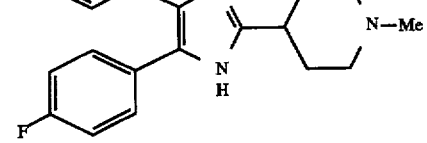 |
| 8 | 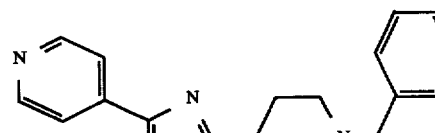 |
| 9 | 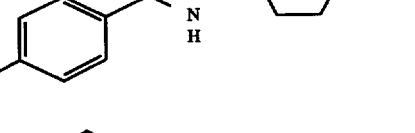 |

-continued

| No. | Compound |
|-----|----------|
| 10 | |
| 11 | |
| 12 | |
| 13 | |
| 14 | |

-continued
| No. | Compound |
|---|---|
| 15 | 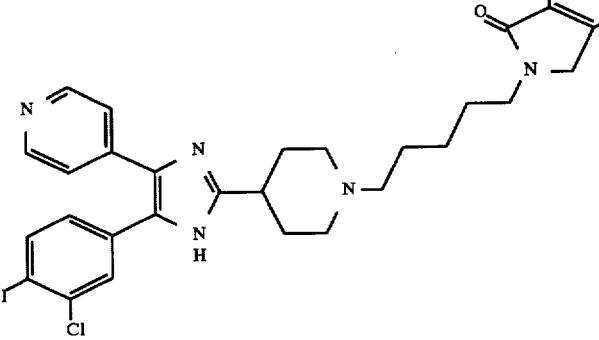 |
| 16 | 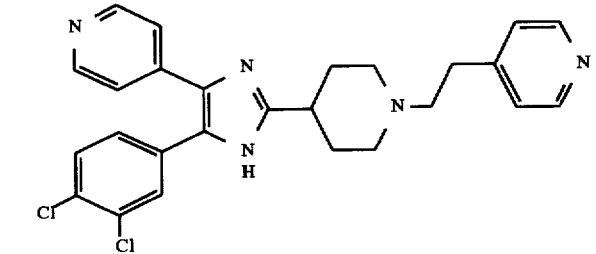 |
| 17 | 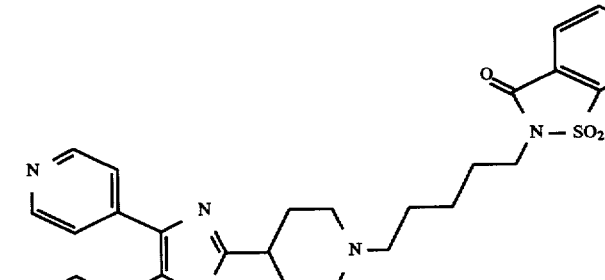 |
| 18 | 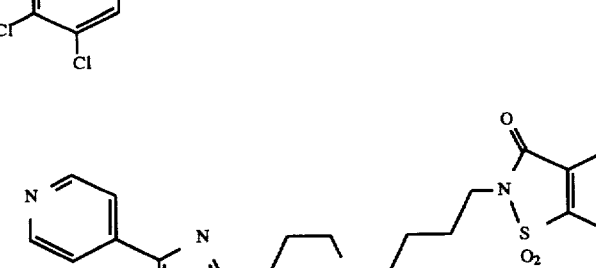 |

-continued

| No. | Compound |
|---|---|
| 19 | 4-(pyridin-4-yl)-5-(3-hydroxyphenyl)-2-(1-methylpiperidin-4-yl)-1H-imidazole |
| 20 | 4-(pyridin-4-yl)-5-(4-fluorophenyl)-2-(piperidin-3-yl)-1H-imidazole |
| 21 | 4-(pyridin-4-yl)-5-(4-fluorophenyl)-2-(1-methylpiperidin-3-yl)-1H-imidazole |
| 22 | 4-(pyridin-4-yl)-5-(4-fluorophenyl)-2-(4-methyl-1-methylpiperidin-4-yl)-1H-imidazole |
| 23 | 4-(pyridin-4-yl)-5-(4-fluorophenyl)-2-(4-benzylpiperidin-4-yl)-1H-imidazole |
| 24 | 4-(pyridin-4-yl)-5-(3,4-dichlorophenyl)-2-[1-(glycyl)piperidin-4-yl]-1H-imidazole |

| No. | Compound |
|---|---|
| 25 | [structure: 4-pyridyl and 4-fluorophenyl substituted imidazole linked to piperidine with NH] |
| 26 | [structure: 4-pyridyl and 4-fluorophenyl substituted imidazole linked to N-acetyl piperidine] |
| 27 | [structure: 3-CF3-phenyl and 3-pyridyl substituted imidazole with N-propyl, linked to piperidine NH] |
| 28 | [structure: (phenylethylamino)pyridyl, N-methyl imidazole with 3-CF3-phenyl, linked to piperidine NH] | as well as pharmaceutically acceptable salts thereof.

Further examples of compounds of the present invention are as follows:

4-[5-(3,4-dichlorophenyl)-4-pyridin-4-yl-1H-imidazol-2-yl] piperidine-1-carboxylic acid benzyl ester;

4-[5-(3-methoxyphenyl)-4-pyridin-4-yl-1H-imidazol-2-yl] piperidine-1-carboxylic acid tert-butyl ester;

4-[5-(4-fluorophenyl)-4-pyridin-4-yl-1H-imidazol-2-yl]-4-methylpiperidine-1-carboxylic acid tert-butyl ester;

4-[1-propyl-5-pyridin-4-yl-4-(3-trifluoromethylphenyl)-1H-imidazol-2-yl]piperidine-1-carboxylic acid benzyl ester;

4-[1-hydroxy-5-(2-fluoropyridin-4-y 1)-4-(3-trifluoromethylphenyl)imidazol-2-yl]piperidine-1-carboxylic acid benzyl ester;

4-[5-(2-fluoropyridin-4-yl)-4-(3-trifluoromethylphenyl)-1H-imidazol-2-yl]piperidine-1-carboxylic acid benzyl ester;

4-[5-(2-fluoropyridin-4-yl)-1-methyl-4-(3-trifluoromethylphenyl)-1H-imidazol-2-yl]-piperidine-1-carboxylic acid benzyl ester and (S)-4-[5-(2-(1-Phenylethylamino)pyridin-4-yl)-1-methyl-4-(3-trifluoromethylphenyl)-1H-imidazol-2-yl]-piperidine-1-carboxylic acid benzyl ester.

The compounds of the present invention are prepared by procedures illustrated in the accompanying schemes. The two general methods for preparation of the imidazole nucleus are outlined in schemes 1 and 2. In the first method a suitably protected picolyl alcohol is deprotonated with a strong base such as n-butyl lithium or lithium diisopropyl amide and the resulting anion is reacted with an appropriate N,O-Dimethylhydroxamide to give a protected alpha hydroxy ketone. The protected alpha hydroxy ketone is then condensed with a suitably functionalized and protected aminoaldehyde in the presence of ammonium acetate, acetic acid and copper acetate. The aldehydes used in the present examples all contain a suitably protected nitrogen atom. After the imidazole nucleus has been formed, the nitrogen is deprotected and then reacted with an appropriate electrophilic reagent to provide the final compounds.

In the second method, a suitably protected picolyl alcohol is deprotonated with a strong base such as n-butyl lithium or lithium diisopropyl amide and the resulting anion is reacted with an appropriate aryl or alkyl aldehyde to give a monoprotected diol. The protecting group is removed and the resulting diol is oxidized (by the method of Swern or Moffat) to a dione. The dione is then condensed with a suitably functionalized and protected aminoaldehyde in the presence of ammonium acetate in acetic acid to give the imidazole.

In this same manner, the nitrogen is deprotected and then reacted with an appropriate electrophilic reagent to provide the compounds of formula I.

An additional method of preparing compounds described in this invention is shown in Scheme 6. The anion of 4-dimethoxymethylpyridine is formed with a strong base such as n-butyllithium and quenched with an electrophile e.g. an appropriately substituted benzyl halide. The ketal is then hydrolysed under acidic conditions and an oxime group introduced by treatment with an appropriate alkyl or metal nitrite under acidic conditions. The oximinoketone may then be condensed with a suitably protected heterocyclic aldehyde and an amine to provide an imidazole-N-oxide. Reduction to the corresponding imidazole may then be accomplished under a variety of conditions e.g titanium (III) chloride. Deprotection then affords the desired compounds.

A further method of preparation of compounds of the present invention is outlined in Scheme 7. The anion of 2-fluoro-4-methylpyridine is formed with strong base such as lithium diisopropylamide and quenched with an appropriately substituted N-methoxy-O-methoxy amide to provide a ketone. An oximino group can then be introduced for example by treatment with an alkyl nitrite under acidic conditions. Condensation with an appropriately protected heterocyclic aldehyde and ammonium acetate in acetic acid affords, after reduction an imidazole. The fluoropyridine substituent can then be displaced by a nucleophile e.g. a primary or secondary amine to give a substituted pyridine, which may be deprotected.

Scheme 1

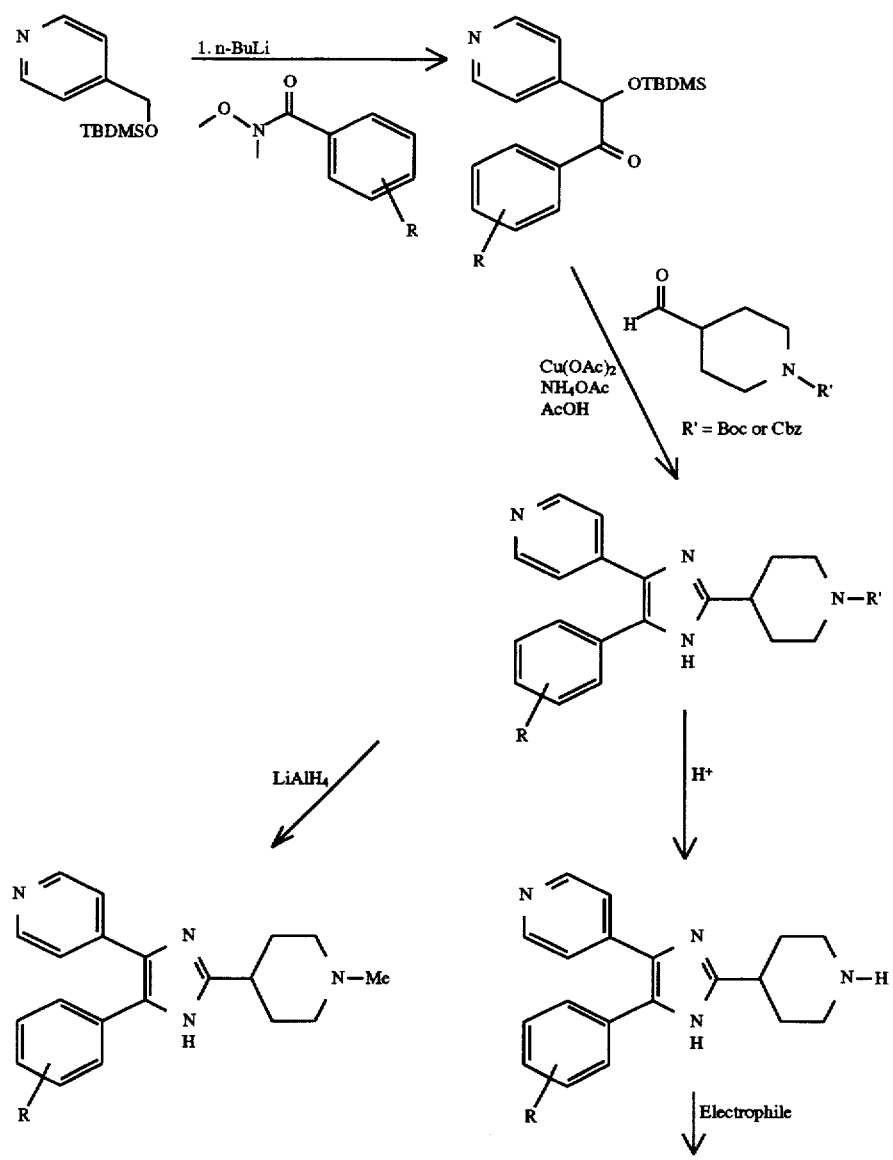

-continued
Scheme 1
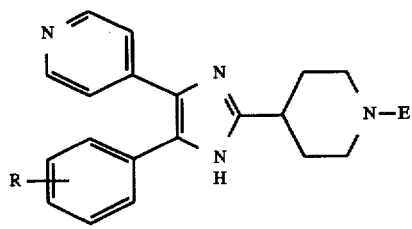
Scheme 2
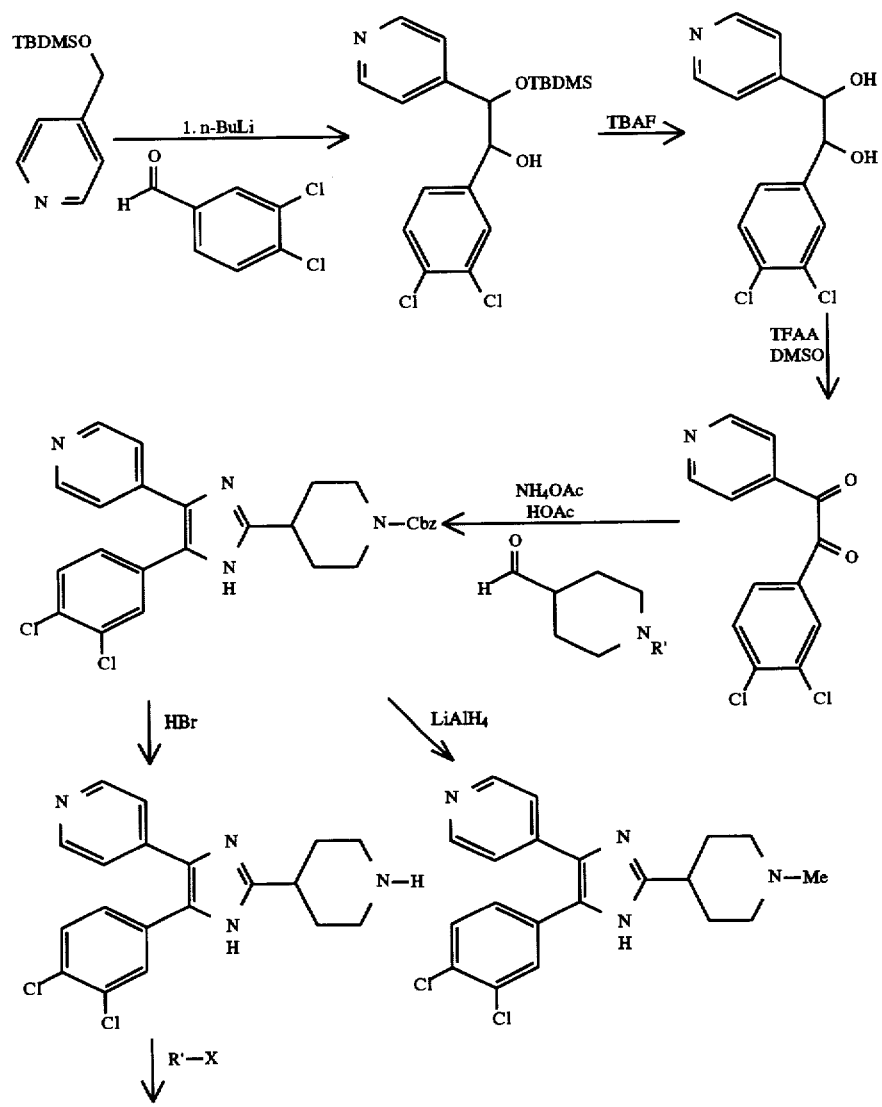

-continued
Scheme 2
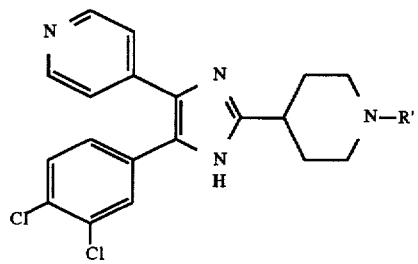
Scheme 3
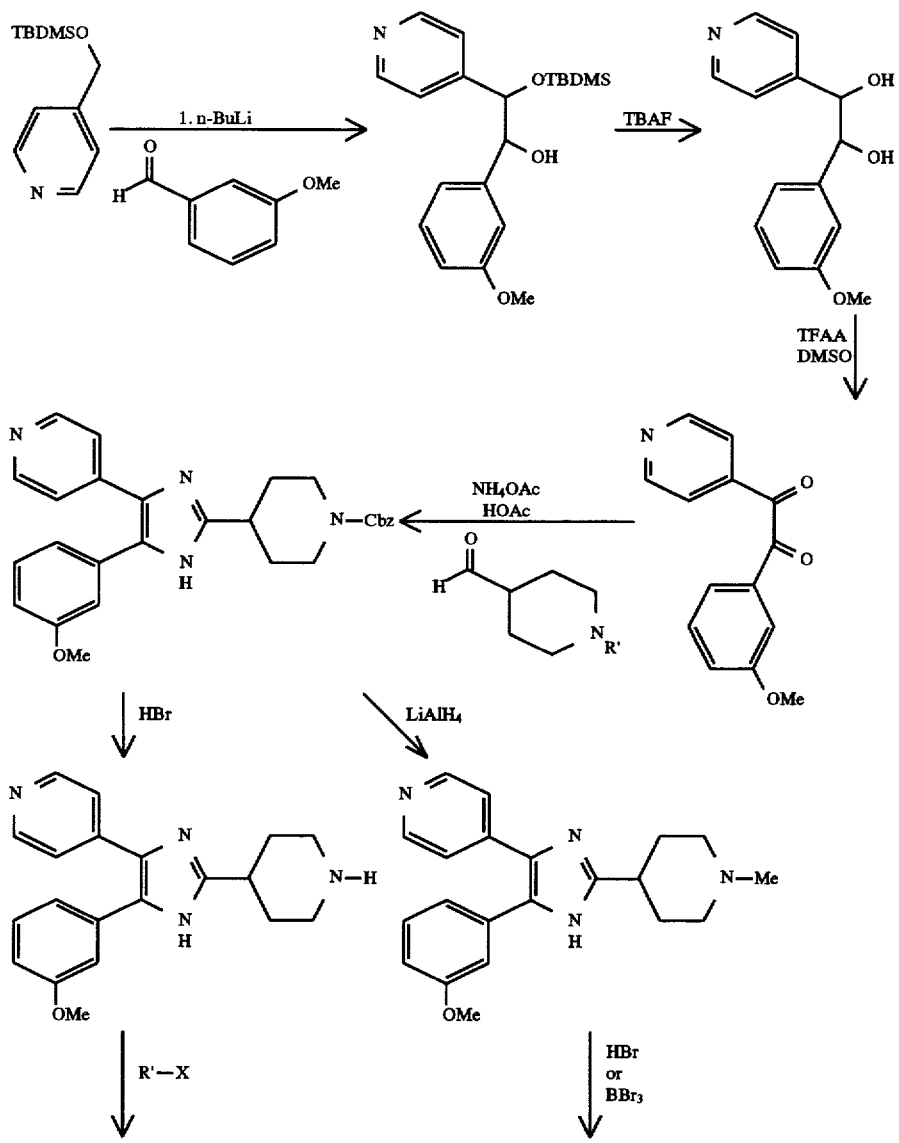

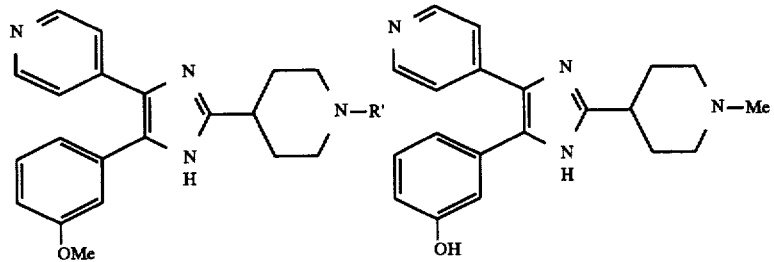
-continued
Scheme 3
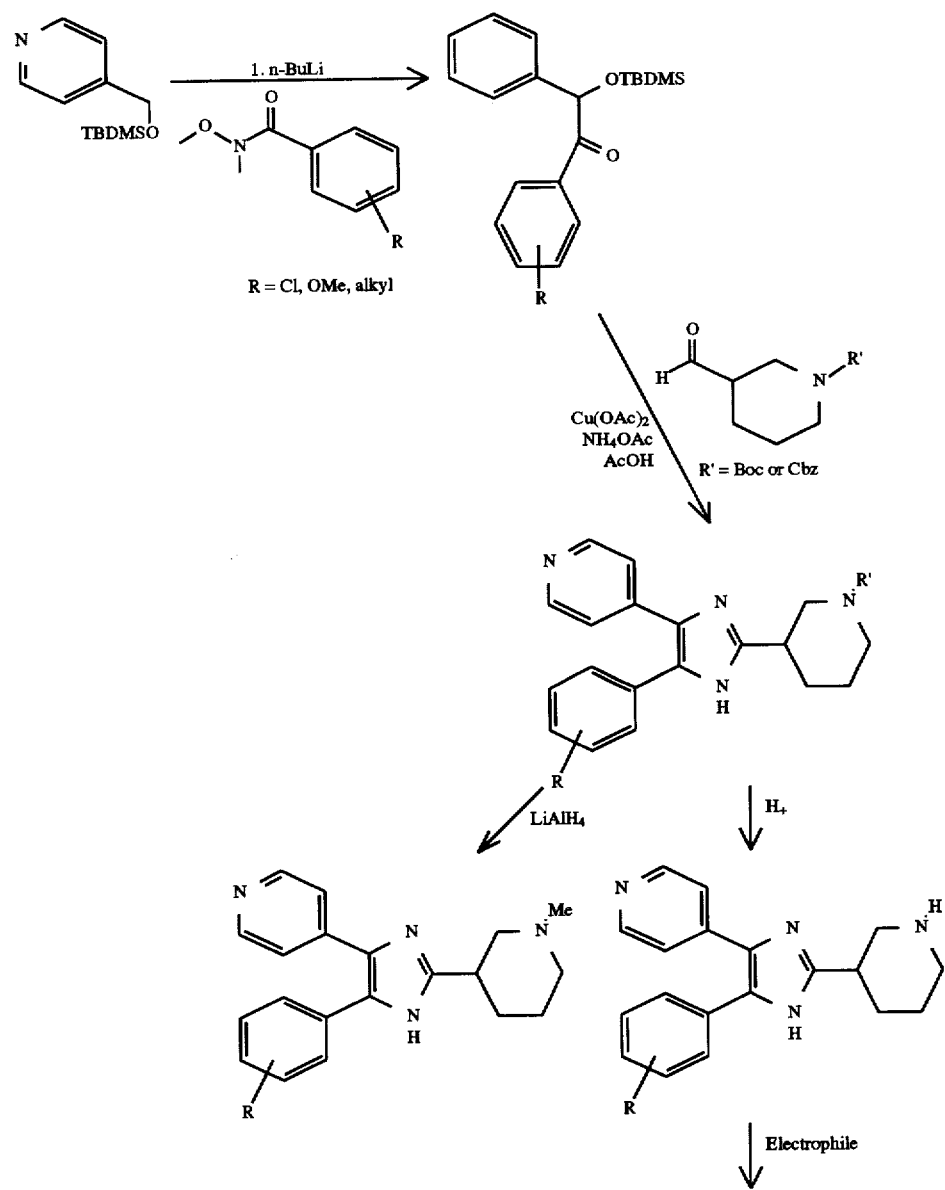
Scheme 4

-continued
Scheme 4
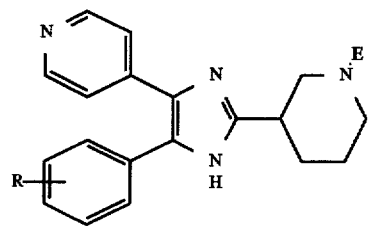
Scheme 5
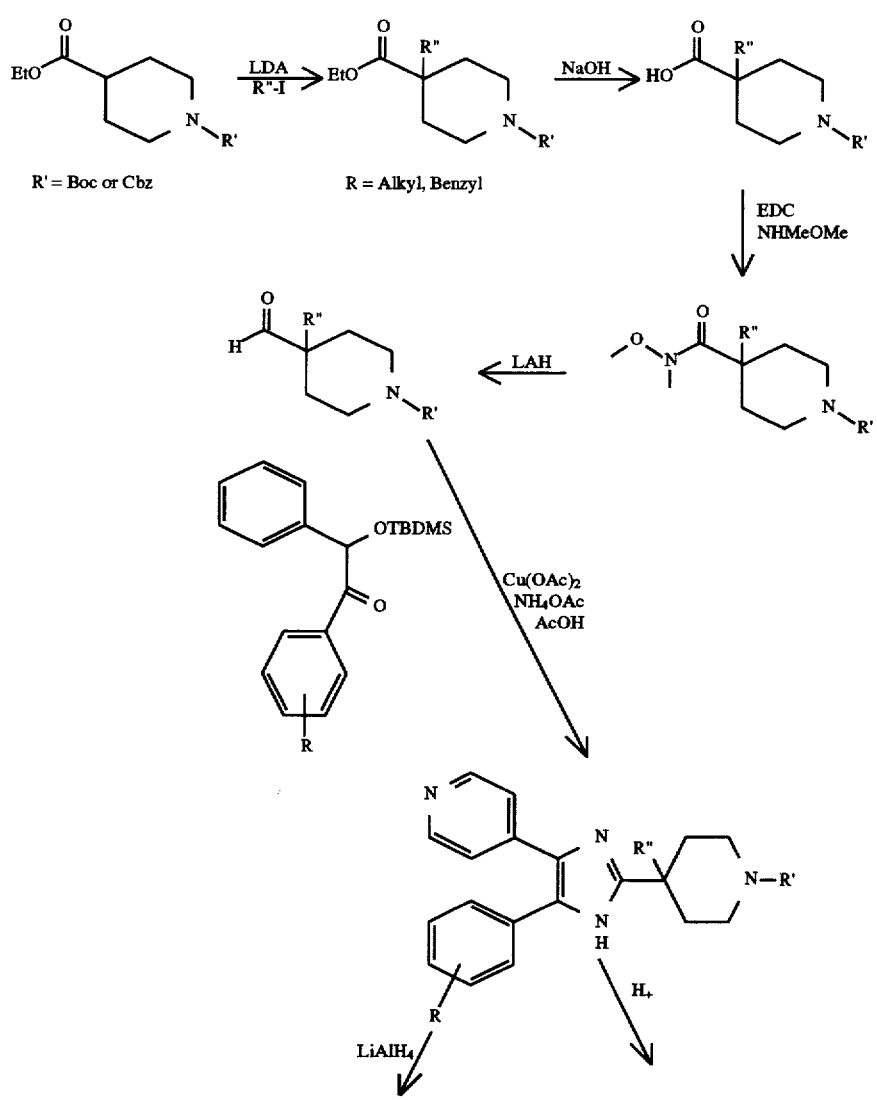
R' = Boc or Cbz
R = Alkyl, Benzyl -continued
Scheme 5
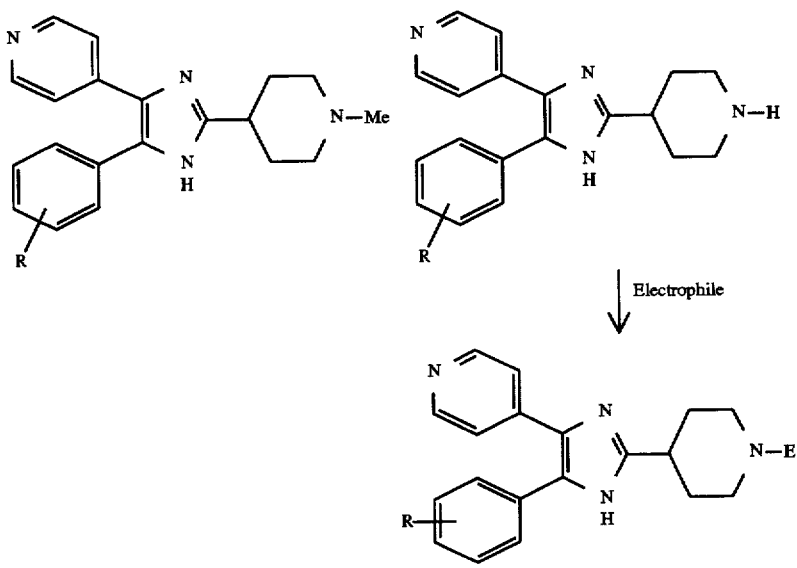
Scheme 6
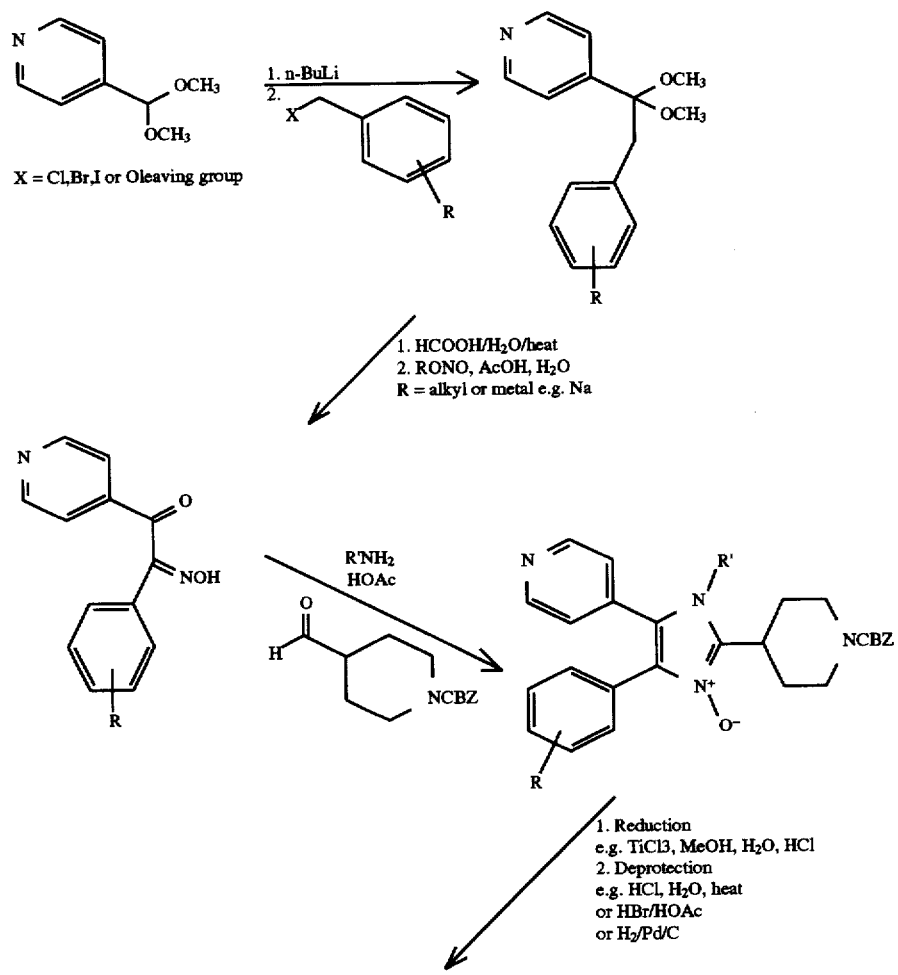

-continued
Scheme 6
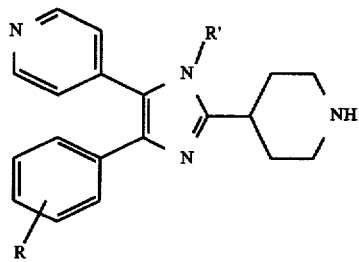
Scheme 7
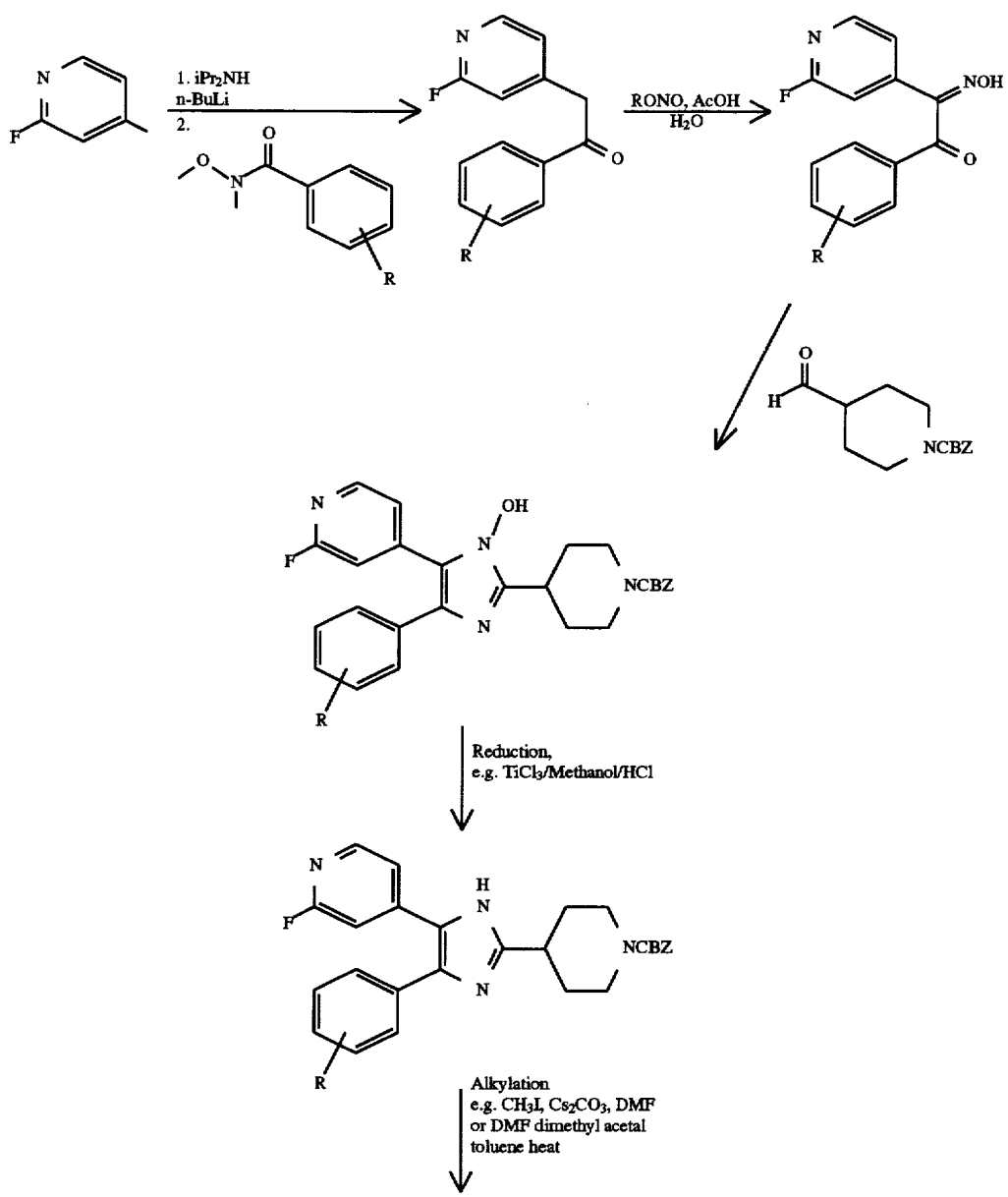

-continued
Scheme 7

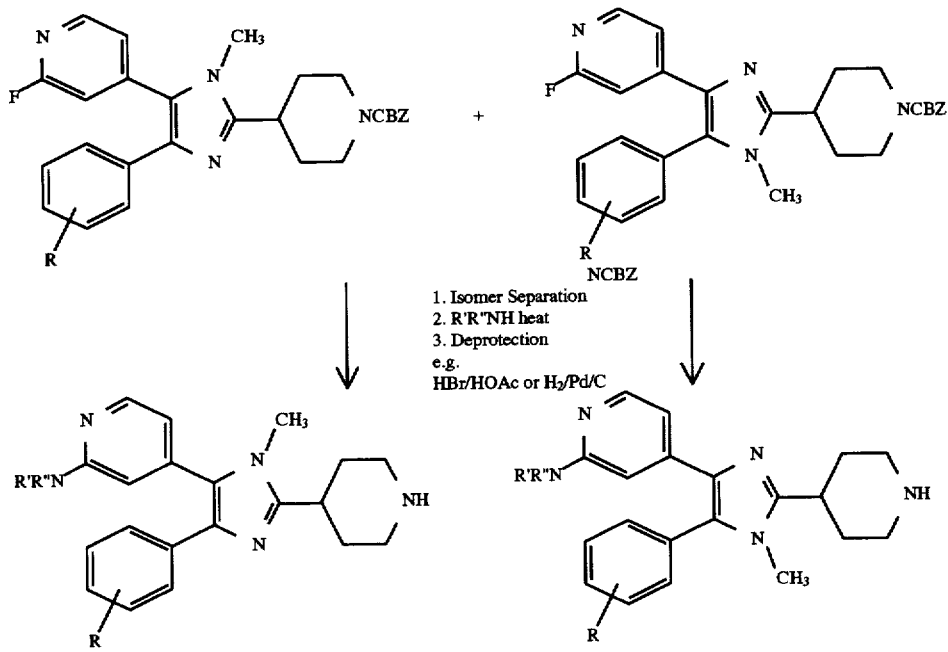

As used in the above schemes, TBDMSO refers to t-butyldimethylsilyloxy, TFAA refers to trifluoroacetic anhydride, TBDMS refers to t-butyldimethylsilyl, TBAF refers to tetrabutyl ammonium fluoride, Cbz refers to carboxylbenzyl, Ac refers to acetyl, LDA refers to lithium diisopropyl amide and EDC refers to ethyl dimethylaminopropyl carbodiimide.

E represents an electrophile attached to the heterocyclic ring nitrogen atom. Examples of suitable electrophiles include alkyl halides, alkyl triflates, alkyl mesylates, benzyl halides, vinyl pyridine and the like. Hence, E represents alkyl, benzyl, pyridylethyl and the like.

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

The pharmaceutically acceptable salts of the compounds of formula I include conventional non-toxic salts or quarternary ammonium salts of the compounds of formula I formed e.g. from non-toxic inorganic or organic acids. For example, non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, trifluoroacetic and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The compounds of the present invention may have asymmetric centers and occur as racemates, racemic mixtures, and as individual diastereomers. All such isomers, including optical isomers, being included in the present invention.

The invention described herein also includes a pharmaceutical composition which is comprised of a compound as described herein in combination with a pharmaceutically acceptable carrier.

The invention described herein also includes a method of treating cancer which is comprised of administering to a mammalian patient in need of such treatment a compound as described herein in an amount which is effective to treat cancer.

The invention described herein also includes a method of treating a cytokine mediated disease in a mammal, comprising administering to a mammalian patient in need of such treatment an amount of a compound as described herein in an amount which is effective to treat said cytokine mediated disease.

Of particular interest is a method of treating inflammation in a mammalian patient in need of such treatment, which is comprised of administering to said patient an anti-inflammatory effective amount of a compound as described herein.

Another method which is of particular interest is a method of treating a cytokine mediated disease as described herein wherein the disease is osteoporosis.

Another method which is of particular interest is a method of treating a cytokine mediated disease as described herein wherein the disease is non-osteoporotic bone resorption.

Yet another method which is of particular interest is a method of treating a cytokine mediated disease as described herein wherein the disease is Crohn's disease.

This invention also relates to a method of inhibiting cancer in a mammal in need such treatment, which comprises administering to said mammal an amount of a compound of formula I which is effective for treating cancer. Such method includes the treatment of cancer of the brain, genitourinary tract, lymphatic system, stomach, larynx and lung. Additionally, such method includes the treatment of histiocytic lymphoma, lung adenocarcinoma and small cell lung cancers.

When administered to a patient for the treatment of cancer, the dosage used can be varied depending upon the type of cancer, the age and general condition of the patient, the particular compound administered, the presence or level of toxicity or adverse effects experienced with the drag, and other factors. A representative example of a suitable dosage range is from as low as about 0.01 mg/kg to as high as about 100 mg/kg. However, the dosage administered is generally left to the discretion of the physician.

This invention also relates to a method of inhibiting a cytokine or cytokines in a mammal in need thereof, which comprises administering to said mammal an effective amount of a compound of formula I to inhibit said cytokine or cytokines, down to normal levels, or in some cases to subnormal levels, so as to ameliorate, prevent or treat the disease state.

The compounds of formula 1 can be used in the prophylactic or therapeutic treatment of disease states in mammals which are exacerbated or caused by excessive or unregulated cytokines, more specifically IL-1, IL-6, IL-8 or TNF.

Because the compounds of formula I inhibit cytokines, such as IL-1, IL-6, IL-8 and TNF, the compounds are useful for treating diseases in which cytokine presence or activity is implicated, such as rheumatoid arthritis, rheumatoid spondylitis, osteoarthritis, gouty arthritis and other arthritic conditions.

The compounds of formula I are also useful to treat other disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds of formula I are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds of formula I are also useful in treating diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound of formula I in an amount which is effective for treating said disease or condition.

When administered to a patient for the treatment of a disease in which a cytokine or cytokines are implicated, the dosage used can be varied depending upon the type of disease, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

The methods of treatment are preferably carried out by delivering the compound of formula I parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of formula I subcutaneously, intranasally, intrarectally, transdermally or intravaginally.

The compounds of formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

EXAMPLE 1

4-[5-(4-FLUOROPHENYL)-4-PYRIDIN-4-YL-1H-IMIDAZOL-2-YL]-PIPERIDINE-1-CARBOXYLIC ACID TERT-BUTYL ESTER

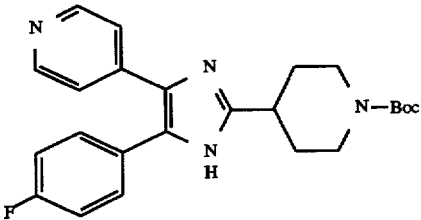

Step 1-A 1-(4-Fluorophenyl)-2-hydroxy-2-pyridin-4-yl-ethanone tert-butyldimethylsilyl ether To a stirring solution of diisopropyl amine (0.42 mol, 42.5 g) in THF (400 mL) cooled to −78° C. was added n-butyl lithium (0.42 mol, 263 mL of a 1.6M solution in hexanes). The reaction was warmed to −20° C. and 4-pyridyl carbinol tert-butyldimethylsilyl ether (0.32 mol, 67.0 g) was added in THF (100 mL). The reaction was stirred at −20° C. for 0.5 h. and the 4-fluorophenyl-N,O-dimethyl benzhydroxamide was added and the solution was stirred at −20° C. for 0.5 h. The reaction was diluted with 1 L saturated aqueous sodium hydrogen carbonate, the phases were separated and the aqueous layer was extracted with ethyl acetate (2×200mL). The combined organic layers were washed with brine, dried over anhydrous sodium sulfate and evaporated under reduced pressure. The residue was chromatographed over silica, eluting with 20% EtOAc:Hexanes. The pure fractions were combined and evaporated under reduced pressure to give 74.65 g of a pale orange oil.

$^1$H NMR (CDC$_{13}$) d 8.59 (d,J=6.1 Hz,2H), 8.03 (dd,J=8.8 and 5.5 Hz,2H), 7.45 (d,J=5.6 Hz,2H), 7.00 (t,J=8.5 Hz, 1H), 5.60 (s, 1H), 0.899 (s,9H), 0.112 (s,3H), −0.011 (s,3H)

Step 1-B

4-[5-(4-Fluorophenyl)-4-pyridin-4-yl-1H-imidazol-2-yl]-piperidine-1-carboxylic acid tert-butyl ester To a stirring solution of 1-(4-fluorophenyl)-2-hydroxy-2-pyridin-4-yl-5 ethanone tert-butyldimethylsilyl ether (1.5 mmol, 0.5 g) in acetic acid (10 mL) was added N-tert-butoxycarbonyl-4-piperidine carbaldehyde (1.7 mmol, 0.35 g), ammonium acetate (15.0 mmol, 1.15 g), and copper acetate (3.0 mmol, 0.54 g). The reaction was heated to reflux for 1 h. The reaction was then poured into ice cold 30% aqueous ammonium hydroxide (100 mL) and ethyl acetate (50 mL) and this was stirred for 0.5 h. The phases were separated and the aqueous was extracted with ethyl acetate (50 mL). The organic layers were combined, washed with brine, dried over anhydrous sodium sulfate and evaporated under reduced pressure. The residue was chromatographed over silica eluting with 2.5% MeOH:CH$_2$Cl$_2$. The product containing fractions were collected and evaporated under reduced pressure. The resulting foam was crystallized from diethyl ether to give 0.28 g of the title compound as a white powder. mp=157°–160° C.

$^1$H NMR (CD$_3$OD) d 8.40 (s,2H), 7.50–7.45 (m,4H), 7.25–7.10 (m,2H), 4.21 (d,J=13.2 Hz,2H), 3.08–2.82 (m,3H), 2.05–1.90 (m,2H), 1.90–1.70 (m,2H), 1.48 (s,9H). Anal; Calcd for C$_{24}$H$_{27}$N$_2$O$_2$F.0.70H$_2$O: C 66.25, H 6.58, N 12.88; Found: C 66.31, H 6.65, N 13.05.

EXAMPLE 2

4-BENZYL-[4-(4-FLUOROPHENYL)-5-PYRIDIN-4-YL-1H-IMIDAZOL-2-YL]-PIPERIDINE-1-CARBOXYLIC ACID TERT-BUTYL ESTER

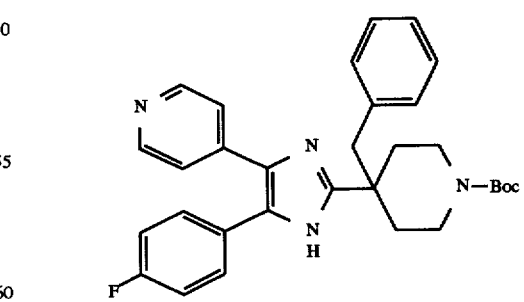

Step 2-A 4-benzylpiperidine-1,4-dicarboxylic acid tert-butyl ester ethyl ester

To a stirring solution of diisopropyl amine (38.0 mmol, 3.84 g) in THF (50 mL) cooled to −78° C. was added n-butyl lithium dropwise (41.2 mmol, 16.5 mL of a 1.6M solution in hexanes). To this was added piperidine-1,4-dicarboxylic acid tert-butyl ester ethyl ester (31.7 mmol, 8.16 g) in 20 mL THF. The reaction was allowed to stir for 5 min. and benzyl bromide (31.7 mmol, 5.42 g) was added. The reaction was then allowed to warm to room temperature. The reaction was then diluted with ethyl acetate (200 mL) and washed with 10% KHSO$_4$. The aqueous layers were extracted with ethyl acetate (100 mL). The organics were combined, washed with brine and dried over anhydrous sodium sulfate. The solution was filtered and evaporated under reduced pressure to give 12.13 g of the title compound as a yellow oil.

$^1$H NMR (CDCl$_3$) d 7.30–7.18 (m,3H), 7.05–7.00 (m,2H), 4.09 (q,J=6.9 Hz,2H), 4.02–3.85 (m,2H), 2.90–2.70 (m,4H), 2.15–2.02 (m,2H), 1.50–1.35 (m,3H), 1.44 (s,9H), 1.18 (t,J=6.9 Hz,3H)..

Step 2-B 4-benzylpiperidine-1,4-dicarboxylic acid tert-butyl ester

To a stirring solution of 4-benzylpiperidine-1,4-dicarboxylic acid tert-butyl ester ethyl ester (31.6 mmol, 11.01 g) in isopropyl alcohol (50 mL) and THF (50 mL) was added 3N NaOH (63.4 mmol, 21.1 mL) and the biphasic solution was heated to reflux. The reaction was heated for 8 h. and then left stirring at room temperature overnight. The reaction was then diluted with water (200 mL) and acidified to pH=4 with glacial acetic acid. The aqueous mixture was then extracted with ethyl acetate (2×500 mL). The organic layers were combined, washed with brine, dried over anhydrous sodium sulfate, and evaporated under reduced pressure. The resulting solid was triturated with diethyl ether to give 6.7 g of a white solid.

$^1$H NMR (CDCl$_3$) d 7.30–7.18 (m,3H), 7.05–7.00 (m,2H), 4.02–3.85 (m,2H), 2.90–2.70 (m,4H), 2.12–2.02 (m,2H), 1.50–1.35 (m,2H), 1.44 (s,9H).

Step 2-C 4-(methoxymethylcarbamoyl)piperidine-1-carboxylic acid tert-butyl ester To a stirring solution of 4-benzylpiperidine-1,4-dicarboxylic acid tert-butyl ester (12.5 mmol, 4.0 g) in THF (60 mL) was added thionyl chloride (13.8 mmol, 1.64 g) and pyridine (0.2 mL). The reaction was stirred at r.t. for 1 h. The reaction was then evaporated under reduced pressure and the residue taken up in CH$_2$Cl$_2$ (50 mL). To this solution was added N,O-Dimethylhydroxylamine hydrochloride (13.8 mmol, 1.35 g) and triethylamine (25.0 mmol, 2.53 g). The reaction was stirred at room temperature for 1 h. The reaction was then diluted with CH$_2$Cl$_2$ (100 mL) and washed with 10% KHSO$_4$. (100 mL) and saturated sodium bicarbonate (100 mL). The organic layers were washed with brine, dried over anhydrous sodium sulfate and evaporated under reduced pressure. The residue was evaporated from ethyl ether:hexanes to give 4.14 g of the title compound as a white solid.

$^1$H NMR (CDCl$_3$) d 7.30–7.18 (m,3H), 7.14–7.00 (m,2H), 4.02–3.75 (m,2H), 3.66(s,3H), 3.20 (s,3H)$_{3.12-2.85}$ (m,4H), 2.30–2.15 (m,2H), 1.50–1.35 (m,2H), 1.44 (s,9H).

Step 2-D 2-(tert-butyldimethylsilyloxy)1-4-fluorophenyl)2-pyridin-4-yl-ethanone

To a stirring solution of 4-(methoxymethyl-carbamoyl)piperidine-1-carboxylic acid tert-butyl ester (1.0 g, 2.8 mmol) in THF (10 mL) was added lithium aluminum hydride (2.8 mmol, 2.8 mL of a 1M solution in THF). The reaction was stirred at r.t. for 0.5 h. The reaction was then quenched with water (2 mL) and diluted with ethyl acetate (50 mL). The reaction was filtered, the filtrates washed with 10% KHSO$_4$. (50 mL), brine, dried over anhydrous sodium sulfate and the solvent evaporated under reduced pressure to give 0.82 compound title compound as a colorless oil.

$^1$H NMR (CDC$_{13}$) d 9.56 (s,1H), 7.40–7.14 (m,3H), 7.06–6.98 (m,2H), 4.02–3.75 (m,2H), 2.90–2.68 (m,2H), 2.80 (s,2H)$_{2.00-1.85}$ (m,2H), 1.50–1.35 (m,2H), 1.44 (s,9H).

Step 2-E

4-Benzyl-4-[4-(4-fluorophenyl-5-pyridin-4-yl-1H-imidazol-2-yl]piperidine-1-carboxylic acid tert-butyl ester To a stirring solution of 2-(tert-butyldimethyl-silyloxy)-1-(4-fluorophenyl)-2-pyridin-4-yl-ethanone (2.4 mmol, 0.80 g) in acetic acid (10 mL) was added 4-benzyl-4-formylpiperidine-1-carboxylic acid tert-butyl ester (2.7 mmol, 0.82 g), ammonium acetate (24.0 mmol, 1.84 g), and copper acetate (4.8 mmol, 0.87 g). This was heated to reflux for 1 h. The reaction was then poured into ice cold 30% aqueous ammonium hydroxide (200 mL) and stirred for 0.5 h. The phases were separated and the aqueous was extracted with ethyl acetate (2×100 mL). The organic layers were combined, washed with brine, dried over anhydrous sodium sulfate, and the solvent evaporated under reduced pressure. The residue was chromatographed over silica eluting with 3% MeOH:CH$_2$Cl$_2$. The product containing fractions were collected and evaporated under reduced pressure to give an off white solid. This was chromatographed over silica eluting with 1% MeOH:EtOAc. The pure fractions were collected and evaporated under reduced pressure to give 133 mg of the title compound as an off white foam.

$^1$H NMR (CD$_3$OD) d 8.45–8.35 (m,2H), 7.95–7.88 (m, 1H), 7.60–7.10 (m,9H), 6.70–6.60 (m,2H), 4.02–3.80 (m,2H), 2.96 (s,2H), 3.00–2.80 (m,2H), 2.40 (d,J=13.9 Hz,2H), 1.82–1.65 (m,2H), 1.44 (s,9H).

EXAMPLE 3

3-[5-(4-FLUOROPHENYL)-4-PYRIDIN-4-YL-1H-IMIDAZOL-2-YL]PIPERIDINE-1-CARBOXYLIC ACID TERT-BUTYL ESTER

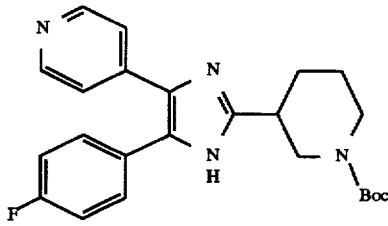

Step 3-A

N-tert-butoxycarbonyl-3-piperidinecarboxylic acid

To a stirring solution of nipecotic acid (38.7 mmol,5 g) in 1,4-dioxane (20 mL) was added 1N NaOH (4.6 mmol, 4.6 mL) and di-tert-butyl dicarbonate (38.7 mmol, 8.45 g). The reaction was stirred for 2 h at room temperature. The reaction was diluted with 10% KHSO$_4$ (50 mL) and extracted with ethyl acetate (2×100 mL). The combined organics were washed with brine, dried over anhydrous sodium sulfate and the solvent evaporated under reduced pressure to give 8.53 g of the title compound as a white powder.

¹H NMR (CDCl₃) d 4.25–4.00 (m,1H), 3.95–3.85 (m, 1H), 3.15–2.92(m, 1H), 2.92–2.78 (m, 1H), 2.55–2.42 (m, 1H), 2.14–2.00 (m, 1H), 1.78–1.55 (m,2H), 1.55–1.35 (m, 1H)₁.₄₅ (s,9H)

Step 3-B

N-tert-butoxycarbonyl-3-piperidine-N-methoxy-N-methyl carboxamide

To a stirring solution of N-tert-butoxycarbonyl-3-piperidinecarboxylic acid (17.4 mmol, 4.0 g) in THF (50 mL) was added thionyl chloride (19.2 mmol, 2.28 g) and pyridine (0.1 mL). The reaction was stirred for 2 h at room temperature, evaporated under reduced pressure and the residue taken up in methylene chloride (10 mL) and added dropwise to a stirring suspension of N,O-dimethylhydroxylamine hydrochloride (17.4 mmol, 1.69 g). Triethylamine (34.8 mmol, 3.52 g) was then added and the reaction was stirred at room temperature for 1 h. The reaction was then diluted with methylene chloride (50 mL) and washed with 10% KHSO₄ (50 mL), saturated sodium bicarbonate (50 mL) and brine, dried over anhydrous sodium sulfate and the solvent evaporated under reduced pressure to give 4.14 g of the title compound as a pale yellow oil.

¹H NMR (CDCl₃) d 4.25–3.95 (m,2H), 3.72 (s,3H), 3.18 (s,3H), 2.95–2.58 (m,3H), 1.95–1.85 (m, 1H), 1.75–1.55 (m,2H), 1.45 (s,9H).

Step 3-C

N-tert-butoxycarbonyl-3-piperidinecarboxaldehyde

To a stirring solution of the N-tert-butoxycarbonyl-3-piperidine-N-methoxy-N-methyl carboxamide (14.8 mmol, 4.03 g) in THF (40 mL) cooled in ice was added lithium aluminum hydride (14.8 mmol, 14.8 mL of a 1M solution in THF). The reaction was stirred for 0.5 h. and then quenched with water (3 mL). The reaction was diluted with ethyl acetate (100 mL), filtered, and the filtrates washed with 10% KHSO₄ (50 mL), dried over anhydrous sodium sulfate and evaporated under reduced pressure to give 2.54 g of the title compound as a colorless oil.

¹H NMR (CDCl₃) d 9.69 (s, 1H), 4.00–3.85 (m, 1H), 3.70–3.55 (m,1H), 3.31 (dd,J=13.4 and 8.3 Hz, 1H), 3.14–3.02 (m, 1H), 2.48–2.35 (m, 1H), 2.00–1.88 (m, 1H), 1.75–1.56 (m,2H), 1.56–1.40 (m, 1 H)₁.₄₅ (s,9H)

Step 3-D

3-[5-(4-Fluorophenyl-4-pyridin-4-yl-1H-imidazol-2-yl-]piperidine-1-carboxylic acid ester To a stirring solution of the 1-(4-fluorophenyl)-2-hydroxy-2-pyridin-4-ylethanone tert-butyldimethylsilyl ether (11.9 mmol, 3.42 g) in acetic acid (40 mL) was added N-tert-butoxycarbonyl-3-piperidine carboxaldehyde (11.9 mmol, 2.54 g), ammonium acetate (0.12 mol, 9.25 g), and copper acetate (23.8 mmol, 4.32 g). The reaction was heated to reflux for 1 h. The reaction was poured into ice cold 30% aqueous ammonium hydroxide (500 mL) and stirred for 0.5 h. The resulting suspension was extracted with ethyl acetate (2×200 mL). The organics were combined, washed with brine, dried over anhydrous sodium sulfate and the solvent evaporated under reduced pressure. The residue was chromatographed over silica eluting with 3% MeOH:CH₂Cl₂. The pure fractions were collected and evaporated under reduced pressure. The resulting solid was triturated with diethyl ether to give 1.75 g of the title compound as a white powder. mp=193°–194° C.

¹H NMR (CDCl₃) d 8.40 (s,2H)₇.₅₅₋₇.₄₀ (m,4H), 7.25–7.10 (m,2H), 4.26 (d,J=10.7 Hz, 1H), 4.07 (d,J=13.4 Hz, 1H), 3.22–3.12 (m, 1H), 3.00–2.70 (m,2H), 2.20–2.08 (m, 1H), 2.00–1.75 (m,2H), 1.70–1.45 (m, 1 H) 1.46 (s,9H). Anal; Calcd for C₂₄H₂₇N₄O₂F.0.20H₂O: C 67.65, H 6.48, N 13.15; Found: C 67.64, H 6.33, N 13.02.

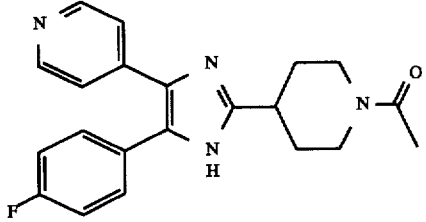

EXAMPLE 4

4-[5-(4-FLUOROPHENYL)-4-PYRIDIN-4-YL-1H-IMIDAZOL-2-YL]-1-ACETYLPIPERIDINE

To a stirring solution of 4-[5-(4-fluorophenyl)-4-pyridin-4-yl-1H-imidazol-2-yl]piperidine (0.76 mmol,0.30 g) in THF (5 mL) was added triethylamine (2.7 mmol,0.27 g) and acetyl chloride (0.91 mmol,71.5 mg) and the reaction stirred at room temperature overnight. The reaction was diluted with water (50 mL) and saturated sodium bicarbonate (10 mL) and the aqueous phase extracted with ethyl acetate (2×50 mL). The combined organic layers were dried over anhydrous sodium sulfate, and the solvent evaporated under reduced pressure. The residue was chromatographed over silica, eluting with 2.5% to 5% MeOH:CH₂Cl₂. The product containing fractions were combined and evaporated to give a yellow oil. This oil was crystallized from diethyl ether to give 75 mg of the title compound as a white powder. mp=235°–6° C.

¹H NMR (CDC₁₃) d 8.39 (d,J=6.1 Hz,2H), 7.50–7.40 (m,4H), 7.18 (t,J=8.8 Hz,2H), 5.70–5.60 (m, 1H), 4.12–4.02 (m,1H), 3.20–3.05 (m, 1H), 2.72–2.85 (m, 1H), 2.15 (s,3H), 2.15–2.00 (m,2H), 1.98–1.75 (m,3H). Anal; Calcd for C₂₁H₂₁N₄OF.0.45H₂O: C 67.71, H 5.93, N 15.04; Found: C 67.75, H 5.89, N 14.96.

EXAMPLE 5

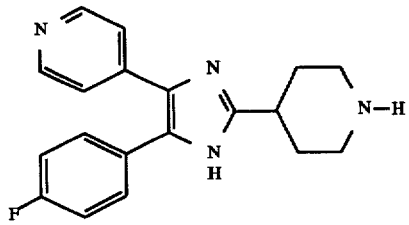

Hydrogen chloride gas was bubbled through a stirred solution of 4-[5-(4-fluorophenyl)-4-pyridin-4-yl-1H-imidazol-2-yl]-piperidine-1-carboxylic acid tert-butyl ester (0.36 mmol,0.15 g) in ethyl acetate (5 mL) for 0.5 h. The solvent was then evaporated under reduced pressure and the residue diluted with saturated sodium bicarbonate (50 mL). The resulting suspension was extracted with methylene chloride (5×20 mL), the organic layers combined, washed with brine, dried over anhydrous sodium sulfate and the solvent evaporated under reduced pressure. The resulting material was crystallized from diethyl ether to give 30 mg of the title compound as a white powder. mp=267–270° C.

¹H NMR (CD₃OD) d 8.40 (d,J=6.2,2H), 7.50–7.41 (m,4H), 7.18 (t,J=8.8 Hz,2H), 3.22–3.12 (m,2H), 3.04–2.92

(m,1H), 2.80–2.68 (m,2H), 2.05–1.95 (m,2H), 1.90–1.75 (m,2H). Anal; Calcd for C₁₉H₁₉N₄F.0.40H₂O: C 69.24, H 6.06, N 17.00; Found: C 69.23, H 5.81, N 16.74.

EXAMPLE 6

4-[5-(4-FLUOROPHENYL)-4-PYRIDIN-4-YL-1H-IMIDAZOL-2-YL]-1-METHYLPIPERIDINE

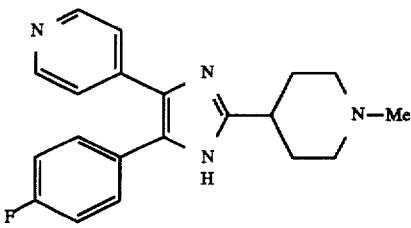

To a stirring solution of 4-[5-(4-fluorophenyl)-4-pyridin-4-yl-1H-imidazol-2-yl]piperidine-1-carboxylic acid tert-butyl ester (0.90 mmol,0.38 g) in THF (10 mL) was added lithium aluminum hydride (2.7 mmol,2.7 mL of a 1M solution in tetrahydrofuran). The reaction was heated to reflux overnight. The reaction was diluted with ethyl acetate (20 mL) and quenched with water (2.0 mL). The suspension was filtered and the filtrates dried over anhydrous sodium sulfate. The filtrates were then evaporated under reduced pressure. The resulting solid was triturated with diethyl ether, filtered and recrystallized from ethanol:diethyl ether to give 160 mg. of the title compound as a white powder. mp=259°–261° C.

¹H NMR (CDCl₃) d 8.39 (d,J=6.1 Hz,2H), 7.50–7.40 (m,4H), 7.18 (t,J=8.8 Hz,2H), 3.05–2.95 (m,2H), 2.90–2.75 (m,1H), 2.34 (s,3H), 2.25–2.10 (m,2H), 2.10–1.85 (m,4H). Anal; Calcd for C₂₀H₂₁N₄F.0.60H₂O: C 69.18, H 6.44, N 16.14; Found: C 69.18, H 6.21, N 16.33.

EXAMPLE 7

4-[5-(4-FLUOROPHENYL)-4-PYRIDIN-4-YL-1H-IMIDAZOL-2-YL]-1-BENZYL-PIPERIDINE

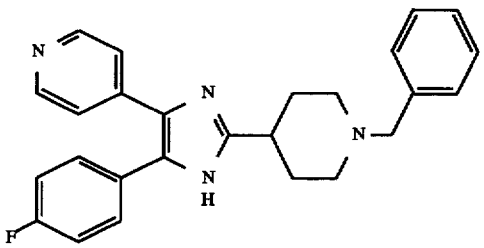

To a stirring solution of 4-[5-(4-fluorophenyl)-4-pyridin-4-yl-1H-imidazol-2-yl]piperidine (0.51 mmol, 0.20 g) in acetonitrile (4.0 mL) and methanol (2.0 mL) was added sodium bicarbonate (1.8 mmol, 0.15 g) and benzyl chloride (0.51 mmol, 64.0 mg). The reaction was heated to reflux overnight, cooled, diluted with water (50 mL) and extracted with ethyl acetate (2×50 mL). The combined organic layers were dried over anhydrous sodium sulfate and the solvent evaporated under reduced pressure. The residue was chromatographed over silica, eluting with 2.5% to 10% MeOH:CH₂Cl₂. The product containing fractions were evaporated under reduce pressure and crystallized from diethyl ether to give 74 mg of the title compound as a white powder. mp=212°–215° C.

¹H NMR (CDCl₃) d 8.39 (d,J=6.1 Hz,2H), 7.50–7.25 (m,9H), 7.18 (t,J=8.5 Hz,2H) 3.62 (s,2H), 3.12–3.02 (m,2H), 2.94–2.78 (m, 1H), 2.30–2.15 (m,2H), 2.18–1.85 (m,4H).

EXAMPLE 8

4-[5-(4-FLUOROPHENYL)-4-PYRIDIN-4-YL-1H-IMIDAZOL-2-YL]-1-ETHYLPIPERIDINE

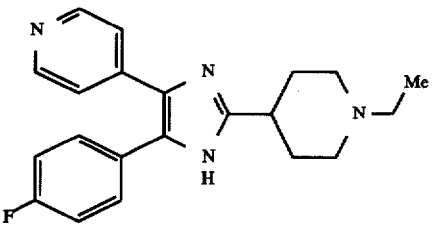

To a stirring suspension of 4-[5-(4-fluorophenyl)-4-pyridin-4-yl-1H-imidazol-2-yl]-1-acetylpiperidine (0.11 mmol,41.4 mg) in THF (1.0 mL) was added lithium alumininum hydride (0.14 mmol, 0.14 mL of a 1M solution in THF) and the reaction stirred at room temperature for 2 h. The reaction was then quenched with water (0.1 mL), diluted with ethyl acetate (25 mL), the suspension filtered, the filtrates dried over anhydrous sodium sulfate and the solvent evaporated under reduced pressure. The residue was triturated with diethyl ether to give 25 mg of the title compound as a white powder. mp=242°–244° C.

¹H NMR (CDCl₃) d 8.39 (d,J=6.1 Hz,2H), 7.50–7.40 (m,4H), 7.18 (t,J=8.5 Hz,2H), 3.18–3.05 (m,2H), 2.90–2.75 (m, 1H), 2.51 (q,J=7.3 Hz,2H), 2.25–1.85 (m,6H), 1.15 (t,J=7.3 Hz,3H). Anal; Calcd for C₂₁H₂₃N₄F.0.20H₂O.0.25EtOAc: C 70.27, H 6.81, N 14.90; Found: C 70.21, H 6.73, N 14.83.

EXAMPLE 9

4-[5-(3,4-DICHLOROPHENYL)-4-PYRIDIN-4-YL-1H-IMIDAZOL-2-YL]PIPERIDINE

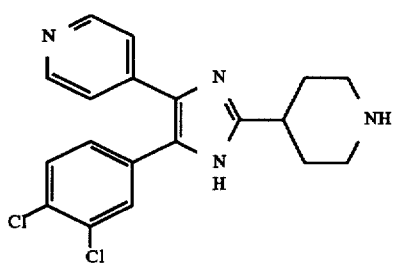

Step 9-A 1-(3,4-Dichlorophenyl)-2-pyridin-4-yl-ethane-1,2-diol

To a stirring solution of diisopropylamine (14.9 g, 19.4 mL, 148 mmol) in tetrahydrofuran (500 mL) at −78° C. was added, dropwise, n-butyllithium (59 mL of a 2.5M solution in tetrahydrofuran). After ten minutes, a solution of 4-pyridylcarbinol t-butyldimethylsilyl ether (30 g, 134 mmol) in tetrahydrofuran (150 mL) was added dropwise and the temperature allowed to rise to −15° C. The solution was again cooled to −78° C. and a solution of 3,4-dichlorobenzaldehyde (25.9 g, 134 mmol) in tetrahydrofuran (150 mL) added dropwise. After the solution was allowed to warm to −20° C., it was poured into saturated aqueous sodium hydrogen carbonate (2 L). The aqueous layer was extracted with ethyl acetate (3×400 mL), the combined organic layers dried over anhydrous magnesium sulfate, filtered and concentrated at reduced pressure. The resulting oil was dissolved in tetrahydrofuran (400 mL) and to this solution was added tetrabutylammonium fluoride (148 mL of a 1.0M solution in tetrahydrofuran) dropwise. After ten minutes, the reaction mixture was concentrated at reduced pressure and the resulting oil chromatographed on silica gel, eluting with 95:5 dichloromethane:methanol to give the title compound as a mixture of diastereomeric diols as a foam (31.7 g) which was used without further purification.

Step 9-B

1(3,4-Dichlorophenyl-2-piperdin-4-yl-ethane-1,2-dione

To a stirring solution of methyl sulfoxide (38.3 g, 35 mL, 490 mmol) in dichloromethane (750 mL) at −78° C. was added trifluoroacetic anhydride (77 g, 52 mL, 368 mmol) dropwise. After ten minutes, 1-(3,4-dichlorophenyl)-2-pyridin-4-yl-ethane-1,2-diol (31.7 g, 112 mmol) in dichloromethane (500 mL) was added dropwise. After another ten minutes, triethylamine (70 g, 96 mL, 690 mmol) was added dropwise and the reaction mixture immediately warmed to 0° C. and poured into saturated aqueous sodium hydrogen carbonate (300 mL). The aqueous layer was extracted with ethyl acetate (3×200 mL) and the organic layers were combined, dried over anhydrous magnesium sulfate, filtered and concentrated at reduced pressure. The resulting solid was triturated with ethyl acetate to give the dione as a yellow solid (23 g).

$^1$H NMR (300 MHz,CDCl$_3$) d 8.90 (dd, J=3.7 and 2.9 Hz, 2H), 8.09 (d, J=1.9 Hz, 1H), 7.85–7.73 (m, 3H), 7.63 (d, J=8.3 Hz, 1H).

Step 9-C

4-[5-(3,4-Dichlorophenyl-4-pyridin-4-yl-1H-imidazol-2-yl]-piperidine-1-carboxylic acid benzyl ester 1-(3,4-Dichlorophenyl)-2-pyridin-4-yl-ethane-1,2-dione (2.8 g, 10 mmol), 4-formylpiperidine-1-carboxylic acid benzyl ester (2.47 g, 10 mmol) and ammonium acetate (7.7 g, 100 mmol) were dissolved in acetic acid (65 mL) and heated to reflux for 2.5 hour and allowed to cool to ambient temperature. The reaction mixture was then poured over an ammonium hydroxide (100 mL) and ice mixture. This aqueous layer was extracted with ethyl acetate (3×200 mL) and the organic layers were combined, washed with brine (100 mL), dried over anhydrous magnesium sulfate, filtered and concentrated at reduced pressure. The resulting oil was chromatographed on silica gel eluting with 97:3 dichloromethane:methanol to give the imidazole as a foam (2.3 g).

$^1$H NMR (300 MHz,CD$_3$OD) d 8.45 (d, J=5.9 Hz, 2H), 7.61 (d, J=1.8 Hz, 1H), 7.53 (d, J=8.3 Hz, 1H), 7.44 (d, J=4.6 Hz, 2H), 7.40–7.26 (m, 8H), 5.15 (s, 2H), 4.29 (d, J=13.6 Hz, 2H), 3.10–2.91 (m, 4H), 2.08–19.5 (m, 2H), 1.91–1.73 (m, 2H).

Step 9-D

4-[5-(3,4-Dichlorophenyl-4-pyridin-4-yl-1H-imidazol-2-yl]piperidine

4-[5-(3,4-Dichlorophenyl)-4-pyridin-4-yl-1H-imidazol-2-yl]piperidine-1-carboxylic acid benzyl ester (3.8 g, 7.5 mmol) dissolved in hydrogen bromide (30 wt. %) in acetic acid (20 mL) was heated to 80° C. for one hour, after which time the reaction mixture was allowed to cool to ambient temperature and concentrated at reduced pressure. The residue was then dissolved in hydrochloric acid (100 mL of 1N) and extracted with ethyl acetate (100 mL). The aqueous layer was then basified with sodium hydroxide (35 mL of 3N) and buffered with saturated aqueous sodium hydrogen carbonate (300 mL). The aqueous layer was extracted with chloroform (5×200 mL) and the organic layers combined, dried over anhydrous sodium sulfate, filtered and concentrated at reduced pressure. The resulting foam was crystallized from ethyl acetate/hexane to give the free amine (2.2 g).

$^1$H NMR (300 MHz,CD$_3$OD) d 8.49–8.43 (m, 2H), 7.63 (d, J=2.0 Hz, 1H), 7.55 (d, J=8.4 Hz, 1H), 7.49–7.43 (m, 2H), 7.33 (dd, J=8.4, 2.0 Hz, 1H), 3.22–3.12 (m, 2H), 2.98 (tt, J=11.9, 3.8 Hz, 1H), 2.76 (dt, J=11.9, 2.5 Hz, 2H), 2.06–1.95 (m, 2H), 1.91–1.75 (m, 2H). m.p.=232°–234° C. Anal: Calcd. for C$_{19}$H$_{18}$N$_4$Cl$_2$.0.95 H$_2$O.0.15 EtOAc: C 58.33, H 5.27, N 13.88. Found: C 58.23, H 4.95, N 13.83.

EXAMPLE 10

4-[5-(3,4-DICHLOROPHENYL)-4-PYRIDIN-4-YL-1H-IMIDAZOL-2-YL]-1-METHYLPIPERIDINE

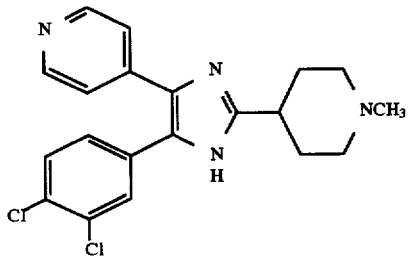

To a stirring solution of 4-[5-(3,4-dichlorophenyl)-4-pyridin-4-yl-1H-imidazol-2-yl]-piperidine-1-carboxylic acid benzyl ester (0.75 g, 1.5 mmol)(from step 9-C above) in tetrahydrofuran (20 mL), under argon, was added lithium aluminum hydride (4.5 mL of a 1.0M solution in tetrahydrofuran) dropwise, after which the solution was heated to reflux. After 30 minutes, the reaction mixture was allowed to cool to ambient temperature and water (5 mL) was added slowly. Ethyl acetate (10 mL) was added, the mixture was vaccuum filtered through paper to remove the aluminum salts, the diluted with saturated aqueous sodium hydrogen carbonate (100 mL) and extracted with ethyl acetate (3×75 mL). The organic layers were combined, washed with brine (100 mL), dried over anhydrous magnesium sulfate, filtered and concentrated at reduced pressure, to give a solid which was recrystallized from ethyl acetate/hexane to give the product as a white solid (280 mg).

$^1$H NMR (300 MHz,CD$_3$OD) d 8.48–8.43 (m, 2H), 7.61 (d, J=1.9 Hz, 1H), 7.55 (d, J=g.3 Hz, 1H), 7.48–7.43 (m, 2H), 7.32 (dd, J=8.3, 1.9 Hz, 1H), 3.06–2.97 (m, 2H), 2.84 (tt, J=11.9, 3.9 Hz, 1H), 2.34 (s, 3H), 2.19 (dt, J=11.9, 2.5 Hz, 2H), 2.09–1.84 (m, 4H). m.p.=239°–241° C. Anal: Calcd. for C$_{20}$H$_{20}$N$_4$Cl$_2$.0.60 H$_2$O: C 60.34, H 5.37, N 14.07. Found: C 60.32, H 5.18, N 13.83.

EXAMPLE 11

2-(4-{4-[5-(3,4-DICHLOROPHENYL-4-PYRIDIN-4-YL-1H-IMIDAZOL-2-YL]-PIPERIDIN-1-YL}-BUTYL-ISOINDOLE-1,3-DIONE

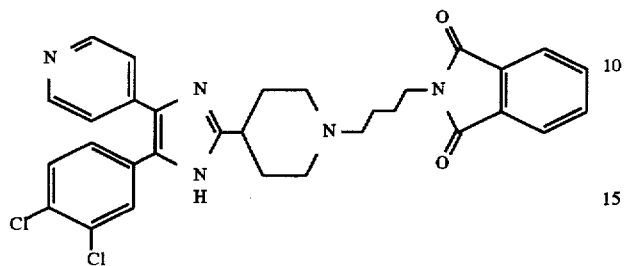

To a stirring solution of 4-[5-(3,4-dichlorophenyl)-4-pyridin-4-yl-1H-imidazol-2-yl]-piperidine (90 mg, 0.24 mmol) in acetonitrile (3 mL) was added N-(5-bromopentyl) phthalimide (82 mg, 0.28 mmol) and sodium bicarbonate (101 mg, 1.2 mmol) and the suspension heated to reflux for 4 hours. After cooling to ambient temperature, the mixture was poured into water (50 mL) and extracted with ethyl acetate (3×50 mL). The organic layers were combined, washed with brine (40 mL), dried over anhydrous magnesium sulfate, filtered and concentrated at reduced pressure. The resulting residue was chromatographed on silica gel eluting with 97:3 chloroform (saturated with ammonia) :methanol and subsequently crystallized from ethyl acetate/ hexane (45 mg). m.p.=199°–202° C.

$^1$H NMR (300 MHz,CD$_3$OD) d 8.49–8.42 (m, 2H), 7.89–7.76 (m, 4H), 7.62 (d, J=1.9 Hz, 1H), 7.54 (d, J=8.3 Hz, 1H), 7.32 (dd, J=8.3, 1.9 Hz, 1H), 3.73 (t, J=6.8 Hz, 2H), 3.08 (d, J=11.7 Hz, 2H), 2.84 (tt, J=12.1, 3.9 Hz, 1H), 2.47 (app t, J=7.6 Hz, 2H), 2.20–2.09 (m, 2H), 2.07–1.82 (m, 4H), 1.78–1.53 (m, 4H). Anal: Calcd. for C$_{31}$H$_{29}$N$_{5O2}$Cl$_2$.0.35 H$_2$O: C 64.11, H 5.15, N 12.06. Found: C 64.15, H 5.10, N 11.86.

Examples 12, 13 and 14 were conducted using a procedure substantially as described above for Example 11.

EXAMPLE 12

2-(5-{4-[5-(3,4-DICHLOROPHENYL)-4-PYRIDIN-4-YL-1H-IMIDAZOL-2-YL]PIPERIDIN-1-YL}PENTYL)ISOINDOLE-1,3-DIONE

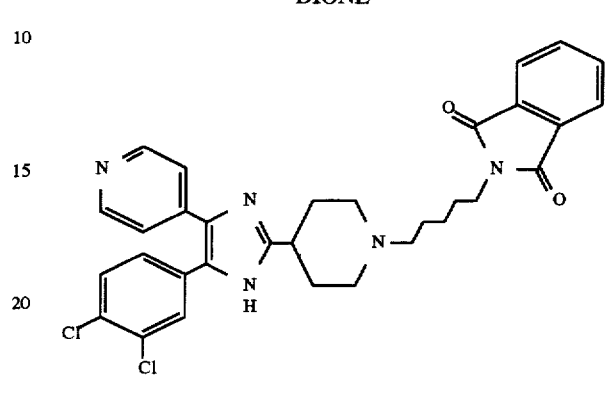

m.p.=129°–134° C.

$^1$H NMR (300 MHz,CD$_3$OD) d 8.49–8.43 (m, 2H), 7.89–7.75 (m, 4H), 7.62 (d, J=2.0 Hz, 1H), 7.54 (d, J=8.3 Hz, 1H), 7.32 (dd, J=8.3, 2.0 Hz, 1H), 3.69 (t, J=6.8 Hz, 2H), 3.25 (d, J=11.9 Hz, 2H), 2.92 (tt, J=12.1, 3.9 Hz, 1H), 2.59 (app t, J=7.4 Hz, 2H), 2.46–2.31 (m, 2H), 2.16–1.89 (m, 4H), 1.79–1.61 (m, 4H), 1.45–1.32 (m, 2H). Anal: Calcd. for C$_{32}$H$_{31}$N$_5$O$_2$Cl$_2$.1.50 H$_2$O: C 62.44, H 5.57, N 11.38. Found: C 62.40, H 5.22, N 11.31.

EXAMPLE 13

2-(6-{4-[5-(3,4-DICHLOROPHENYL)-4-PYRIDIN-4-YL-1H-IMIDAZOL-2-YL]PIPERIDIN-1-YL}HEXYL)ISOINDOLE-1,3-DIONE

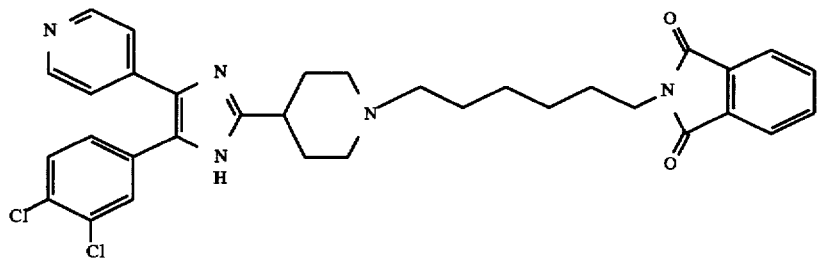

m.p.=129°–134° C.
$^1$H NMR (300 MHz,CD$_3$OD) d 8.48–8.43 (m, 2H), 7.89–7.75 (m, 4H), 7.62 (d, J=1.9 Hz, 1H), 7.54 (d, J=8.3 Hz, 1H), 7.32 (dd, J=8.3, 1.9 Hz, 1H), 3.70 (t, J=6.7 Hz, 2H), 3.26 (d, J=11.7 Hz, 2H), 2.92 (tt, J=12.1, 3.9 Hz, 1H), 2.59 (app t, J=7.4 Hz, 2H), 2.46–2.31 (m, 2H), 2.17–1.88 (m, 4H), 1.80–1.49 (m, 6H), 1.45–1.32 (m, 2H). Anal: Calcd. for C$_{33}$H$_{33}$N$_5$O$_2$Cl$_2$.0.25 H$_2$O.0.50 CH$_2$Cl$_2$: C 61.95, H 5.35, N 10.78. Found: C 61.97, H 5.35, N 10.81.

EXAMPLE 14

4-[5-(3,4-DICHLOROPHENYL)-4-PYRIDIN-4-YL-1H-IMIDAZOL-2-YL]-1-BENZYLPIPERIDINE

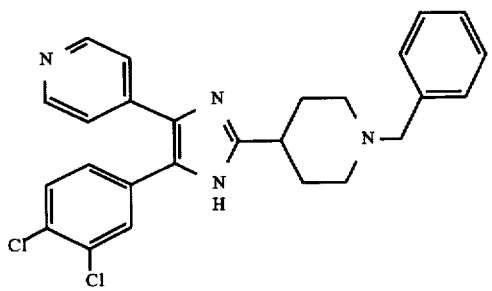

m.p.=192°–195° C.

$^1$H NMR (300 MHz,CD$_3$OD) d 8.48–8.42 (m, 2H), 7.62 (d, J=1.9 Hz, 1H), 7.54 (d, J=8.2 Hz, 1H), 7.47–7.42 (m, 2H), 7.39–7.25 (m, 6H), 3.61 (s, 2H), 3.06 (d, J=12.0 Hz, 2H), 2.85 (tt, J=11.9, 3.9 Hz, 1H), 2.28–2.15 (m, 2H), 2.07–1.85 (m, 4H). Anal: Calcd. for C$_{26}$H$_{24}$N$_4$Cl$_2$.0.35 H$_2$O: C 66.49, H 5.30, N 11.93. Found: C 66.45, H 5.22, N 12.01.

EXAMPLE 15

2-(5-{4-[5-(3,4-DICHLOROPHENYL)-4-PYRIDIN-4-YL-1H-IMIDAZOL-2-YL]PIPERIDIN-1-YL}PENTYL)-2,3-DIHYDRO-ISOINDOL-1-ONE DITRIFLUOROACETIC ACID SALT

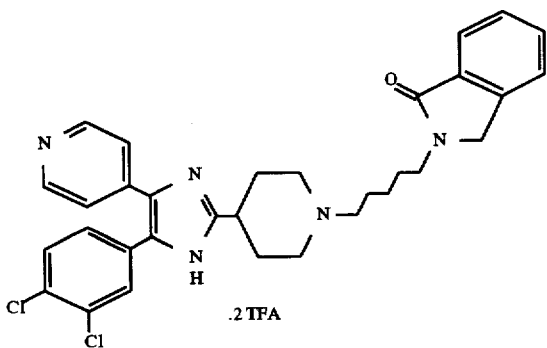

To a stirring solution of 2-(5-{4-[5-(3,4-dichlorophenyl)-4-pyridin-4-yl-1H-imidazol-2-yl]-piperidin-1-yl}-pentyl)-isoindole-1,3-dione (200 mg, 0.34 mmol) (Example 14 above) in acetic acid (3 mL) was added zinc dust (65 mg) and the mixture heated to 100° C. for 2 hours, then allowed to cool to ambient temperature. The mixture was basified to pH 9 with aqueous sodium hydroxide and extracted with chloroform (3×75 mL). The organic layers were combined, dried over anhydrous magnesium sulfate, filtered and concentrated at reduced pressure. The resulting oil was chromatographed on silica gel eluting with 90:10 dichloromethane:methanol to give a solid that was further purified by preparative HPLC and lyophylized to yield the trifluoroacetate salt (25 mg).

$^1$H NMR (300 MHz,CD$_3$OD) d 8.60 (d, J=7.1 Hz, 2H), 8.04 (d, J=7.1 Hz, 2H), 7.80–7.42 (m, 7H), 3.80–3.63 (m, 4H), 3.55–3.48 (m, 1H), 2.48–2.05 (m, 4H), 1.95–1.72 (m, 4H), 1.50–1.38 (2H). Anal: Calcd. for C$_{32}$H$_{33}$N$_5$OCl$_2$.4.05 TFA.0.40 H$_2$O: C 46.15, H 3.66, N 6.71. Found: C 46.15, H 3.67, N 6.86.

EXAMPLE 16

4-(4-{4-[5-(3,4-DICHLOROPHENYL)-4-PYRIDIN-4-YL-1H-IMIDAZOL-2-YL]PIPERIDIN-1-YL}ETHYL)PYRIDINE

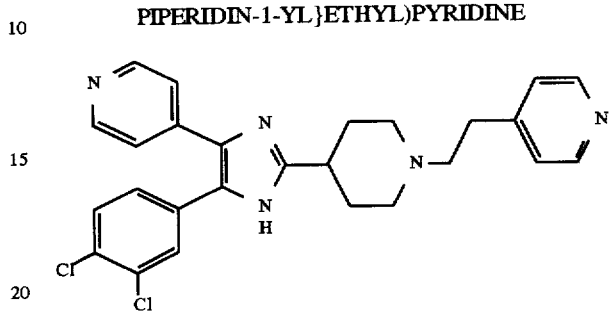

To a stirring solution of 4-[5-(3,4-dichlorophenyl)-4-pyridin-4-yl-1H$_4$midazol-2-yl]-piperidine (Example 11 from above) (250 mg, 0.67 mmol) in methanol (6 mL) was added 4-vinylpyridine (82 mg, 0.28 mmol) and sodium bicarbonate (101 mg, 1.2 mmol) and the suspension heated to 55° C. for 18 hours. The suspension was allowed to cool to ambient temperature, poured into water (100 mL) and the aqueous layer was extracted with ethyl acetate (3×100 mL). The organic layers were combined, washed with brine (80 mL), dried over anhydrous magnesium sulfate, filtered and concentrated at reduced pressure. The residue was chromatographed on silica gel eluting with 95:5 dichloromethane:methanol and subsequently crystallized from ethyl acetate/hexane (150 mg). m.p.=189°–190° C.

$^1$H NMR (300 MHz,CD$_3$OD) d 8.45 (d, J=6.1 Hz, 2H), 8.42 (d, J=6.1Hz, 2H), 7.62 (d, J=1.9 Hz, 1H), 7.54 (d, J=8.3 Hz, 1H), 7.45 (d, J=6.1 Hz, 2H), 7.38–7.31 (m, 3H), 3.16 (d, J=11.7 Hz, 2H), 2.96–2.81 (m, 3H), 2.77–2.67 (m, 2H), 2.10–1.88 (m, 4H). Anal: Calcd. for C$_{26}$H$_{25}$N$_5$Cl$_2$.0.50 H$_2$O: C 64.07, H 5.38, N 14.37. Found: C 64.04, H 5.16, N 14.19.

EXAMPLE 17

2-(5-{4-[5-(3,4-DICHLOROPHENYL)-4-PYRIDIN-4-YL-1H-IMIDAZOL-2-YL]PIPERIDIN-1-YL}PENTYL)-1,1-DIOXOBENZO[D]ISOTHIAZOL-3-ONE

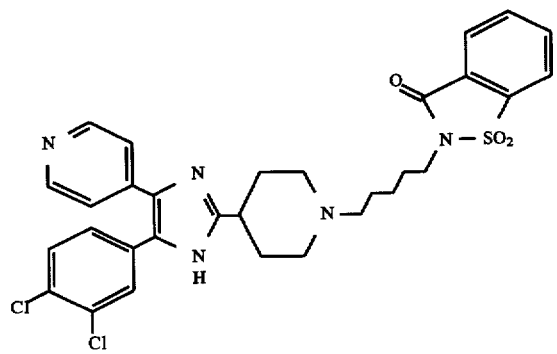

To a stirring solution of 4-[5-(3,4-dichlorophenyl)-4-pyridin-4-yl-1H-imidazol-2-yl]-piperidine (200 mg, 0.54 mmol)(Example 11 from above) in N,N-dimethylformamide (2 mL) was added N-(5-bromopentyl)-1,1-dioxobenzo[d]isothiazol-3-one (213 mg, 0.65 mmol) and triethylamine (137 mg, 0.19 mL, 1.35 mmol). After 6 hours at ambient temperature, the reaction mixture was poured into saturated aqueous sodium hydrogen carbonate solution (125 mL) and extracted with ethyl acetate (3×100 mL). The organic layers were combined, washed with brine (100 mL), dried over anhydrous magnesium sulfate, filtered and concentrated at reduced pressure. The residue was chromatographed on silica gel eluting with 95:5 dichloromethane:methanol, yielding a foam (200 mg).

$^1$H NMR (300 MHz,CD$_3$OD) d 8.46 (d, J=6.1 Hz, 2H), 8.11–8.03 (m, 2H), 8.01–7.89 (m, 2H), 7.63 (d, J=1.9 Hz, 1H), 7.54 (d, J=8.3 Hz, 1H), 7.46 (d, J=6.1 Hz, 2H), 7.33 (dd, 1–8.3, 1.9 Hz, 1H), 3.80 (t, J=6.9 Hz, 2H), 3.19 (d, J=11.8 Hz, 2H), 2.90 (tt, J=10.9, 3.9 Hz, 1H), 2.54 (app t, J=7.9 Hz, 2H), 2.12–1.82 (m, 6H), 1.74–1.60 (m, 2H), 1.54–1.40 (m, 2H). Anal: Calcd. for C$_{31}$H$_{31}$N$_5$O$_3$Cl$_2$S.0.90 H$_2$O: C 58.11, H 5.16, N 10.93. Found: C 58.10, H 4.88, N 10.87.

Example 18 is conducted substantially as described in Example 17.

EXAMPLE 18

2-(4-{4-[5-(3,4-DICHLOROPHENYL)-4-PYRIDIN-4-YL-1H-IMIDAZOL-2-YL]PIPERIDIN-1-YL}BUTYL)-1,1-DIOXOBENZO[D]ISOTHIAZOL-3-ONE

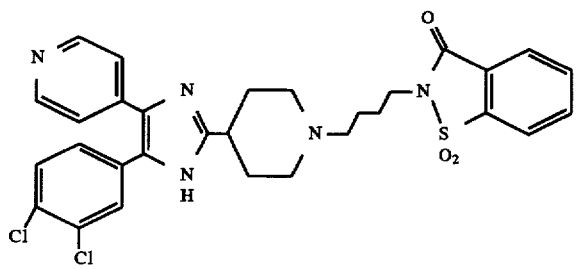

$^1$H NMR (300 MHz,CD$_3$OD) d 8.45 (d, J=6.1 Hz, 2H), 8.11–8.03 (m, 2H), 8.01–7.89 (m, 2H), 7.63 (d, J=1.9 Hz, 1H), 7.54 (d, J=8.3 Hz, 1H), 7.46 (d, J=6.1 Hz, 2H), 7.33 (dd, J=8.3, 1.9 Hz, 1H), 3.83 (t, J=6.9 Hz, 2H), 3.15 (d, J=11.9 Hz, 2H), 2.87 (tt, J=10.5, 3.9 Hz, 1H), 2.54 (app t, J=7.9 Hz, 2H), 2.29–2.16 (m, 6H), 1.76–1.63 (m, 2H). Anal: Calcd. for C$_{30}$H$_{29}$N$_5$O$_3$Cl$_2$S.1.70 H$_2$O: C 56.20, H 5.09, N 10.92. Found: C 56.22, H 4.75, N 10.88.

EXAMPLE 19

4-[5-(3-HYDROXYPHENYL)-4-PYRIDIN-4-YL-1H-IMIDAZOL-2-YL]-1-METHYLPIPERIDINE

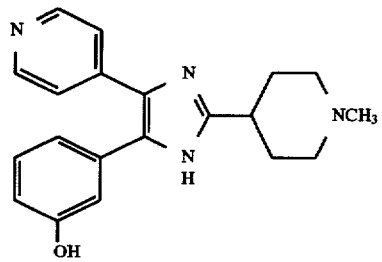

Step 19-A 1-(3-Methoxyphenyl)-2-pyridin-4-ylethane-1,2-diol

To a stirring solution of diisopropylamine (4.5 g, 5.8 mL, 44 mmol) in tetrahydrofuran (170 mL) at −78° C. was added n-butyllithium (17.7 mL of a 2.5M solution in tetrahydrofuran) dropwise. After ten minutes, a solution of 4-pyridylcarbinol t-butyldimethylsilyl ether (9.0 g, 40 mmol) in tetrahydrofuran (35 mL) was added dropwise, and the temperature allowed to rise to −15° C. The solution was recooled to −78° C. and to it was added a solution of 3-anisaldehyde (5.5 g, 4.9 mL, 40 mmol) in tetrahydrofuran (35 mL) dropwise. The solution was allowed to warm to −20° C. and poured into saturated aqueous sodium hydrogen carbonate (300 mL). The aqueous layer was extracted with ethyl acetate (3×200 mL) and the organic layers were combined, dried over anhydrous magnesium sulfate, filtered and concentrated at reduced pressure. The resulting oil was dissolved in tetrahydrofuran (120 mL) and to this solution was added tetrabutylammonium fluoride (48 mL of a 1.0M solution in tetrahydrofuran) dropwise. After ten minutes, the reaction mixture was concentrated at reduced pressure and the resulting oil was chromatographed on silica gel eluting with 97:3 ethyl acetate:methanol to give a mixture of diastereomeric diols as a foam (8.5 g) which was used without further purification.

Step 19-B 1-(3-Methoxyphenyl)-2-pyridin-4-ylethane-1,2-dione

To a stirring solution of methyl sulfoxide (11.8 g, 10.7 mL, 150 mmol) in dichloromethane (150 mL) at −78° C. was added trifluoroacetic anhydride (23.7 g, 16 mL, 113 mmol) dropwise. After ten minutes, 1-(3-methoxyphenyl)-2-pyridin-4-ylethane-1,2-diol (8.5 g, 34 mmol) in dichloromethane (60 mL) was added dropwise. After another ten minutes, triethylamine (21.3 g, 29.4 mL, 211 mmol) was added dropwise and the reaction mixture was immediately warmed to 0° C. and poured into saturated aqueous sodium hydrogen carbonate solution (300 mL). The aqueous layer was extracted with ethyl acetate (3×200 mL) and the organic layers were combined, dried over anhydrous magnesium sulfate and concentrated at reduced pressure. The resulting oil was chromatographed on silica gel eluting with 1:3 ethyl acetate:hexane to give the dione as a yellow solid (5.1 g).

$^1$H NMR (300 MHz,CDCl$_3$) d 8.88 (dd, J=4.4 and 2.5 Hz, 2H), 7.77 (dd, J=4.4 and 2.5 Hz, 2H), 7.56–7.51 (m, 1H), 7.50–7.39 (m, 2H), 7.22–7.19 (m, 1H), 3.85 (s, 3H).

Step 19-C

4-[5-(3-Methoxyphenyl)-4-pyridin-4-yl-1H-imidazol-2-yl]piperidine-1-carboxylic acid tert-butyl ester 1-(3-Methoxyphenyl)-2-pyridin-4-ylethane-1,2-dione (1.93 g, 8.0 mmol), 4-formylpiperidine-1-carboxylic acid tert-butyl ester (1.7 g, 8.0 mmol) and ammonium acetate (6.2 g, 80 mmol) were dissolved in acetic acid (20 mL) and heated to reflux for 2 hours, then allowed to cool to ambient temperature. The reaction mixture was poured over an ammonium hydroxide (50 mL) and ice mixture, extracted with ethyl acetate (3×125 mL) and the combined organic layers dried over anhydrous magnesium sulfate, filtered and concentrated at reduced pressure. The resulting oil was chromatographed on silica gel eluting with ethyl acetate to give the imidazole as a foam (1.2 g), which was used without further purification.

Step 19-D

4-[5-(3-Hydroxyphenyl)-4-pyridin-4-yl-1H-imidazol-2-yl]-1-methylpiperidine

To a stirring solution of 4-[5-(3-methoxyphenyl)-4-pyridin-4-yl-1H-imidazol-2-yl]piperidine-1-carboxylic acid tert-butyl ester (250 mg, 0.58 mmol) in tetrahydrofuran (7 mL) under argon was added lithium aluminum hydride (1.7 mL of a 1.0M solution in tetrahydrofuran) dropwise, after which the solution was heated to reflux for 1.5 hours. The reaction mixture was allowed to cool to ambient temperature and water (3 mL) was added slowly. Ethyl acetate (5 mL) was added and the mixture vaccuum filtered through paper to remove the aluminum salts. The filtrate was diluted with aqueous sodium hydrogen carbonate (100 mL) and extracted with ethyl acetate (3×50 mL). The organic layers were combined, washed with brine (50 mL), dried over anhydrous magnesium sulfate, filtered and concentrated at reduced pressure, to give a solid (150 mg). This solid was dissolved in hydrogen bromide in acetic acid (30 wt %, 5 mL) and the mixture heated at 100° C. for 5 hours. After allowing to cool to ambient temperature, the solution was basified with aqueous sodium hydroxide solution, buffered with aqueous sodium hydrogen carbonate solution and extracted with ethyl acetate (6×50 mL). The organic layers were combined, dried over anhydrous magnesium sulfate, filtered and concentrated at reduced pressure. The residue was triturated with ethyl acetate to give a solid (40 mg).

$^1$H NMR (300 MHz,CD$_3$OD) d 8.38(d, J=6.1 Hz, 2H), 7.49 (d, J=6.1 Hz, 2H), 7.24 (t, J=7.5 Hz, 1H), 6.91–6.79 (m, 3H), 3.03 (d, J=11.7 Hz, 2H), 2.84 (tt, J=11.7, 4.0 Hz, 1H), 2.35 (s, 3H), 2.21 (dt, J=11.7, 2.5 Hz, 2H), 2.08–1.85 (m, 4H). Anal: Calcd. for C$_{20}$H$_{22}$N$_4$O.0.35 H$_2$O.0.70 EtOAc: C 68.06, H 7.09, N 13.92. Found: C 67.99 H 6.89 N 13.92.

EXAMPLE 20

3-[5-(4-FLUOROPHENYL)-4-PYRIDIN-4-YL-1H-IMIDAZOL-2-YL]PIPERIDINE

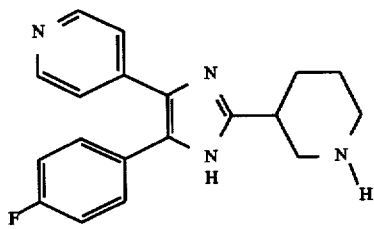

Hydrogen chloride gas was bubbled into a stirred solution of 3-[5-(4-fluorophenyl)-4-pyridin-4-yl-1H-imidazol-2-yl]piperidine-1-carboxylic acid tert-butyl ester in methanol (30 mL) for 0.5 h. The reaction was then evaporated under reduced pressure to give 1.6 g of a pale yellow foam. 0.2 g of the above foam was diluted with saturated sodium bicarbonate (20 mL) and extracted with 1% MeOH:CH$_2$Cl$_2$ (3×50 mL). The organic layers were combined and dried over anhydrous sodium sulfate. The resulting solid was triturated with diethyl ether to give 92 mg of the title compound as a pale yellow powder. mp=252°–254° C.

$^1$H NMR (CD$_3$OD) d 8.79 (d,J=6.5 Hz,2H), 8.17 (d,J=6.5 Hz,2H), 7.72–7.62 (m,2H), 7.35 (t,J=8.5 Hz,2H), 3.85–3.42 (m ,4H), 3.25–3.12 (m, 1H 2.42–2.30 (m, 1H), 2.24–1.90 (m,3H). Anal; Calcd for C$_{19}$H$_{19}$NF.0.25H$_2$O.0.15Et$_2$O: C 66.65, H 6.26, N 16.58; Found: C 69.56, H 6.02, N 16.58.

EXAMPLE 21

3-[5-(4-FLUOROPHENYL)-4-PYRIDIN-4-YL-1H-IMIDAZOL-2-YL]-1-METHYLPIPERIDINE

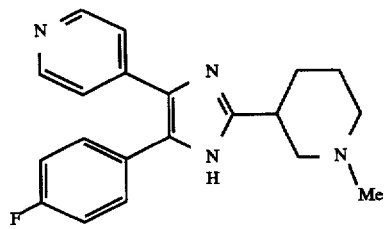

To a stirring solution of 3-[5-(4-fluorophenyl)-4-pyridin-4-yl-1H-imidazol-2-yl]-piperidine-1-carboxylic acid tert-butyl ester (200 mg) in THF (2.0 mL) was added lithium aluminum hydride (1.14 mmol, 1.14 mL of a 1M solution in THF) and the mixture heated to reflux for 6 h. The reaction was quenched with water (2.0 mL), diluted with ethyl acetate (25 mL) and filtered. The filtrates were washed with saturated sodium bicarbonate (50 mL) and the aqueous layer extracted with CH$_2$Cl$_2$ (2×30 mL). The organic layers were combined, dried over anhydrous sodium sulfate and evaporated under reduced pressure and the residue crystallized from diethyl ether to give 60 mg. of the title compound as an off white powder. mp=195°–197° C.

$^1$H NMR (CD$_3$OD) d 8.39 (d,J=5.9 Hz,2H), 7.50–7.40 (m,4H), 7.17 (t,J=8.8 Hz,2H), 3.15–3.04 (m,2H), 2.85–2.96 (m,1H), 2.35 (s,3H), 2.18–2.00 (m,2H), 1.90–1.55 (m,4H). Anal; Calcd for C$_{24}$H$_{27}$N$_2$O$_2$F.0.15H$_2$O: C 70.84, H 6.33, N 16.52; Found: C 70.93, H 6.49, N 16.15.

EXAMPLE 22

4-[5-(4-FLUOROPHENYL)-4-PYRIDIN-4-YL-1H-IMIDAZOL-2-YL]-1-1,4-DIMETHYLPIPERIDINE

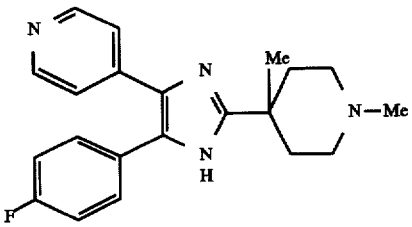

Step 22-A

N-tert-butoxycarbonyl isonipecotic acid ethyl ester

To a stirring solution of isonipecotic acid ethyl ester (31.8 mmol, 5 g) in THF (50 mL) was added di-tert-butyl dicarbonate (31.8 mmol,6.94 g). The reaction was stirred at room temperature for 2 h, diluted with ethyl acetate (300 mL) and washed with 10% KHSO$_4$ (200 mL). The organics were dried over anhydrous sodium sulfate and evaporated under reduced pressure to give 9.09 g of the title compound as a pale yellow oil.

$^1$H NMR (CDCl$_3$) d 4.13 (q,J=7.1 Hz,2H), 4.08–3.95 (m,2H), 2.90–2.75 (m,2H), 2.48–2.35 (m, 1H), 1.95–1.70 (m,2H), 1.70–1.55 (m,2H), 1.52 (s ,9H), 1.25 (t,J=7.1 Hz,3H)

Step 22-B

N-tert-butoxycarbonyl-4-methylisonipecotic acid ethyl ester

To a stirring solution of diisopropylamine (20.0 mmol, 2.02 g) in THF (50 mL) cooled to −78° C. was added n-butyllithium (21.7 mmol, 8.68 mL of a 2.5M solution in hexanes). N-tert-butoxycarbonyl isonipecotic acid ethyl ester (16.7 mmol, 4.5 g) was then added dropwise followed by methyl iodide (16.7 mmol, 2.37 g)and the reaction allowed to warm to room temperature. The mixture was then diluted with ethyl acetate (500 mL) and washed with water (1×200 mL), 10% KHSO$_4$ (200 mL) and brine, dried over anhydrous sodium sulfate and evaporated under reduced pressure to give 4.76 g of the title compound as a pale yellow oil.

$^1$H NMR (CDCl$_3$) d 4.13 (q,J=7.1 Hz,2H), 3.85–3.65 (m,2H), 3.05–2.88 (m,2H), 2.10–1.95 (m, 1H), 1.50–1.10 (m,19H).

Step 22-C

N-tert-butoxycarbonyl-4-methylisonipecotic acid

To a stirring solution of N-tert-butoxycarbonyl-4-methyl-isonipecotic acid ethyl ester (17.4 mmol, 4.73 g) in THF (50 mL) and ethanol (50 mL) was added 50% NaOH (50 mL) and the mixture heated to reflux overnight. The reaction was diluted with 10% KHSO$_4$ (600 mL) and conc. H$_2$SO$_4$ (5 mL) and extracted with ethyl acetate (2×250 mL). The organic layers were combined, washed with water (500 mL) and brine, dried over anhydrous sodium sulfate, and evaporated under reduced pressure. The residue was triturated with diethyl ether:hexanes and filtered to give 1.12 g of an orange solid. The filtrates were evaporated to give 2.71 g of the title compound as an orange solid.

$^1$H NMR (CDCl$_3$) d 3.85–3.65 (m,2H), 3.05–2.88 (m,2H), 2.10–1.95 (m,2H), 1.50–1.30 (m,3H)$_{1.45}$ (s,9H), 1.27 (s,3H).

Step 22-D

N-tert-butoxycarbonyl-4-methyl-4-piperidine-N-methoxy-N-methyl carboxamide

To a stirring solution of N-tert-butoxycarbonyl-4-methyl-4-piperidinecarboxylic acid (4.6 mmol, 1.12 g) in CH$_2$Cl$_2$ (15 mL) was added thionyl chloride (5.0 mmol, 0.60 g) and pyridine (0.1 mL) and the mixture stirred for 1 h at room temperature. The reaction was then evaporated under reduced pressure and the residue taken up in methylene chloride (20 mL) and added dropwise to a stirring suspension of N,O-dimethylhydroxylamine hydrochloride (5.0 mmol, 0.49 g). Triethylamine (10.1 mmol,0.49 g) was then added and the reaction stirred at room temperature for 1 h. The reaction was then diluted with methylene chloride (100 mL), washed with 10% KHSO$_4$ (50 mL), dried over anhydrous sodium sulfate and evaporated under reduced pressure to give 1.05 g of the title compound as an orange oil used without further purification.

Step 22-E

N-tert-Butoxycarbonyl-4-methyl-4-piperidine carboxaldehyde

To a stirring solution of N-tert-Butoxycarbonyl-4methyl-4-piperidine-N-methoxy-N-methylcarboxamide (1.1 mmol, 0.31 g) in THF (5.0 mL) was added lithium aluminum hydride (1.1 mmol, 1.1 mL of a 1M solution in THF) and the reaction stirred at room temperature for 0.5 h. The reaction was quenched with water (0.5 mL), diluted with ethyl acetate (50 mL), filtered and the filtrates washed with 10% KHSO$_4$ (50 mL). The organic layers were dried over anhydrous sodium sulfate and evaporated under reduced pressure to give 0.15 g of the title compound as a colorless oil.

$^1$H NMR (CDCl$_3$) d 3.70–3.50 (m,2H), 3.20–3.00 (m,2H), 2.95–2.80 (m,2H), 1.45–1.20 (m,3H), 1.41 (s,9H), 1.04 (s,3H).

Step 22-F

4-[5-(4-Fluorophenyl)-4-pyridin-4-yl-1H-imidazol-2-yl]-4-methylpiperidine-1-carboxylic acid tert-butyl ester To a stirring solution of 1-(4-fluorophenyl)-2-hydroxy-2-pyridin-4-yl-ethanone tert-butyldimethylsilyl ether (2.0 mmol, 0.65 g) in acetic acid (10 mL) was added N-tert-butoxycarbonyl-4-methyl-4-piperidinecarboxaldehyde (2.2 mmol, 0.5 g), ammonium acetate (20.0 mmol, 1.54 g), and copper acetate (4.0 mmol,0.73 g) and the mixture heated to reflux for 1 h. The reaction was then poured into ice cold 30% aqueous ammonium hydroxide (200 mL), stirred for 0.5 h the phases separated and the aqueous phase extracted with ethyl acetate (2×200 mL). The organic layers were combined, washed with brine and dried over anhydrous sodium sulfate, and evaporated under reduced pressure. The residue was chromatographed over silica eluting with 2% MeOH:CH$_2$Cl$_2$. The product containing fractions were collected and evaporated under reduced pressure to give 0.12 g of the title compound as a white powder. mp=157°–160° C.

$^1$H NMR (CD$_3$OD) d 8.40 (s,2H), 7.55–7.40 (m,4H), 7.25–7.10 (m,2H), 3.80–3.68 (m,2H), 2.40–2.25 (m,2H), 1.75–1.55 (m,2H), 1.46 (s,9H), 1.39 (s,3H).

Step 22-G

4-[5-(4-Fluorophenyl)-4-pyridin-4-yl-1H-imidazol-2-yl]-1,4-dimethyl-piperidine

To a stirring solution of 4-[5-(4-fluorophenyl)-4-pyridin-4-yl-1H-imidazol-2-yl]-4-methylpiperidine-1-carboxylic acid tert-butyl ester (0.14 mmol, 60 mg) in THF (2.0 mL) was added lithium aluminum hydride (0.56 mmol, 0.56 mL of a 1M solution). The reaction was heated to reflux for 6 h, cooled, diluted with ethyl acetate (20 mL) and quenched with water (0.5 mL). The suspension was filtered and the filtrates washed with water (20 mL), dried over anhydrous sodium sulfate and the solvent evaporated under reduced pressure. The resulting solid was triturated with diethyl ether and filtered to give 20 mg of the title compound as a white powder. mp=227°–229° C.

$^1$H NMR (CD$_3$OD) d 8.39 (d,J=6.1 Hz,2H), 7.50–7.40 (m,4H), 7.18 (t,J=8.8 Hz,2H), 2.75–2.62 (m,2H), 2.46–2.30 (m,5H), 2.26 (s,3H), 1.90–1.75 (m,2H), 1.36 (s,3H). Anal; Calcd for C$_{21}$H$_{23}$N$_4$F.0.45H$_2$O.0.10Et$_2$O: C 70.24, H 6.86, N 15.31; Found: C 70.14, H 6.49, N 15.17.

EXAMPLE 23

4-BENZYL-4-[(4-FLUOROPHENYL)-5-PYRIDIN-4-YL-1H-IMIDAZOL-2-YL]PIPERIDINE

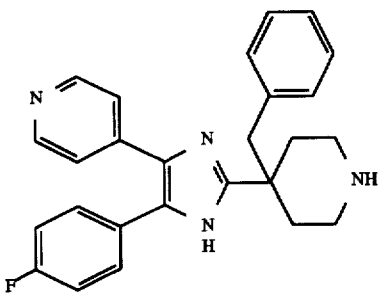

HCl gas was bubbled through a stirring solution of 4-benzyl-4-[(4-fluoro-phenyl)-5-pyridin-4-yl-1H-imidazol-2-yl]-piperidine-1-carboxylic acid tert-butyl ester in ethyl acetate (10 mL) and methanol (2 mL) for 1.25 h. The solution was then evaporated under reduced pressure and the residue taken up in saturated sodium bicarbonate (30 mL) and ethyl acetate (30 mL). The aqueous layer was extracted with ethyl acetate (30 mL), the organic layers were combined, washed with brine, dried over anhydrous sodium sulfate, and evaporated under reduced pressure. The residue was chromatographed over silica, eluting with 5% MeOH:CHCl$_3$ saturated with ammonia. The pure fractions were collected and evaporated. The residue was evaporated from CH$_2$Cl$_2$:hexanes to give 75 mg of the title compound as an off white foam.

$^1$H NMR (CDCl$_3$) d 8.38 (d,J=5.6 Hz,2H), 7.45–7.30 (m,4H), 7.24–7.10 (m,6H), 6.80–6.70 (m,2H), 3.05–2.95 (m,4H), 2.72–2.60 (m,2H), 2.50–2.35 (m,2H), 1.85–1.72 (m,2H). Anal: Calcd. for C$_{26}$H$_{25}$N$_4$F.0.65H$_2$O.0.25 hexanes: C 74.10, H 6.74, N 12.57. Found: C 74.05 H 6.52 N 12.48.

EXAMPLE 24

2-AMINO-1-{5-[4-(3,4-DICHLOROPHENYL)-4-PYRIDIN-4-YL-1H -IMIDAZOL-2-YL]-PIPERIDIN-1-YL}-ETHANONE DIHYDROCHLORIDE

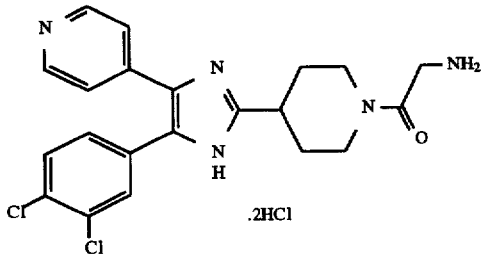

To a stirring solution of 4-[5-(3,4-dichlorophenyl)-4-pyridin-4-yl-1H-imidazol-2-yl]-piperidine (200 mg, 0.54 mmol) in N,N-dimethylformamide (1 mL) was added N-(tert-butoxycarbonyl)glycine (113 mg, 0.59 mmol), 1-ethyl-3-(3-dimethylamino-propyl)carbodiimide hydrochloride (113 mg, 0.59 mmol) and 1-hydroxybenzotriazole hydrate (80 mg, 0.59 mmol) and the mixture stirred at room temperature for 2 hours. The reaction mixture was poured into saturated aqueous sodium hydrogen carbonate (125 mL) and extracted with ethyl acetate (3×100 mL). The organic layers were combined, washed with brine (100 mL), dried over anhydrous magnesium sulfate, filtered and concentrated at reduced pressure. The residue was chromatographed on silica gel eluting with 97:3 dichloromethane:methanol. The resulting foam was dissolved in ethyl acetate (25 mL), cooled to 0° C. and hydrogen chloride gas bubbled through the solution for 30 minutes. The dihydrochloride of the product precipitated out of solution and was filtered to give a yellow solid (150 mg). m.p.= 208°–214° C.

$^1$H NMR (300 MHz,CD$_3$OD) d 8.81 (d, J=6.8 Hz, 2H), 8.13 (d, J=6.8 Hz, 2H), 7.85 (d, J=1.9 Hz, 1H), 7.74 (d, J=8.3 Hz, 1H), 7.51 (dr, J=8.3, 1.9 Hz, 1H), 4.68 (d, J=10.9 Hz, 1H), 4.14–3.98 (m, 3H), 3.50–3.30 (m, 2H), 3.01–2.88 (m, 2H), 2.30–1.88 (m, 4H). Anal: Calcd. for C$_{21}$H$_{21}$N$_5$OCl$_2$.2HCl.2.55 H$_2$O.0.25 EtOAc: C 46.26, H 5.31, N 12.26. Found: C 46.25, H 5.00, N 12.27.

EXAMPLE 25

3-[5-(4-FLUOROPHENYL)-4-PYRIDIN-4-YL-1H-IMIDAZOL-2-YL]-1-ACETYLPIPERIDINE

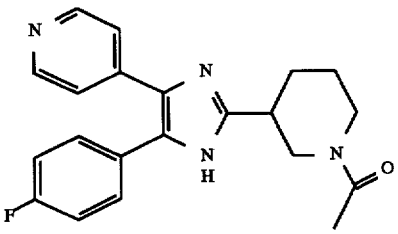

To a stirring solution of 3-[5-(4-fluorophenyl)-4-pyridin-4-yl-1H-imidazol-2-yl]piperidine dihydrochloride (0.76 mmol, 0.3 g) in THF (5.0 mL) was added triethylamine (3.3 mmol, 0.33 g) and acetyl chloride (2.3 mmol, 0.18 g). The reaction was stirred at room temperature for 1 h. diluted with 10% KHSO$_4$ (50 mL) and extracted with ethyl acetate (2×50 mL). The organics were combined, washed with brine, dried over anhydrous sodium sulfate and evaporated under reduced pressure. The residue was chromatographed over silica, eluting with 3% MeOH:CH$_2$Cl$_2$. The pure fractions were collected and evaporated under reduced pressure. The resulting film was evaporated from CH$_2$Cl$_2$: hexanes to give 0.2 g of the title compound as a white foam. Anal; Calcd for C$_{21}$H$_{21}$N$_4$OF.0.75H$_2$O.0.25 hexanes: C 67.65, H 6.56, N 14.02; Found: C 67.72, H 6.30, N 13.91.

EXAMPLE 26

4-[1-PROPYL-5-PYRIDIN-4-YL-4-(3-TRIFLUOROMETHYLPHENYL)-1H-IMIDAZOL-2-YL]PIPERIDINE

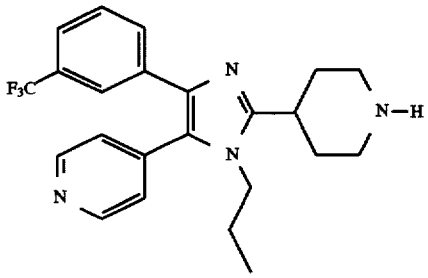

Step 26-A

1-Pyridin-4-yl-2-(3-trifluoromethylphenyl)ethanone

To a stirring solution of 4,4-(dimethoxymethyl)-pyridine (0.131 mol, 20.1 g) [Sheldrake Synth. Commun. 23, 1967 (1993)] in THF cooled to −78° C. under argon was added n-butyllithium (0.139 mol, 55.1 mL of a 2.5M solution in hexanes) in a dropwise manner and the reaction aged 10 min. before 3-trifluoromethylbenzyl chloride (0.134 mol, 26.0 g) was added in a dropwise manner. The reaction was stirred at −78° C. for 20 min, diluted with saturated aqueous sodium bicarbonate (500 mL) and extracted with ethyl acetate (3×250 mL). The combined organic layers were washed with brine, dried over anhydrous sodium sulfate and evaporated under reduced pressure. The residue was dissolved in 96% formic acid (80 mL) diluted with water (20 mL) and heated at reflux for 18 h. The reaction was cooled to ambient temperature and the volatiles removed under reduced pressure. The resulting brown oil was basified to pH7 with aqueous NaOH (aq.) then to pH 10 with saturated potassium carbonate and extracted with ethyl acetate (3×200 mL). The organic layers were combined, dried over anhydrous sodium sulfate and evaporated under reduced pressure. The residue was chromatographed over silica, eluting with a gradient of 20%–65% ethyl acetate:hexane. The pure fractions were combined to give 24.43 g of a brown oil.

$^1$H NMR (CDCl$_3$) d 8.84 (dd, J=4.4 Hz, 1.7 Hz, 2H), 7.78 (dd, J=4.4 Hz, 1.7 Hz, 2H), 7.58–7.42 (m, 4H), 4.36 (s, 2H).

Step 26-B 1-(Pyridin-4-yl)-2-[3-(trifluoromethyl)phenyl]ethane-1,2-dione 2-oxime To a stirring solution of 1-(pyridin-4-yl)-2-[3-(trifluoromethyl)phenylethanone (92 mmol, 24.43 g) in a mixture of acetic acid (80 mL) and water (8 mL) at 0° C. was added a solution of sodium nitrite (138 mmol, 9.53 g) in water (8 mL) and the reaction stirred 10 min. at 0° C. The precipitate which formed was isolated by vacuum filtration and washed with water (50 mL) then dried in vacuo to give 24.43 g (90%) of a pale yellow solid. $^1$H NMR showed a mixture of oxime isomers. The singlet at d 4.36 from the product of step 1 is no longer present.

Step 26-C

4-[1-Propyl-5-pyridin-4-yl-4-(3-trifluoromethylphenyl)-1H-imidazol-2-yl]piperidine-1-carboxylic acid benzyl ester To a stirring solution of 1-(pyridin-4-yl)-2-[3-(trifluoromethyl) phenyl]ethane-1,2-dione 2-oxime (83 mmol, 24.43 g), and 1-benzyloxycarbonyl-piperidine-4-carboxaldehyde [Amici et al Eur. J. Med. Chem. 26, 625–631 (1991)] (108 mmol, 26.7 g) in acetic acid (300 mL) was added propylamine (1.24 mol, 73.6 g) in a dropwise manner at ambient temperature. The reaction was heated to reflux for 3 h, cooled to ambient temperature and basified to pH8 with concentrated ammonium hydroxide/ice and extracted with ethyl acetate (3×500 mL). The combined organic layers were washed with brine dried over anhydrous sodium sulfate and evaporated under reduced pressure. The residue was dissolved in methanol (100 mL) and treated with a solution of titanium trichloride (3×150 mL of 10–20 wt % in 20–30% HCl) and stirred for 18 h. The reaction was basified to pH 10 with saturated potassium carbonate and extracted with ethyl acetate (4×300 ml). The organic layers were combined, washed with brine, dried over anhydrous sodium sulfate and evaporated under reduced pressure. The residue was chromatographed on silica, eluting with a gradient of 30%–60% ethyl acetate:hexane to give a yellow oil which was rechromatographed on silica, eluting with a gradient of 25%–50% ethyl acetate:hexane to give 10.8 g of a pale yellow oil.

$^1$H NMR (CDCl$_3$) d 8.71 (dd, J=4.4 Hz, 1.6 Hz, 2H), 7.74 (s, 1H), 7.44–7.24 (m, 10H), 5.16 (s, 2H), 4.41–4.30 (m, 2H), 3.78 (dd, J=7.9 Hz, 7.7 Hz, 2H), 3.04–2.93 (m, 2H), 2.87 (dddd, J=11.1 Hz, 11.1Hz, 3.8 Hz, 3.8 Hz, 1H), 2.10–2.05 (m, 2H), 1.93–1.90 (m, 2H), 1.57–1.47 (m, 2H), 0.80 (t, J=7.5 Hz, 3H).

Step 26-D

4-[1-Propyl-5-pyridin-4-yl-4-(3-trifluoromethylphenyl)-1H-imidazol-2-yl]piperidine A suspension of 4-[1-propyl-5-pyridin-4-yl-4-(3-trifluoromethylphenyl)-1H-imidazol-2-yl]piperidine-1-carboxylic acid benzyl ester (7.8 mmol, 4.3 g) in 3M hydrochloric acid (70 mL) was heated to 60° C. for 3 h, cooled to ambient temperature and washed with ether (2×50 mL) and the organic phases discarded. The aqueous layer was basified with aqueous sodium hydroxide to pH10 and extracted with dichloromethane (3×100 mL) and ethyl acetate (100 mL). The combined organic layers were dried over anhydrous sodium sulfate and evaporated under reduced pressure. The residue was chromatographed over silica, eluting with a gradient of 95:5:0.5 to 90:10 dichloromethane:methanol:ammonium hydroxide to give an off-white foam which was recrystallized from 25% ethyl acetate in hexanes to give the title compound as an off-white solid.

$^1$H NMR (CDCl$_3$) d 8.70 (dd, J=4.4 Hz, 1.5 Hz, 2H), 7.77 (s, 1H), 7.44–7.38 (m, 2H), 7.29–7.23 (m, 3H), 3.78 (dd, J=8.1 Hz, 7.6 Hz, 2H), 3.30–3.26 (m, 2H), 2.89–2.73 (m, 3H), 2.01–1.88 (m, 4H), 1.51 (sextet, J=7.6 Hz, 2H), 0.80 (t, J=7.6 Hz, 3H). Anal. Calculated for C$_{23}$H$_{25}$F$_3$N$_4$·0.35 H$_2$O: C65.65 H6.16 N13.31. Found: C65.61 H6.08 N13.42.

EXAMPLE 27

(S)-4-[5-(2-(1-PHENYLETHYLAMINO)-PYRIDIN-4-YL)-1-METHYL-4-(3-TRIFLUOROMETHYLPHENYL)-1H-IMIDAZOL-2-YL]PIPERIDINE

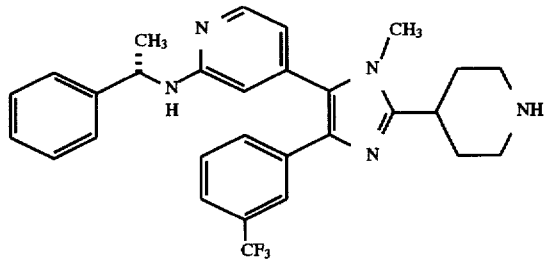

Step 27-A

2-(2-Fluoropyridin-4-yl)-1-(3-trifluoromethylphenyl) ethanone

To a solution of diisopropylamine (17.69 mL, 0.135 mole) in THF (200 mL) at −78° C., under argon, was added n-butyllithium (54.0 mL, 2.5M in hexane, 0.135 mole), followed after 5 min. by a solution of 2-fluoro-4-methylpyridine (Lancaster Synthesis Inc.) (10 g, 0.090 mole) in THF (20 mL). After stirring for 15 min. at −78° C., a solution of N-methoxy-N-methyl-3-trifluoromethylbenzamide (23.08 g, 0.099 mole) in THF (10 mL) was added. After stirring for 5 min, the reaction was allowed to warm to 0° C. and quenched by pouring into water (400 mL) and ethyl acetate (400 mL). The layers were separated, and the aqueous layer washed with ethyl acetate (200 mL). The ethyl acetate extracts were combined, dried over anhydrous sodium sulfate, filtered, and concentrated to an oil which was chromatographed on silica gel with 20% ethyl acetate in hexane to give 21.6 g of the title compound.

NMR (300 MHz, CDCl$_3$) d: 8.25 (1H, s); 8.20 (1H, d, J=5.1 Hz); 8.18 (1H, d, J=9.3 Hz); 7.88 (1H, d, J=7.8 Hz); 7.67 (1H, t, J=7.5 Hz); 7.09 (1H, d, J=5.1 Hz); 6.86 (1H, s); 4.37 (2H, s).

Step 27-B

1-(2-Fluoropyridin-4-yl)-2-(3-trifluoromethylphenyl)-ethane-1,2-dione-1-oxime To a mixture of 2-(2-fluoropyridin-4-yl)-1-(3-trifluoromethylphenyl)ethanone (10.80 g, 0.038 mole) in ethanol (200 mL), at −10° C., under argon, was added tert-butylnitrite (5.0 mL, 0.042 mol) followed by hydrogen chloride (12.2 mL, 2.5M in ethanol, 0.031 mole) dropwise while maintaining the temperature below −5° C. Upon completion of addition, the reaction was allowed to warm to room temperature for 2 hours. The reaction was concentrated in vacuo, diluted with water (100 mL), basified with saturated sodium bicarbonate (200ml). This mixture was then extracted with ethyl acetate (1×600 mL, 2×300 mL). The organic layers were combined, washed with water (300 mL), washed with brine (300 mL), dried over anhydrous sodium sulfate, filtered and concentrated to an oil (11.4 g).

¹H NMR (300 MHz, CDCl$_3$) d: 8.31(1H, s); 8.29 (1H, d, J=5.3 Hz); 8.24 (1H, d, J=7.8 Hz); 7.92 (1H, d, J=8.1 Hz); 7.71(1H, t, J=7.8 Hz); 7.40 (1H, d, J=5.1 Hz); 7.23 (1H, s).

Step 27-C

4-[1-Hydroxy-5-(2-fluoropyridin-4-yl)-4-(3-trifluoromethylphenyl)-1H-imidazol-2-yl]piperidine-1-carboxylic acid benzyl ester To a mixture of 1-(2-fluoropyridin-4-yl)-2-(3-trifluoromethylphenyl)ethane-1,2-dione-1-oxime (11.4 g, 0.037 mole) and N-benzyloxycarbonylpiperidin-4-carboxaldehyde [Amici et al Eur. J. Med. Chem. 26, 625–631 (1991)] (9.93 g, 0.040 mol), in acetic acid (250 mL) was added ammonium acetate (56.29 g, 0.730 mole). The mixture was heated to 75° C. for 1 h, cooled and concentrated to remove most of the acetic acid. The residue was poured into concentrated NH$_4$OH (100 mL), ice (200 g) and methylene chloride (800 mL) and the pH adjusted to 8 with NH$_4$OH. The methylene chloride layer was removed and the aqueous layer washed with methylene chloride (2×300 mL). The combined organic phases were washed with water (300 mL), brine (300 mL), dried over anhydrous sodium sulfate, filtered and concentrated to give an oil used in the next step without further purification.

Step 27-D

4-[5-(2-Fluoropyridin-4-yl)-4-(3-trifluoromethylphenyl-1H-imidazol-2-yl]piperidine-1-carboxylic acid benzyl ester To a stirred solution of crude 4-[1-hydroxy-5-(2-fluoropyridin-4-yl)-4-(3-trifluoromethylphenyl)-1H-imidazol-2-yl]piperidine-1-carboxylic acid benzyl ester (from the above step) in methanol (400 mL) at 0° C. was slowly added titanium III) chloride (150 mL, 0.174 mole, 15% wt in 20–30% HCl). The reaction was allowed to stir for 2 hours at room temperature. Upon completion, the reaction was concentrated to remove methanol and quenched into saturated aqueous sodium bicarbonate (750 mL) and ethyl acetate (1500 mL). After stirring for 4 hours, the organic layer was removed and aqueous washed with ethyl acetate (2×750 mL). The organic extracts were combined, washed with water (750 mL), brine (750 mL), dried over anhydrous sodium sulfate, then concentrated to an oil. The oil was dissolved in ethyl acetate (10 mL) and chromatographed on silica using 40% ethyl acetate/hexane to give 14.5 g (76% from oxime) of a yellow foam upon concentration of appropriate fractions.

NMR (300 MHz, CD$_3$OD) d 8.07(1H, d, J=5.1 Hz); 7.76 (1H, s); 7.70 (1H, t, J=7.3 Hz); 7.68 (1H, d, J=7.6 Hz); 7.63 (1H, d, J=7.3 Hz); 7.38 (5H, m); 7.26 (1H, d, J=4.5 Hz); 7.09 (1H, s); 5.14 (2H, s); 4.29 (2H, d, J=13.4 Hz); 3.06 (3H, m); 2.04 (2H, d, J=12.9 Hz); 1.87 (2H, m).

Step 27-E

4-[5-(2-Fluoropyridin-4-yl)-1-methyl-4-(3-trifluoromethylphenyl-1H-imidazol-2-yl]-piperidine-1-carboxylic acid benzyl ester To a stirring solution of 4-[5-(2-fluoropyridin-4-yl)-4-(3-trifluoromethylphenyl)-1H-imidazol-2-yl]-piperidine-1-carboxylic acid benzyl ester (13.1 g, 0.025 mmole) in toluene (130 mL) was added N,N-dimethylformamide dimethyl acetal (13.1 mL). This mixture was heated to 120° C. under argon for 28 hours. The reaction was cooled, concentrated in vacuo, poured into a saturated aqueous solution of sodium bicarbonate (300 mL) which was extracted with ethyl acetate (1×1 L, 2×300 mL). The organic extracts were combined, washed with water (300 mL), brine (300 mL), dried over anhydrous sodium sulfate and concentrated to an oil. The oil was dissolved in methylene chloride (5 mL) and chromatographed on silica using 2% acetone/methylene chloride to give upon concentration of the product containing fractions the title compound 2.00 g.

NMR (300 MHz, CD$_3$OD) d: 8.27 (1H, d, J=5.1 Hz); 7.65 (1H, s); 7.51 (2H, m); 7.45 (1H, d, J=7.8 Hz); 7.38 (5H, m); 7.25 (1H, d, J=5.1 Hz); 7.09 (1H, s); 5.15 (2H, s); 4.31 (2H, d, J=13.2 Hz); 3.31 (3H, s); 3.19 (1H, m); 3.06 (2H, brs); 1.97 (4H, m).

Additional elution of the above column chromatography with 10% acetone/methylene chloride gave 4-[4-(2-fluoropyridin-4-yl)-1-methyl-5-(3-trifluoromethylphenyl)-1H-imidazol-2-yl]-piperidine-1-carboxylic acid benzyl ester 6.84 g (51%).

NMR (300 MHz, CD$_3$OD) d: 7.97 (1H, s); 7.92 (1H, d, J=5.6 Hz); 7.86 (1H, d, J=7.6 Hz); 7.76 (1H, t, J=7.6 Hz); 7.66 (1H, d, J=7.6 Hz); 7.38 (5H, m); 7.11 (1H, d, J=5.4 Hz); 6.98 (1H, s); 5.15 (2H, s); 4.29 (2H, d, J=13.4 Hz); 3.47 (3H, s); 3.17 (3H, m); 1.97 (4H, m).

Step 27-F (S)-4-[5-(2-(1-Phenylethylamino)pyridin-4-yl)-1-methyl-4-(3-trifluoromethylphenyl)-1H-imidazol-2-yl]-piperidine-1-carboxylic acid benzyl ester A mixture of 4-[5-(2-fluoropyridin-4-yl)-1-methyl-4-(3-trifluoromethylphenyl)-1H-imidazol-2-yl]-piperidine-1-carboxylic acid benzyl ester (1.0 g, 0.0019 mole) and S(−)-(a)-methylbenzylamine (99% ee) (2.39 mL, 0.019 mole) was heated to 150° C. for 19 hours, under argon. The mixture was cooled and chromatographed on silica (200 g) using 10% acetone/methylene chloride to give (S)-4-[5-[2-(1-phenylethylamino)-pyridin-4-yl]-1-methyl-4-(3-trifluoromethylphenyl)-1H-imidazol-2-yl]-piperidine-1-carboxylic acid benzyl ester (0.82 g).

NMR (300 MHz, CD$_3$OD) d: 7.99 (1H, d, J=5.9 Hz); 7.66 (1H, s); 7.49 (1H, d, J=7.8 Hz); 7.46 (1H, d, J=9.3 Hz); 7.28 (11H, m); 6.44 (1H, d, J=6.6 Hz); 6.32 (1H, s); 5.14 (2H, s); 4.80 (1H, q, J=6.5 Hz); 4.29 (2H, d, J=13.4 Hz); 3.38 (3H, s); 3.18 (2H, d, J=13.2 Hz); 3.03 (3H, m); 1.95 (4H, m); 1.48 (3H, d, J=6.5 Hz).

Step 27-G (S)-4-[5-(2-(1-Phenylethylamino)-PYRIDIN -4-yl)-1-methyl-4-(3-trifluoromethylphenyl)-1H-imidazol-2-yl]piperidine To a solution of (S)-4-[5-[2-(1-phenylethylamino)-pyridin-4-yl]-1-methyl-4-(3-trifluoromethylphenyl)-1H-imidazol-2-yl]-piperidine-1-carboxylic acid benzyl ester (1.00 g, 0.0016 mole) in isopropanol (30 mL), under argon, was added 10% Pd/C (0.40 g). This solution was stirred for 10 h, at room temperature under 1 atm of hydrogen. The mixture was filtered under argon and the catalyst cake washed with isopropanol (100 mL). The combined filtrates were concentrated to an oil which was chromatographed on silica using 90:10:1 methylene chloride:methanol:amonium hydroxide to give, upon concentration of the product containing fractions, the title compound (0.69 g). Anal. Calc. for C$_{28}$H$_{29}$N$_6$F$_3$·0.50H$_2$O & 0.15 Hexanes Calculated: C 68.08%, H 6.32%, 13.28% Found: C 68.04%, H 6.35%, 13.20%

NMR (300 MHz, CD$_3$OD) d: 7.98 (1H, d, J=5.4 Hz); 7.69 (1H, s); 7.49 (1H, d, J=7.6 Hz); 7.46 (1H, d, J 7.8 Hz); 7.36 (1H, t, J=7.5 Hz); 7.29 (5H, m); 6.45 (1H, d, J=6.5 Hz); 6.32 (1H, s); 4.80 (1H, q, J=6.8 Hz); 3.38 (3H, s); 3.18 (2H, d, J=13.2 Hz); 3.04 (1H, m); 2.77 (2H, m); 1.90 (4H, m); 1.48 (3H, d, J=6.5 Hz).

BIOLOGICAL ASSAYS

The ability of compounds of the present invention to inhibit cancer can be demonstrated using the following assays.

Raf kinase assay

Raf kinase activity in vitro is measured by the phosphorylation of its physiological substrate MEK (Map/ERK kinase). Phosphorylated MEK is subsequently trapped on a filter membrane and incorporation of radio-labeled phosphate is quantitated by scintillation counting.

MATERIALS

Activated Raf

Produced in Sf9 insect cells coinfected with three different baculoviruses expressing epitope-tagged Raf, and the upstream activators Val$^{12}$-H-Ras, and Lck. The epitope sequence Glu-Tyr-Met-Pro-Met-Glu ("Glu-Glu") was fused to the carboxy-terminus of full-length c-Raf.

MEK

Catalytically inactive MEK is produced in Sf9 cells infected with baculovirus expressing epitope-tagged MEK with a lysine$^{97}$ to alanine mutation (K97A). The epitope sequence Glu-Tyr-Met-Pro-Met-Glu ("Glu-Glu") was fused to the amino-terminus of full-length MEK1.

Anti "Glu-Glu" antibody

A hybridoma cell line expressing an antibody specific for the "Glu-Glu" epitope was obtained from Gernot Walter, UCSD. Cells were grown and antibodies were purified as described (Grussenmeyer et al., Proc. Natl. Acad. Sci. U.S.A., 82, pp. 7952–7954, 1985).

Column buffer 20 mM Tris, pH 8, 100 mM NaCl, 1 mM EDTA, 2.5 mM EGTA, 10 mM MgCl$_2$, 2 mM DTT, 0.4 mM AEBSF, 0.1% n-octyl glucopyranoside, 1 nM okadeic acid, and 10 mg/mL each of benzamidine, leupeptin, pepstatin, and aprotinin (all SIGMA).

5×reaction buffer 125 mM HEPES pH=8.0, 25 mM MgCl$_2$, 5 mM EDTA, 5 mM Na$_3$VO$_4$, 100 mg/mL BSA Enzyme dilution buffer 25 mM HEPES pH=8.0, 1 mM EDTA, 1 mM Na$_3$VO$_4$, 400 mg/mL BSA.

Stop solution 100 mM EDTA, 80 mM sodium pyrophosphate.

Filter plates

Millipore Multiscreen #SE3M078E3, Immobilon-P (PVDF).

METHOD

A. Protein purification

1. Sf9 insect cells were infected with baculovirus and grown as described (Williams et al., Proc. Natl. Acad. Sci. U.S.A., 89, pp. 2922–2926, 1992).

2. All subsequent steps were performed on ice or at 4° C. Cells were pelleted and lysed by sonication in column buffer. Lysates were spun at 17,000× g for 20 min, followed by 0.22 mm filtration.

3. Epitope-tagged proteins were purified by chromatography over a GammaBind Plus (Pharmacia) affinity column to which "Glu-Glu" antibody had been coupled. Proteins were loaded on the column, followed by washes with two column volumes of column buffer, and eluted with 50 mg/mL of peptide antigen (Glu-Tyr-Met-Pro-Met-Glu) in column buffer.

B. Raf kinase assay

1. Add 10 mL of inhibitor or control in 10% DMSO to assay plate.

2. Add 30 mL of reaction mix containing 10 mL 5× reaction buffer and 0.5 mL 1 mM $^{33}$P-g-ATP (20 mCi/mL), 0.5 mL MEK (2.5 mg/mL), 1 mL 50 mM b-mercaptoethanol.

3. Start reaction by addition of 10 mL enzyme dilution buffer containing 1 mM DTT and an empirically determined amount of activated Raf that produces linear incorporation kinetics over the reaction time course.

4. Mix and incubate at room temperature for 90 min.

5. Stop reaction by addition of 50 mL stop solution.

6. Prewet filter plate with 70% ethanol and rinse with water.

7. Transfer 90 mL aliquots of stopped reaction to filter plate.

8. Aspirate and wash four times with 200 mL H$_2$O.

9. Add 50 mL scintillation cocktail, seal plate, and count in Packard TopCount scintillation counter.

Map Kinase Phosphorylation assay

Inhibition of Raf kinase activity in intact cells is measured by determining the phosphorylation state of Map Kinase in TPA-stimulated C-33a human epithelial cells. Phosphorylated Map Kinase is detected by "Western" blot using an anti-phospho-Map Kinase antibody.

Materials

C33a Human Epithelial Cells

The C33a cell line is obtained from the ATCC repository, catalog #H TB31, and is maintained in DMEM (Mediatech) +10% fetal bovine serum+1% penicillin/streptomycin (Gibco) according to the instructions provided.

Anti-phospho-MAP Kinase antibody

The rabbit polyclonal anti-phospho-MAP kinase antibody is obtained from New England Biolabs (Beverly, Mass.)

Secondary antibody

The anti-rabbit antibody-alkaline phosphatase conjugate is obtained from New England Biolabs Acrylamide Gel Ten percent bis-acrylamide electrophoresis gels were obtained from Novex.

Blocking Buffer

1×Phosphate-buffered saline, 0.1% Tween-20, 5% nonfat dry milk.

Antibody dilution buffer

1×phosphate-buffered saline, 0.05% Tween-20, 5% bovine serum albumin

Alkaline phosphatase substrate

The chemiluminescent alkaline phosphatase substrate, CDP-Staff™, is obtained from New England Biolabs.

Assay Buffer 0.1M diethanolamine, 1 mM MgCl$_2$.

Method

1. C33a cells are grown to confluency in 24 well plates, then starved for 24 hr in DMEM+0.5% charcoal-stripped serum.

2. Compound to be tested, dissolved in DMSO at 1000× concentration, is added to each well.

3. One hour later, TPA (dissolved in DMSO at 1000× concentration) is added at a final concentration of 100 ng/mL.

4. Twenty minutes later, the media is removed from all wells, and 100 µl of boiling hot reducing Laem mLi sample buffer is added to each well. The plate is agitated, and the cell lysate is transferred to a 1.5 mL plastic microcentrifuge tube. Each lysate is then sonicated for 10 s, and placed in a boiling water bath for 5–10 minutes. Fifteen microliters of each sample is then loaded on a 10% Laem mLi polyacrylamide gel (Novex), and the gel electrophoresed according to the manufacturer's instructions.

5. Proteins in the gel are electroblotted to a PVDF membrane, which is then rinsed in PBS and blocked with Blocking Buffer for approximately 1 hr at room temperature.

6. The PVDF membrane is rinsed in PBS. The anti-phospho-MapK antibody, diluted approximately 1:500 in antibody dilution buffer, is incubated with the PVDF membrane with gentle agitation overnight at 4° C.

7. The PVDF membrane is rinsed 3 times for 5 minutes with Blocking Buffer, then incubated with the secondary antibody, diluted approximately 1:1000 in antibody dilution buffer, for 1 hr with gentle agitation at room temperature.

8. The PVDF membrane is rinsed 5 times for 5 minutes with Blocking Buffer, then incubated with the chemiluminescent alkaline phosphatase substrate dissolved in Assay Buffer for approximately 5 minutes. The membrane is then rinsed, wrapped in plastic, and exposed to x-ray film to detect blotted proteins.

The ability of compounds of the present invention to inhibit the synthesis or the activity of cytokines can be demonstrated using the following in vitro assays.

Lipopolysaccharide mediated production of cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of 2×10$^6$ cell/mL in RPMI containing 10% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and are incubated for 24 hours. at 37° C. in 5% CO$_2$. At the end of the culture period, cell culture supernatants are assayed for IL-1b, TNF-a, IL-6 and PGE2 production using specific ELISA.

IL-1mediated cytokine production

Human peripheral blood mononuclear cells are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of 2×10$^6$ cell/mL in RPMI containing 10% fresh autologous human serum, penicillin streptomycin (10 U/mL) and 0.05% DMSO. Endotoxin free recombinant human IL-1b is then added to a final concentration of 50 pMolar. An aliquot (0.1 mL) of the cells is quickly dispensed into each well of a 96 well plate containing 0.1 mL of the compound at the appropriate dilution, and are incubated for 24 hours. at 37° C. in 5% CO$_2$. At the end of the culture period, cell culture supernatants are assayed for TNF-a, IL-6 and PGE2 synthesis using specific ELISA.

Determination of IL-1b, TNF-a, IL-6 and prostanoid production from LPS or IL-1Stimulated PBMC's IL-1b ELISA Human IL-1b can be detected in cell-culture supernatants or whole blood with the following specific trapping ELISA. Ninety-six well plastic plates (Iratoulon 4; Dynatech) are coated for 12 hours at 4° C. with 1 mg/mL protein-A affinity chromatography purified mouse anti-human IL-1b monoclonal antibody (purchased as an ascites preparation from LAO Enterprise, Gaithersburg Md.) diluted in Dulbecco's phosphate-buffered saline (—$MgCl_2$, —$CaCl_2$). The plates are washed with PBS-Tween (Kirkegaard and Perry) then blocked with 1% BSA diluent and blocking solution (Kirkegaard and Perry) for 60 minutes at room temperature followed by washing with PBS Tween. IL-1b standards are prepared from purified recombinant IL-1b produced from E. coli. The highest concentration begins at 10 ng/mL followed by 11 two-fold serial dilutions. For detection of IL-1b from cell culture supernatants or blood plasma, 10–25 mL of supernatant is added to each test well with 75–90 mL of PBS Tween. Samples are incubated at room temperature for 2 hours then washed 6 times with PBS Tween on an automated plate washer (Dennly). Rabbit anti-human IL-1b polyclonal antisera diluted 1:500 in PBS-Tween is added to the plate and incubated for 1 hour at room temperature followed by six washes with PBS-Tween. Detection of bound rabbit anti-IL-1b IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-a ELISA

Immulon 4 (Dynatech)96-well plastic plates are coated with a 0.5 mg/mL solution of mouse anti-human TNF-a monoclonal antibody. The secondary antibody is a 1:2500 dilution of a rabbit anti-human TNF-a polyclonal serum purchased from Genzyme. All other operations are identical to those described above for IL-1b. The standards are prepared in PBS-Tween+10% FBS or HS. Eleven 2 fold dilutions are made beginning at 20 ng/mL TNF-a.

IL-6 ELISA

Levels of secreted human IL-6 are also determined by specific trapping ELISA as described previously in Chin and Kostura, J. Immunol. 151, 5574–5585 (1993). (Dynatech) ELISA plates are coated with mouse anti-human IL-6 monoclonal antibody diluted to 0.5 mg/mL in PBS. The secondary antibody, a rabbit anti-human IL-6 polyclonal antiserum, is diluted 1:5000 with PBS-Tween. All other operations are identical to those described above for IL-1b. The standards are prepared in PBS-Tween+10% FBS or HS. Eleven 2 fold dilutions are made beginning at 50 ng/mL IL-6.

$PGE_2$ production

Prostaglandin E2 is detected in cell culture supernatants from LPS or IL-1stimulated PBMC's using a commercially available enzyme immunoassay. The assay purchased from the Cayman Chemical (Catalogue number 514010) and is run exactly according to the manufacturers instructions.

Interleukin8 (IL-8)

The present compounds can also be assayed for IL-8 inhibitory activity as discussed below. Primary human umbilical cord endothelial cells (HUVEC) (Cell Systems, Kirland, Wa) are maintained in culture medium supplemented with 15% fetal bovine serum and 1% CS-HBGF consisting of aFGF and heparin. The cells are then diluted 20-fold before being plated (250 µl) into gelatin coated 96-well plates. Prior to use, culture medium is replaced with fresh medium (200 µl). Buffer or test compound (25 µl, at appropriate concentrations) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/mL) of multiple samples based on the standard curve. $IC_{50}$ values where appropriate are generated by non-linear regression analysis.

Using the Raf kinase assay, the $IC_{50}$ ranges from about 0.001 mM to about 1.5 mM.

What is claimed is:

1. A compound represented by formula I:

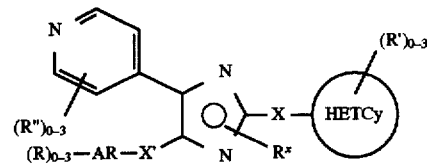

or a pharmaceutically acceptable salt thereof, wherein:

AR represents an aromatic group containing 6–10 atoms;

X and X' each independently represent —$(CH_2)_m$—Y—$(CH_2)_n$—, wherein m and n represent integers within the range of from 0–4, such that the sum of m and n is from 0–6; Y represents a member selected from the group consisting of: a direct bond; O; $S(O)_y$, with y equal to 0, 1 or 2; $NR^{q'}$, with $R^{q'}$ as defined below; C(O); OC(O); C(O)O; $SO_xNR^{q'}$ with x equal to 1 or 2 and $R^{q'}$ as defined below; $NR^{q'}SO_x$; C(O)$NR^{q'}$ and $NR^{q'}$C(O);

represents a 4 to 6 membered non-aromatic heterocycle containing only N atom;

$R^x$ represents H, $C_{1-6}$alkyl$(R^q)_3$, $OC_{1-6}$alkyl$(R^q)_3$ or C(O)$C_{1-6}$alkyl$(R^q)_3$;

each R and R" independently represents a member selected from the group consisting of: halo; hydroxy; $C_{1-6}$alkyl$(R^q)_3$; $OC_{1-6}$alkyl$(R^q)_3$; $C_{3-8}$cycloalkyl$(R^q)_3$; CN; $CONH_2$; CONH$C_{1-6}$alkyl$(R^q)_3$; CON($C_{1-6}$alkyl$(R^q)_3)_2$; $NH_2$; NH$C_{1-6}$alkyl$(R^q)_3$; N($C_{1-6}$alkyl$(R^q)_3)_2$; $CO_2H$; $CO_2C_{1-6}$alkyl$(R^q)_3$; C(O)$C_{1-6}$alkyl$(R^q)_3$; aryl$(R^q)_3$; heteroaryl$(R^q)_3$; $CF_3$; SH; $NO_2$; $SO_xC_{1-6}$alkyl$(R^q)_3$, with y as defined above; $SO_2NH_2$; $SO_2NHC_{1-6}$alkyl$(R^q)_3$; $SO_2N(C_{1-6}$alkyl$(R^q)_3)_2$; $NHSO_2C_{1-6}$alkyl$(R^q)_3$, $NHSO_2$aryl$(R^q)_3$, $NHSO_2$heteroary$(R^q)_3$, N($R^{q'}$)C(O)$C_{1-6}$alkyl$(R^q)_3$; $NR^{q'}$C(O)NH($C_{1-6}$alkyl$(R^q)_3$); $C_{2-4}$alkenyl$(R^q)_{2-3}$ and $C_{2-4}$alkynyl$(R^q)_{1-3}$;

each R' independently represents a member selected from the group consisting of: hydroxy; $C_{1-6}$alkyl$(R^q)_3$; $C_{3-8}$cycloalkyl$(R^q)_3$; $OC_{1-6}$alkyl$(R^q)_3$; $OC_{3-8}$cycloalkyl$(R^q)_3$; heterocyclyl$(R^q)_3$; CN; NH($R^{q'}$); NHC$_{1-6}$alkyl$(R^q)_3$; N($C_{1-6}$alkyl$(R^q)_3)_2$; NHC$_{3-8}$cycloalkyl$(R^q)_3$; N($C_{3-8}$cycloalkyl$(R^q)_3)_2$; $CF_3$; SH; $NO_2$; $C_{2-4}$alkenyl$(R^q)_{2-3}$, aryl$(R^q)_3$, heteroaryl$(R^q)_3$; $C_{2-4}$alkynyl$(R^q)_{1-3}$; —OC(O)$C_{3-8}$cycloalkyl$(R^q)_3$; $SO_2NH_2$; $SO_2NHC_{1-6}$alkyl$(R^q)_3$; $SO_2N(C_{1-6}$alkyl$(R^q)_3)_2$; $NHSO_2C_{1-6}$alkyl$(R^q)_3$, $NHSO_2$aryl$(R^q)_3$, $NHSO_2$ heteroary$(R^q)_3$, —OC(O)heterocyclyl$(R^q)_3$; N($R^{q'}$)C(O)$C_{1-6}$alkyl$(R^q)_3$; $NR^{q'}$C(O)NH($C_{1-6}$alkyl$(R^q)_3$); —OC(O)$C_{1-6}$alkyl$(R^q)_3$; —OC(O)aryl$(R^q)_3$, —OC(O)heteroaryl$(R^q)_3$; —C(=NR$^{q'}$)$NH_2$; —C(=NR$^{q'}$)NHC$_{1-6}$alkyl$(R^q)_3$, —C(=NR$^{q'}$)N($C_{1-6}$alkyl$(R^q)_3)_2$; $CONH_2$; CONHC$_{1-6}$alkyl$(R^q)_3$; CON($C_{1-6}$alkyl$(R^q)_3)_2$; CONHC$_{3-8}$cycloalkyl$(R^q)_3$; CON($C_{3-8}$cycloalkyl$(R^q)_3)_2$; $CO_2H$; $CO_2C_{1-6}$alkyl$(R^q)_3$; C(O)$C_{1-6}$alkyl$(R^q)_3$; $CO_2C_{3-}$ scycloalkyl(R$^q$)$_3$; C(O)C$_{3-8}$cycloalkyl(R$^q$)$_3$; —[C(O)(CH$_2$)$_j$—CR$^5$R$^6$—(CH$_2$)$_k$—NR$^7$]$_{p-R}$$^8$; —C(O)C$_{3-8}$cycloalkyl(R$^q$)$_3$; —C(O)heterocyclyl(R$^q$)$_3$; —CON[C$_{1-6}$alkyl(R$^q$)$_3$][C$_{3-8}$cycloalkyl(R$^q$)$_3$]; —C(O)aryl(R$^q$)$_3$, —C(O)heteroaryl(R$^q$)$_3$;

—O⁺C(O)—(CH$_2$)$_j$—CR$^5$R$^6$—(CH$_2$)$_k$—NR$^7$⁺$_p$R$^8$ and

⁺NR$^7$(CH$_2$)$_k$—CR$^5$R$^6$—(CH$_2$)$_j$—C(O)⁺$_p$OR$^9$ j and k independently represent integers of from 0–3;
R$^5$ and R$^6$ are independently H, aryl, C$_{1-6}$alkyl(R$^q$)$_3$, or CR$^5$R$^6$ in combination represents a 3, 4, 5 or 6 membered cycloalkyl or heterocyclyl group, an aryl group or a heteroaryl group;
p represents 1, 2 or 3, with the proviso that when p represents 1, CR$^5$R$^6$ represents a 3, 4, 5 or 6 membered cycloalkyl group or a heterocyclyl group, an aryl group or a heteroaryl group, and at least one of j and k is 1, 2 or 3;
R$^7$ and R$^8$ are independently H, C$_{1-6}$alkyl or aryl;
R$^9$ represents H, a negative charge balanced by a positively charged group or a protecting group;
R$^q$ represents a member selected from the group consisting of: R$^{q'}$; CN; CO$_2$H; CO$_2$C$_{1-4}$alkyl; C(O)C$_{1-4}$alkyl; NH(R$^{q''}$); aryl(R$^a$)$_3$; heteroaryl(R$^a$)$_3$; NHC$_{1-4}$alkyl; N(C$_{1-4}$alkyl)$_2$; CONH$_2$; SH; S(O)$_y$ C$_{1-6}$alkyl(R$^q$)$_3$; C(O)NHC$_{1-6}$alkyl(R$^q$)$_3$; C(O)N(C$_{1-6}$alkyl(R$^a$)$_3$)$_2$; NHC(NH)NH$_2$; -heteroalkyl(R$^a$)$_3$; —NHC(O)NH$_2$;

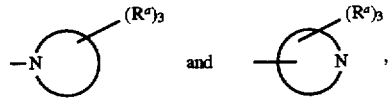

wherein

independently represent mono or bicyclic ring systems, non-aromatic or partially aromatic, containing from 5–10 ring atoms, 1–4 of which are N and 0–1 of which are O or S(O)$_y$, with y equal to 0, 1 or 2, optionally containing 1–2 carbonyl groups;

each R$^a$ independently represents a member selected from the group consisting of: H, C$_{1-6}$alkyl, OC$_{1-6}$alkyl, aralkyl, substituted aralkyl, heteroaralkyl, substituted heteroaralkyl, aralkoxy, substituted aralkoxy, halo, hydroxy, CN, CONH$_2$, CONHC$_{1-6}$alkyl, CON(C$_{1-6}$alkyl)$_2$, CO$_2$H, CO$_2$C$_{1-6}$alkyl, C(O)C$_{1-6}$alkyl, phenyl, CF$_3$, SH, NO$_2$, SO$_y$C$_{1-6}$alkyl, with y as defined above; SO$_2$NH$_2$, SO$_2$NHC$_{1-6}$alkyl, NHSO$_2$(substituted aryl), NHSO$_2$(substituted heteroaryl), NHSO$_2$C$_{1-6}$alkyl, NHSO$_2$aryl, NHSO$_2$ heteroaryl, NH$_2$, NHC$_{1-6}$alkyl, N(C$_{1-6}$alkyl)$_2$, NHC(O)C$_{1-6}$alkyl, NHC(O)NH(C$_{1-6}$alkyl), C$_{2-4}$alkenyl and C$_{2-4}$alkynyl;
R$^{q'}$ represents H, OH, C$_{1-4}$alkyl, —OC$_{1-4}$alkyl, aryl or C(O)C$_{1-4}$alkyl, and
R$^{q''}$ represents H, OH or OC$_{1-4}$alkyl.

2. A compound in accordance with claim 1 wherein one or two R″ are present, each independently representing a member selected from the group consisting of: NH$_2$, NHC$_{1-6}$alkyl(R$^q$)$_3$, N(C$_{1-6}$alkyl)$_2$, N(R$^q$)C(O)C$_{1-6}$alkyl(R$^q$)$_3$ and NR$^q$C(O)NHC$_{1-6}$alkyl(R$^q$)$_3$.

3. A compound in accordance with claim 1 wherein AR represents a phenyl ring unsubstituted or substituted with one or two R groups.

4. A compound in accordance with claim 3 wherein AR is phenyl and one or two R groups are present which are selected from the group consisting of: hydroxyl, halo, C$_{1-6}$alkyl(R$^q$)$_3$, OC$_{1-6}$alkyl(R$^q$)$_3$, NH$_2$, CF$_3$ and NO$_2$.

5. A compound in accordance with claim 4 wherein each R represents halo, hydroxy or CF$_3$.

6. A compound in accordance with claim 1 wherein:
HETCy represents a 5–6 membered non-aromatic heterocycle with 1 nitrogen atom contained therein.

7. A compound in accordance with claim 1 wherein each R' is selected from the group consisting of: C$_{1-6}$alkyl(R$^q$)$_3$, OC$_{1-6}$ alkyl(R$^q$)$_3$, CN and NO$_2$.

8. A compound in accordance with claim 1 wherein R$^q$ is selected from R$^{q'}$, CN, NH(R$^{q''}$)

R$^{q'}$ represents H, C$_{1-4}$alkyl, OH or aryl;
R$^{q''}$ represents H or OH;

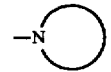

represents a bicyclic partially aromatic group selected from phthalidyl and saccharinyl, and

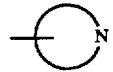

represents piperidinyl.

9. A compound in accordance with claim 1 wherein each R' represents a member selected from the group consisting of: —OC(O)C$_{3-8}$cycloalkyl(R$^q$)$_3$, —OC(O)heterocyclyl(R$^q$)$_3$, N(R$^q$)C(O)C$_{1-6}$alkyl(R$^q$)$_3$, —N(R$^q$)C(O)NH(C$_{1-6}$alkyl(R$^q$)$_3$, —OC(O)C$_{1-6}$alkyl(R$^q$)$_3$, —OC(O)aryl(R$^q$)$_3$, —OC(O)heteroaryl(R$^q$)$_3$, —O[C(O)(CH$_2$)$_j$—CR$^5$R$^6$—(CH$_2$)$_k$—NR$^7$]$_p$R$^8$, and —[NR$^7$—(CH$_2$)$_k$CR$^5$R$^6$—(CH$_2$)$_j$—C(O)]$_p$—OR$^9$.

10. A compound in accordance with claim 9 wherein R$^q$ represents H, C$_{1-4}$alkyl or OC$_{1-4}$alkyl;
R$^{q''}$ represents H or C$_{1-4}$alkyl;
p is 1 or 2; when p is 1, j represents 1 and k represents 0, 1 or 2; when p is 2, j represents 0 or 1, and k represents 0, 1 or 2;
R$^5$ and R$^6$ represent H or C$_{1-6}$alkyl(R$^q$)$_3$ or one of R$^5$ and R$^6$ represents aryl and the other is H or C$_{1-6}$alkyl(R$^q$)$_3$;
R$^7$ and R$^8$ represent H or C$_{1-6}$alkyl(R$^q$)$_3$, and R$^9$ represents H.

11. A compound in accordance with claim 1 wherein each R' represents a member selected from the group consisting of: CONH$_2$; CONHC$_{1-6}$alkyl(R$^q$)$_3$; CON(C$_{1-6}$alkyl(R$^q$)$_3$)$_2$; CONHC$_{3-8}$cycloalkyl(R$^q$)$_3$; CON(C$_{3-8}$cycloalkyl(R$^q$)$_3$)$_2$; CO$_2$H; CO$_2$C$_{1-6}$alkyl(R$^q$)$_3$; C(O)C$_{1-6}$alkyl(R$^q$)$_3$; CO$_2$C$_{3-8}$cycloalkyl(R$^q$)$_3$; C(O)C$_{3-8}$cycloalkyl(R$^q$)$_3$; —[C(O)(CH$_2$)$_j$—CR$^5$R$^6$—(CH$_2$)$_k$—NR$^7$]$_p$—R$^8$; —C(O)C$_{3-8}$cycloalkyl ($R^q$)$_3$; —C(O)heterocyclyl($R^q$)$_3$; CON[C$_{1-6}$alkyl($R^q$)$_3$][C$_{3-8}$cycloalkyl($R^q$)$_3$]; C(O)aryl($R^q$)$_3$ and C(O)heteroaryl($R^q$)$_3$;

p represents 1, 2 or 3, and all other variables are as previously defined.

12. A compound in accordance with claim 1 wherein each R' independently represents a member selected from the group consisting of: CONH$_2$; CONHC$_{1-6}$alkyl($R^q$)$_3$; CON(C$_{1-6}$alkyl($R^q$)$_3$)$_2$; CO$_2$H; CO$_2$C$_{1-6}$alkyl($R^q$)$_3$; C(O)C$_{1-6}$alkyl($R^q$)$_3$; —[C(O)(CH$_2$)$_j$—CR$^5$R$^6$—(CH$_2$)$_k$—NR$^7$]$_p$R$^8$; C(O)aryl($R^q$)$_3$ and C(O)heteroaryl($R^q$)$_3$;

$R^q$ is $R^{q'}$, CN,

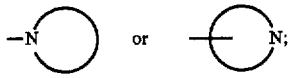

$R^{q'}$ represents H, C$_{1-4}$alkyl, OH or aryl;

represents a bicyclic partially aromatic group selected from phthalidyl and saccharinyl, and

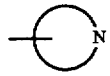

represents piperidinyl.

13. A compound in accordance with claim 12 wherein R' represents a member selected from the group consisting of: CONH$_2$; CO$_2$H; CO$_2$C$_{1-6}$alkyl($R^q$)$_3$; C(O)C$_{1-6}$alkyl($R^q$)$_3$; and —[C(O)(CH$_2$)$_j$—CR$^5$R$^6$—(CH$_2$)$_k$—NR$^7$]$_p$R$^8$;

$R^q$ represents H, C$_{1-4}$alkyl or OC$_{1-4}$alkyl;

p represents 1;

j represents 0 or 1;

k represents 0, 1 or 2; and each R$^7$ and R$^8$ preferably represents H or C$_{1-6}$$_6$alkyl($R^q$)$_3$.

14. A compound in accordance with claim 1 wherein R$^x$ is H or C$_{1-6}$alkyl($R^q$)$_3$.

15. A compound in accordance with claim 1 wherein X' represents a direct bond.

16. A compound in accordance with claim 1 wherein X represents —(CH$_2$)$_m$—Y—(CH$_2$)$_n$—, Y represents a direct bond, O, S or C(O); m represents 0 or 1 and n represents 0 or 1.

17. A compound in accordance with claim 16 wherein X represents a direct bond.

18. A compound in accordance with claim 1 wherein:

AR represents phenyl or naphthyl;

X and X' represent —(CH$_2$)$_m$—Y—(CH$_2$)$_n$—, wherein m and n are zero and Y is a bond;

HETCy represents a pyrrolidinyl or piperidinyl group;

one or two R groups are present and are selected from the group consisting of: halo, hydroxy, C$_{1-6}$alkyl($R^q$)$_3$, OC$_{1-6}$alkyl($R^q$)$_3$, CN, NH$_2$, CO$_2$H, CF$_3$, NO$_2$ and SO$_2$NH$_2$;

one or two R' groups are present and are selected from the group consisting of C$_{1-6}$alkyl($R^q$)$_3$, OC$_{1-6}$alkyl($R^q$)$_3$, CN and NO$_2$;

$R^q$ represents $R^{q'}$, CN, CO$_2$H, NH($R^{q''}$),

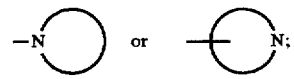

$R^{q'}$ represents H, C$_{1-4}$alkyl, OH or phenyl;

$R^{q''}$ represents H or OH;

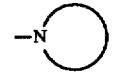

represents phthalidyl or saccharinyl, and

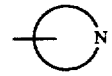

represents piperidinyl.

19. A compound in accordance with claim 1 wherein:

AR represents an aromatic group containing 6–10 atoms;

X and X' each independently represent —(CH$_2$)$_m$—Y—(CH$_2$)$_n$—, wherein m and n represent integers within the range of from 0–4, such that the sum of m and n is from 0–6; Y represents a member selected from the group consisting of: a direct bond; O; S(O)$_y$, with y equal to 0, or 2; NR$^q$, with R$^q$ as defined below; C(O); OC(O); C(O)O; SO$_x$NR$^q$ with x equal to 1 or 2 and R$^q$ as defined below; NR$^q$SO$_x$; C(O)NR$^q$ and NR$^q$C(O);

represents a 4 to 6 membered non-aromatic heterocycle containing only one N atom;

R$^x$ represents H, C$_{1-6}$alkyl($R^q$)$_3$, OC$_{1-6}$alkyl($R^q$)3 or C(O)C$_{1-6}$alkyl($R^q$)$_3$;

each R independently represents a member selected from the group consisting of: halo; hydroxy; C$_{1-6}$alkyl($R^q$)$_3$; OC$_{1-6}$ alkyl($R^q$)$_3$; C$_{3-8}$cycloalkyl($R^q$)$_3$; CN; CONH$_2$; CONHC$_{1-6}$ alkyl($R^q$)$_3$; CON(C$_{1-6}$alkyl($R^q$)$_3$)$_2$; NH$_2$; NHC$_{1-6}$alkyl($R^q$)$_3$; N(C$_{1-6}$alkyl($R^q$)$_3$)$_2$; CO$_2$H; CO$_2$C$_{1-6}$alkyl($R^q$)$_3$; C(O)C$_{1-6}$ alkyl($R^q$)$_3$; aryl($R^q$)$_3$; heteroaryl($R^q$)$_3$; CF$_3$; SH; NO$_2$; NHSO$_2$C$_{1-6}$alkyl($R^q$)$_3$, NHSO$_2$aryl($R^q$)$_3$, NHSO$_2$ heteroary($R^q$)$_3$, N(R$^q$)C(O)C$_{1-6}$alkyl($R^q$)$_3$; NR$^q$C(O)NH(C$_{1-6}$alkyl($R^q$)$_3$); C$_{2-4}$ alkenyl($R^q$)$_{2-3}$ and C$_{2-4}$alkynyl($R^q$)$_{1-3}$;

each R" independently represents a member selected from the group consisting of: halo; hydroxy; C$_{1-6}$alkyl($R^q$)$_3$; OC$_{1-6}$ alkyl($R^q$)$_3$; C$_{3-8}$cycloalkyl($R^q$)$_3$; CN; CONH$_2$; CONHC$_{1-6}$ alkyl($R^q$)$_3$; CON(C$_{1-6}$alkyl($R^q$)$_3$)$_2$; NH$_2$; NHC$_{1-6}$alkyl($R^q$)$_3$; N(C$_{1-6}$alkyl($R^q$)$_3$)$_2$; CO$_2$H; CO$_2$C$_{1-6}$alkyl($R^q$)$_3$; C(O)C$_{1-6}$ alkyl($R^q$)$_3$; aryl($R^q$)$_3$; heteroaryl($R^q$)$_3$; CF$_3$; SH; NO$_2$; SO$_y$C$_{1-6}$ alkyl($R^q$)$_3$, with y as defined above; SO$_2$NH$_2$; SO$_2$NHC$_{1-6}$ alkyl($R^q$)$_3$; SO$_2$N(C$_{1-6}$alkyl($R^q$)$_3$)$_2$; NHSO$_2$C$_{1-6}$alkyl($R^q$)$_3$, NHSO$_2$aryl($R^q$)$_3$, NHSO$_2$ heteroary($R^q$)$_3$, N(R$^q$)C(O)C$_{1-6}$alkyl($R^q$)$_3$; NR$^q$C(O)NH(C$_{1-6}$alkyl($R^q$)$_3$); C$_{2-4}$alkenyl($R^q$)$_{2-3}$ and C$_{2-4}$ alkynyl($R^q$)$_{1-3}$;

each R' independently represents a member selected from the group of: hydroxy; C$_{1-6}$alkyl($R^q$)$_3$; C$_{3-8}$ cycloalkyl(R$^q$)$_3$; OC$_{1-6}$alkyl(R$^q$)$_3$; OC$_{3-8}$cycloalkyl(R$^q$)$_3$; heterocyclyl(R$^q$)$_3$; CN; NH(R$^{q''}$); NHC$_{1-6}$alkyl(R$^q$)$_3$; N(C$_{1-6}$ alkyl(R$^q$)$_3$)$_2$; NHC$_{3-8}$cycloalkyl(R$^q$)$_3$; N(C$_{3-8}$cycloalkyl(R$^q$)$_3$)$_2$; CF$_3$; SH; NO$_2$; C$_{2-4}$alkenyl (R$^q$)$_{2-3}$, aryl(R$^q$)$_3$, heteroaryl(R$^q$)$_3$; C$_{2-4}$alkynyl(R$^q$)$_{1-3}$; —OC(O)C$_{3-8}$cycloalkyl(R$^q$)$_3$; SO$_2$NH$_2$; SO$_2$NHC$_{1-6}$alkyl(R$^q$)$_3$; SO$_2$N(C$_{1-6}$alkyl(R$^q$)$_3$)$_2$; NHSO$_2$C$_{1-6}$alkyl(R$^q$)$_3$, NHSO$_2$aryl(R$^q$)$_3$, NHSO$_2$ heteroary(R$^q$)$_3$, —OC(O)heterocyclyl(R$^q$)$_3$; N(R$^{q'}$)C(O)C$_{1-6}$alkyl(R$^q$)$_3$; NR$^{q'}$C(O)NH(C$_{1-6}$alkyl(R$^q$)$_3$); —OC(O)C$_{1-6}$alkyl(R$^q$)$_3$; —OC(O)aryl(R$^q$)$_3$, —OC(O)heteroaryl(R$^q$)$_3$; —C(=NR$^{q'}$)NH$_2$; —C(=N$^{q'}$)NHC$_{1-6}$alkyl(R$^q$)$_3$, —C(=N$^{q'}$)N(C$_{1-6}$alkyl(R$^q$)$_3$)$_2$; CONH$_2$; CONHC$_{1-6}$alkyl(R$^q$)$_3$; CON(C$_{1-6}$alkyl(R$^q$)$_3$)$_2$; CONHC$_{3-8}$cycloalkyl(R$^q$)$_3$; CON(C$_{3-8}$cycloalkyl(R$^q$)$_3$)$_2$; CO$_2$H; CO$_2$C$_{1-6}$ alkyl(R$^q$)$_3$; C(O)C$_{1-6}$alkyl(R$^q$)$_3$; CO$_2$C$_{3-8}$cycloalkyl(R$^q$)$_3$; C(O)C$_{3-8}$cycloalkyl(R$^q$)$_3$; —[C(O)(CH$_2$)$_j$—CR$^5$R$^6$—(CH$_2$)$_k$—NR$^7$]$_p$—R$^8$; —C(O)C$_{3-8}$cycloalkyl(R$^q$)$_3$; —C(O)heterocyclyl(R$^q$)$_3$; CON[C$_{1-6}$alkyl(R$^q$)$_3$][C$_{3-8}$cycloalkyl(R$^q$)$_3$]; C(O)aryl(R$^q$)$_3$, C(O)heteroaryl(R$^q$)$_3$;

—O⫻C(O)—(CH$_2$)$_j$—CR$^5$R$^6$—(CH$_2$)$_k$—NR$^7$⫻$_p$R$^8$ and

⫻NR$^7$(CH$_2$)$_k$—CR$^5$R$^6$—(CH$_2$)$_j$—C(O)⫻$_p$OR$^9$ j and k independently represent integers of from 0–3;
R$^5$ and R$^6$ are independently H, aryl, C$_{1-6}$alkyl(R$^q$)$_3$, or CR$^5$R$^6$ in combination represents a 3, 4, 5 or 6 membered cycloalkyl or heterocyclyl group, an aryl group or a heteroaryl group;
p represents 1, 2 or 3, with the proviso that when p represents 1, CR$^5$R$^6$ represents a 3, 4, 5 or 6 membered cycloalkyl group or a heterocyclyl group, an aryl group or a heteroaryl group, and at least one of j and k is 1, 2 or 3;
R$^7$ and R$^8$ are independently H, C$_{1-6}$alkyl or aryl;
R9 represents H, a negative charge balanced by a positively charged group or a protecting group;
R$^q$ represents a member selected from the group consisting of: R$^{q'}$; CN; CO$_2$H; CO$_2$C$_{1-4}$alkyl; C(O)C$_{1-4}$alkyl; NH(R$^{q''}$); aryl(R$^q$)$_3$; heteroaryl(R$^q$)$_3$; NHC$_{1-4}$alkyl; N(C$_{1-4}$alkyl)$_2$; CONH$_2$; SH;S(O)$_y$C$_{1-6}$alkyl(R$^q$)$_3$; C(O)NHC$_{1-6}$alkyl(R$^q$)$_3$; C(O)N(C$_{1-6}$alkyl(R$^q$)$_3$)$_2$; NHC(NH)NH$_2$; -heteroalkyl(R$^a$)$_3$; —NHC(O)NH$_2$;

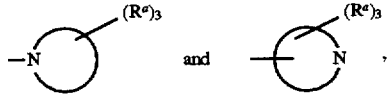

wherein

independently represent mono or bicyclic ring systems, non-aromatic or partially aromatic, containing from 5–10 ring atoms, 1–4 of which are N and 0–1 of which are O or S(O)$_y$, with y equal to 0, 1 or 2, optionally containing 1–2 carbonyl groups;

each R$^a$ independently represents a member selected from the group consisting of: H, C$_{1-6}$alkyl, OC$_{1-6}$alkyl, aralkyl, substituted aralkyl, heteroaralkyl, substituted heteroaralkyl, aralkoxy, substituted aralkoxy, halo, hydroxy, CN, CONH$_2$, CONHC$_{1-6}$alkyl, CON(C$_{1-6}$alkyl)$_2$, CO$_2$H, CO$_2$C$_{1-6}$alkyl, C(O)C$_{1-6}$alkyl, phenyl, CF$_3$, SH, NO$_2$, SO$_y$C$_{1-6}$alkyl, with y as defined above; SO$_2$NH$_2$, SO$_2$NHC$_{1-6}$ alkyl, NHSO$_2$(substituted aryl), NHSO$_2$(substituted heteroaryl), NHSO$_2$C$_{1-6}$alkyl, NHSO$_2$aryl, NHSO$_2$ heteroaryl, NH$_2$, NHC$_{1-6}$alkyl, N(C$_{1-6}$alkyl)$_2$, NHC(O)C$_{1-6}$alkyl, NHC(O)NH(C$_{1-6}$alkyl), C$_{2-4}$ alkenyl and C$_{2-4}$alkynyl;

R$^{q'}$ represents H, OH, C$_{1-4}$alkyl, —OC$_{1-4}$alkyl, aryl or C(O)C$_{1-4}$alkyl, and R$^{q''}$ represents H, OH or OC$_{1-4}$alkyl.

20. A compound in accordance with claim 19 wherein X represents a bond.

21. A compound represented by formula Ia:

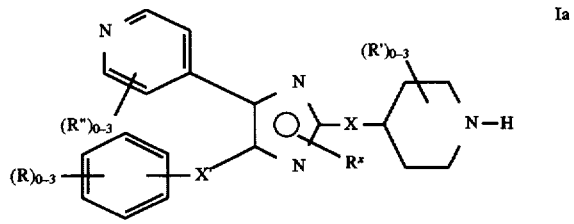

or a pharmaceutically acceptable salt thereof, wherein:

X and X' each independently represent —(CH$_2$)$_m$—Y—(CH$_2$)$_n$—, wherein m and n represent integers within the range of from 0–4, such that the sum of m and n is from 0–6; Y represents a member selected from the group consisting of: a direct bond; O; S(O)$_y$, with y equal to 0, 1 or 2; NR$^{q'}$, with R$^{q'}$ as defined below; C(O); OC(O); C(O)O; SO$_x$NR$^{q'}$ with x equal to 1 or 2 and R$^{q'}$ as defined below; NR$^{q'}$SO$_x$; C(O)NR$^{q'}$ and NR$^{q'}$C(O);

R$^x$ represents H, C$_{1-6}$alkyl(R$^q$)$_3$ or OC$_{1-6}$alkyl(R$^q$)$_3$;

each R independently represents a member selected from the group consisting of: halo; hydroxy; C$_{1-6}$alkyl(R$^q$)$_3$; OC$_{1-6}$ alkyl(R$^q$)$_3$; C$_{3-8}$cycloalkyl(R$^q$)$_3$; CN; CONH$_2$; CONHC$_{1-6}$ alkyl(R$^q$)$_3$; CON(C$_{1-6}$alkyl(R$^q$)$_3$)$_2$; NH$_2$; NHC$_{1-6}$alkyl(R$^q$)$_3$; N(C$_{1-6}$alkyl(R$^q$)$_3$)$_2$; CO$_2$H; CO$_2$C$_{1-6}$alkyl(R$^q$)$_3$; C(O)C$_{1-6}$ alkyl(R$^q$)$_3$; aryl(R$^q$)$_3$; heteroaryl (R$^q$)$_3$; CF$_3$; SH; NO$_2$; NHSO$_2$C$_{1-6}$alkyl(R$^q$)$_3$, NHSO$_2$aryl(R$^q$)$_3$, NHSO$_2$ heteroary(R$^q$)$_3$, N(R$^{q'}$)C(O)C$_{1-6}$alkyl(R$^q$)$_3$; NR$^{q'}$C(O)NH(C$_{1-6}$alkyl(R$^q$)$_3$); C$_{2-4}$ alkenyl(R$^q$)$_{2-3}$ and C$_{2-4}$alkynyl(R$^q$)$_{1-3}$;

each R" independently represents a member selected from the group consisting of: halo; hydroxy; C$_{1-6}$alkyl(R$^q$)$_3$; OC$_{1-6}$ alkyl(R$^q$)$_3$; C$_{3-8}$cycloalkyl(R$^q$)$_3$; CN; CONH$_2$; CONHC$_{1-6}$ alkyl(R$^q$)$_3$; CON(C$_{1-6}$alkyl(R$^q$)$_3$)$_2$; NH$_2$; NHC$_{1-6}$alkyl(R$^q$)$_3$; N(C$_{1-6}$alkyl(R$^q$)$_3$)$_2$; CO$_2$H; CO$_2$C$_{1-6}$alkyl(R$^q$)$_3$; C(O)C$_{1-6}$ alkyl(R$^q$)$_3$; aryl(R$^q$)$_3$; heteroaryl (R$^q$)$_3$; CF$_3$; SO$_y$C$_{1-6}$alkyl(R$^q$)$_3$, with y as defined above; SO$_2$NH$_2$; SO$_2$NHC$_{1-6}$alkyl(R$^q$)$_3$; SO$_2$N(C$_{1-6}$alkyl(R$^q$)$_3$)$_2$; NHSO$_2$C$_{1-6}$alkyl(R$^q$)$_3$, NHSO$_2$aryl(R$^q$)$_3$, NHSO$_2$ heteroary(R$^q$)$_3$, N(R$^{q'}$)C(O)C$_{1-6}$alkyl(R$^q$)$_3$; NR$^{q'}$C(O)NH(C$_{1-6}$alkyl(R$^q$)$_3$); C$_{2-4}$alkenyl(R$^q$)$_{2-3}$ and C$_{2-4}$ alkynyl(R$^q$)$_{1-3}$;

each R' independently represents a member selected from the group consisting of: hydroxy; C$_{1-6}$alkyl(R$^q$)$_3$; C$_{3-8}$cycloalkyl(R$^q$)$_3$; OC$_{1-6}$alkyl(R$^q$)$_3$; OC$_{3-8}$cycloalkyl(R$^q$)$_3$; heterocyclyl(R$^q$)$_3$; CN; NH(R$^{q''}$); NHC$_{1-6}$alkyl(R$^q$)$_3$; N(C$_{1-6}$ alkyl(R$^q$)$_3$)$_2$; NHC$_{3-8}$cycloalkyl(R$^q$)$_3$;

$N(C_{3-8}cycloalkyl(R^q)_3)_2$; $CF_3$; $C_{2-4}alkenyl(R^q)_{2-3}$, aryl $(R^q)_3$, heteroaryl$(R^q)_3$; $C_{2-4}$ alkynyl$(R^q)_{1-3}$; —OC(O) $C_{3-8}cycloalkyl(R^q)_3$; $SO_2NH_2$; $SO_2NHC_{1-6}alkyl(R^q)_3$; $SO_2N(C_{1-6}alkyl(R^q)_3)_2$; —OC(O)heterocyclyl$(R^q)_3$; $CONH_2$; $CONHC_{1-6}alkyl(R^q)_3$; $CON(C_{1-6}alkyl(R^q)_3)_2$; $CONHC_{3-8}cycloalkyl(R^q)_3$; $CON(C_{3-8}$ cycloalkyl $(R^q)_3)_2$; $C(O)aryl(R^q)_3$, $C(O)heteroaryl(R^q)_3$;

$R^q$ represents a member selected from the group consisting of: $R^{q'}$; CN; $CO_2H$; $CO_2C_{1-4}alkyl$; $C(O)C_{1-4}alkyl$; $NH(R^{q''})$; aryl$(R^a)_3$; heteroaryl$(R^a)_3$; $NHC_{1-4}alkyl$; $N(C_{1-4}alkyl)_2$; $CONH_2$; SH; $S(O)_y$ $C_{1-6}alkyl(R^a)_3$; $C(O)NHC_{1-6}alkyl(R^a)_3$; $C(O)N(C_{1-6}alkyl(R^a)_3)_2$; $NHC(NH)NH_2$; -heteroalkyl$(R^a)_3$; —NHC(O)NH_2;

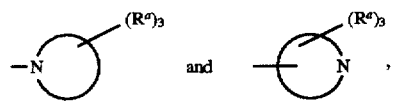

wherein

independently represent mono or bicyclic ring systems, non-aromatic or partially aromatic, containing from 5–10 ring atoms, 1–4 of which are N and 0–1 of which are O or $S(O)_y$, with y equal to 0, 1 or 2, optionally containing 1–2 carbonyl groups;

each $R^a$ independently represents a member selected from the group consisting of: H, $C_{1-6}alkyl$, $OC_{1-6}alkyl$, aralkyl, substituted aralkyl, heteroaralkyl, substituted heteroaralkyl, aralkoxy, substituted aralkoxy, halo, hydroxy, CN, $CONH_2$, $CONHC_{1-6}alkyl$, $CON(C_{1-6}$ alkyl$)_2$, $CO_2H$, $CO_2C_{1-6}alkyl$, $C(O)C_{1-6}alkyl$, phenyl, $CF_3$, SH, $NO_2$, $SO_yC_{1-6}alkyl$, with y as defined above; $SO_2NH_2$, $SO_2NHC_{1-6}$ alkyl, $NHSO_2$(substituted aryl), $NHSO_2$(substituted heteroaryl), $NHSO_2C_{1-6}alkyl$, $NHSO_2aryl$, $NHSO_2$ heteroaryl, $NH_2$, $NHC_{1-6}alkyl$, $N(C_{1-6}alkyl)_2$, $NHC(O)C_{1-6}alkyl$, $NHC(O)NH(C_{1-6}alkyl)$, $C_{2-4}$ alkenyl and $C_{2-4}alkynyl$;

$R^{q'}$ represents H, OH, $C_{1-4}alkyl$, —$OC_{1-4}alkyl$, aryl or $C(O)C_{1-4}alkyl$, and $R^{q''}$ represents H, OH or $OC_{1-4}alkyl$.

22. A compound represented by formula Ib:

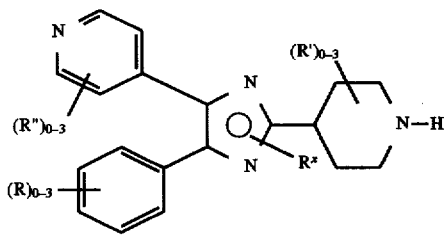

or a pharmaceutically acceptable salt thereof, wherein:

$R^x$ represents H, $C_{1-6}alkyl(R^q)_3$ or $OC_{1-6}alkyl(R^q)_3$;

each R independently represents a member selected from the group consisting of: halo; hydroxy; $C_{1-6}alkyl(R^q)_3$; $OC_{1-6}$ alkyl$(R^q)_3$; $C_{3-8}cycloalkyl(R^q)_3$; CN; $CONH_2$; $CONHC_{1-6}$ alkyl$(R^q)_3$; $CON(C_{1-6}alkyl(R^q)_3)_2$; $NH_2$; $NHC_{1-6}alkyl(R^q)_3$; $N(C_{1-6}alkyl(R^q)_3)_2$; $CO_2H$; $CO_2C_{1-6}alkyl(R^q)_3$; $C(O)C_{1-6}$ alkyl$(R^q)_3$; aryl$(R^q)_3$; heteroaryl $(R^q)_3$; $CF_3$; SH; $NO_2$; $NHSO_2C_{1-6}alkyl(R^q)_3$, $NHSO_2aryl(R^q)_3$, $NHSO_2$ heteroary$(R^q)_3$, $N(R^{q'})C(O)C_{1-6}alkyl(R^q)_3$; $NR^qC(O)NH(C_{1-6}alkyl(R^q)_3)$; $C_{2-4}$ alkenyl$(R^q)_{2-3}$ and $C_{2-4}alkynyl(R^q)_3$;

each R'' independently represents a member selected from the group consisting of: halo; hydroxy; $C_{1-6}alkyl(R^q)_3$; $OC_{1-6}$ alkyl$(R^q)_3$; $C_{3-8}cycloalkyl(R^q)_3$; CN; $CONH_2$; $CONHC_{1-6}$ alkyl$(R^q)_3$; $CON(C_{1-6}alkyl(R^q)_3)_2$; $NH_2$; $NHC_{1-6}alkyl(R^q)_3$; $N(C_{1-6}alkyl(R^q)_3)_2$; $CO_2H$; $CO_2C_{1-6}alkyl(R^q)_3$; $C(O)C_{1-6}$ alkyl$(R^q)_3$; aryl$(R^q)_3$; heteroaryl $(R^q)_3$; $CF_3$; $SO_yC_{1-6}alkyl(R^q)_3$, with y as defined above; $SO_2NH_2$; $SO_2NHC_{1-6}alkyl(R^q)_3$; $SO_2N(C_{1-6}alkyl(R^q)_3)_2$; $NHSO_2C_{1-6}alkyl(R^q)_3$, $NHSO_2aryl(R^q)_3$, $NHSO_2$ heteroary$(R^q)_3$, $N(R^q)C(O)C_{1-6}alkyl(R^q)_3$; $NR^qC(O)NH(C_{1-6}alkyl(R^q)_3)$; $C_{2-4}alkenyl(R^q)_{2-3}$ and $C_{2-4}$ alkynyl$(R^q)_{1-3}$;

each R' independently represents a member selected from the group consisting of: hydroxy; $C_{1-6}alkyl(R^q)_3$; $C_{3-8}$ cycloalkyl$(R^q)_3$; $OC_{1-6}alkyl(R^q)_3$; $OC_{3-8}cycloalkyl(R^q)_3$; heterocyclyl$(R^q)_3$; CN; $NH(R^{q''})$; $NHC_{1-6}alkyl(R^q)_3$; $N(C_{1-6}$ alkyl$(R^q)_3)_2$; $NHC_{3-8}cycloalkyl(R^q)_3$; $N(C_{3-8}cycloalkyl(R^q)_3)_2$; $CF_3$; $C_{2-4}alkenyl(R^q)_{2-3}$, aryl $(R^q)_3$, heteroaryl$(R^q)_3$; $C_{2-4}$ alkynyl$(R^q)_{1-3}$; —OC(O) $C_{3-8}cycloalkyl(R^q)_3$; $SO_2NH_2$; $SO_2NHC_{1-6}alkyl(R^q)_3$; $SO_2N(C_{1-6}alkyl(R^q)_3)_2$; —OC(O)heterocyclyl$(R^q)_3$; $CONH_2$; $CONHC_{1-6}alkyl(R^q)_3$; $CON(C_{1-6}alkyl(R^q)_3)_2$; $CONHC_{3-8}cycloalkyl(R^q)_3$; $CON(C_{3-8}$ cycloalkyl $(R^q)_3)_2$; $C(O)aryl(R^q)_3$, $C(O)heteroaryl(R^q)_3$;

$R^q$ represents a member selected from the group consisting of: $R^{q'}$; CN; $CO_2H$; $CO_2C_{1-4}alkyl$; $C(O)C_{1-4}alkyl$; $NH(R^{q''})$;aryl$(R^a)_3$; heteroaryl$(R^a)_3$; $NHC_{1-4}alkyl$; $N(C_{1-4}alkyl)_2$; $CONH_2$; SH; $S(O)_y$ $C_{1-6}alkyl(R^a)_3$; $C(O)NHC_{1-6}alkyl(R^a)_3$; $C(O)N(C_{1-6}alkyl(R^a)_3)_2$; $NHC(NH)NH_2$; -heteroalkyl$(R^a)_3$; —NHC(O)NH_2;

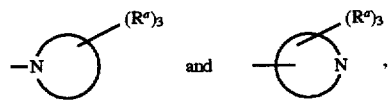

wherein

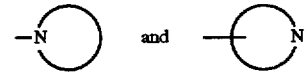

independently represent mono or bicyclic ring systems, non-aromatic or partially aromatic, containing from 5–10 ring atoms, 1–4 of which are N and 0–1 of which are O or $S(O)_y$, with y equal to 0, 1 or 2, optionally containing 1–2 carbonyl groups;

each $R^a$ independently represents a member selected from the group consisting of: H, $C_{1-6}alkyl$, $OC_{1-6}alkyl$, aralkyl, substituted aralkyl, heteroaralkyl, substituted heteroaralkyl, aralkoxy, substituted aralkoxy, halo, hydroxy, CN, $CONH_2$, $CONHC_{1-6}alkyl$, $CON(C_{1-6}$ alkyl$)_2$, $CO_2H$, $CO_2C_{1-6}alkyl$, $C(O)C_{1-6}alkyl$, phenyl, $CF_3$, SH, $NO_2$, $SO_yC_{1-6}alkyl$, with y as defined above; $SO_2NH_2$, $SO_2NHC_{1-6}$ alkyl, $NHSO_2$(substituted aryl), $NHSO_2$(substituted heteroaryl), $NHSO_2C_{1-6}alkyl$, $NHSO_2aryl$, $NHSO_2$ heteroaryl, $NH_2$, $NHC_{1-6}alkyl$, $N(C_{1-6}alkyl)_2$, $NHC(O)C_{1-6}alkyl$, $NHC(O)NH(C_{1-6}alkyl)$, $C_{2-4}$ alkenyl and $C_{2-4}alkynyl$;

$R^{q'}$ represents H, OH, $C_{1-4}alkyl$, —$OC_{1-4}alkyl$, aryl or $C(O)C_{1-4}alkyl$, and $R^{q''}$ represents H, OH or $OC_{1-4}alkyl$.

23. A compound in accordance with claim 1 selected from the group consisting of:
4-[5-(4-fluorophenyl)-4-pyridin-4-yl-1H-imidazol-2-yl]-piperidine-1-carboxylic acid tert-butyl ester;
4-benzyl-[4-(4-fluorophenyl)-5-pyridin-4-yl-1H-imidazol-2-yl]-piperidine-1-carboxylic acid tert-butyl ester;
3-[5-(4-fluorophenyl)-4-pyridin-4-yl-1H-imidazol-2-yl]-piperidine-1-carboxylic acid tert-butyl ester;
4-[5-(4-fluorophenyl)-4-pyridin-4-yl-1H-imidazol-2-yl]-1-acetylpiperidine;
4-[5-(4-fluorophenyl)-4-pyridin-4-yl-1H-imidazol-2-yl]-piperidine;
4-[5-(4-fluorophenyl)-4-pyridin-4-yl-1H-imidazol-2-yl]-1-methyl-piperidine;
4-[5-(4-fluorophenyl)-4-pyridin-4-yl-1H-imidazol-2-yl]-1-benzyl-piperidine;
4-[5-(4-fluorophenyl)-4-pyridin-4-yl-1H-imidazol-2-yl]-1-ethyl-piperidine;
4-[5-(3,4-dichlorophenyl)-4-pyridin-4-yl-1H-imidazol-2-yl]-piperidine;
4-[5-(3,4-dichlorophenyl)-4-pyridin-4-yl-1H-imidazol-2-yl]-1-methyl-piperidine;
2-(4-{4-[5-(3,4-dichlorophenyl)-4-pyridin-4-yl-1H-imidazol-2-yl]-piperidin-1-yl}-butyl)-isoindole-1,3-dione;
2-(5-{4-[5-(3,4-dichlorophenyl)-4-pyridin-4-yl-1H-imidazol-2-yl]-piperidin-1-yl}-pentyl)-isoindole-1,3-dione;
2-(6-{4-[5-(3,4-dichlorophenyl)-4-pyridin-4-yl-1H-imidazol-2-yl]-piperidin-1-yl}-hexyl)-isoindole-1,3-dione;
4-[5-(3,4-dichlorophenyl)-4-pyridin-4-yl-1H-imidazol-2-yl]-1-benzyl-piperidine;
2-(5-{4-[5-(3,4-dichlorophenyl)-4-pyridin-4-yl-1H-imidazol-2-yl]-piperidin-1-yl}-pentyl)-2,3-dihydro-isoindol-1-one;
4-(4-{4-[5-(3,4-dichlorophenyl)-4-pyridin-4-yl-1H-imidazol-2-yl]-piperidin-1-yl}-ethyl)-pyridine;
2-(5-{4-[5-(3,4-dichlorophenyl)-4-pyridin-4-yl-1H-imidazol-2-yl]-piperidin-1-yl}-pentyl)-1,1-dioxobenzo[d]isothiazol-3-one;
2-(4-{4-[5-(3,4-dichlorophenyl)-4-pyridin-4-yl-1H-imidazol-2-yl]-piperidin-1-yl}-butyl)-1,1-dioxobenzo[d]isothiazol-3-one;
4-[5-(3-hydroxyphenyl)-4-pyridin-4-yl-1H-imidazol-2-yl]-1-methyl-piperidine;
3-[5-(4-fluorophenyl)-4-pyridin-4-yl-1H-imidazol-2-yl]-piperidine;
3-[5-(4-fluorophenyl)-4-pyridin-4-yl-1H-imidazol-2-yl]-1-methyl-piperidine;
4-[5-(4-fluorophenyl)-4-pyridin-4-yl-1H-imidazol-2-yl]-1,4-dimethyl-piperidine;
4-benzyl-[4-(4-fluorophenyl)-5-pyridin-4-yl-1H-imidazol-2-yl]-piperidine-1-carboxylic acid tert-butyl ester;
4-benzyl-[4-(4-fluorophenyl)-5-pyridin-4-yl-1H-imidazol-2-yl]-piperidine;
2-amino-1-{5-[4-(3,4-dichlorophenyl)-4-pyridin-4-yl-1H-imidazol-2-yl]-piperidin-1-yl}-ethanone;
4-{5-(3,4-dichlorophenyl)-2-[1-(2-phenylethyl)-piperidin-4-yl]-1H-imidazol-4-yl}-pyridine;
4-{5-(3,4-dichlorophenyl)-2-[1-(3-phenylpropyl)-piperidin-4-yl]-1H-imidazol-4-yl}-pyridine;
2-(6-{4-[5-(3,4-dichlorophenyl)-4-pyridin-4-yl-1H-imidazol-2-yl]-piperidin-1-yl}-hexyl)-1,1-dioxobenzo[d]isothiazol-3-one;
2-(3-{4-[5-(3,4-dichlorophenyl)-4-pyridin-4-yl-1H-imidazol-2-yl]-piperidin-1-yl}-propyl)-1,1-dioxobenzo[d]isothiazol-3-one;
4-(5-{4-[5-(3,4-dichlorophenyl)-4-pyridin-4-yl-1H-imidazol-2-yl]-piperidin-1-yl-methyl}-imidazol-1-yl-methyl)-benzonitrile;
4-[2-[1-(4-benzyloxybenzyl)-piperidin-4-yl-5-(3,4-dichlorophenyl)-1H-imidazol-4-yl-pyridine;
4-[4-fluorophenyl)-3-pyridin-yl-1H-imidazol-2-yl]-1-acetyl-piperidine;
3-[4-fluorophenyl)-3-pyridin-yl-1H-imidazol-2-yl]-1-acetyl-piperidine; and
2-(3-{4-[5-(3,4-dichlorophenyl)-4-pyridin-4-yl-1H-imidazol-2-yl]-piperidin-1-yl}-propyl)-isoindole-1,3-dione,
or a pharmaceutically acceptable salt thereof.

24. A compound in accordance with claim 1 selected from the following table:

| No. | Compound |
|---|---|
| 1 | |
| 2 | |

-continued
| No. | Compound |
|---|---|
| 3 | 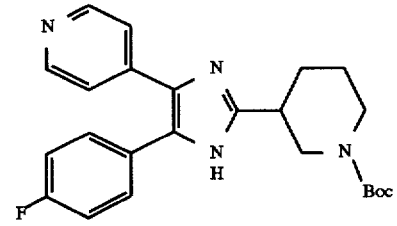 |
| 4 | 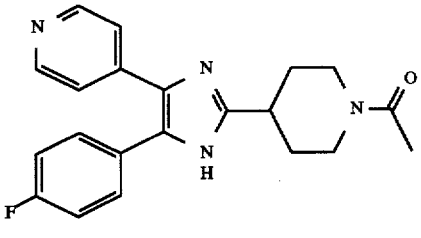 |
| 5 | 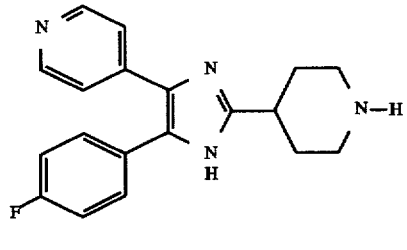 |
| 6 | 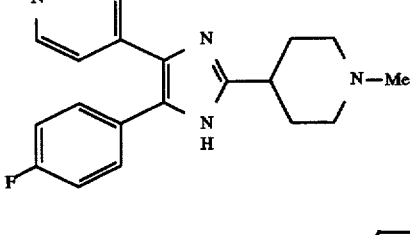 |
| 7 | 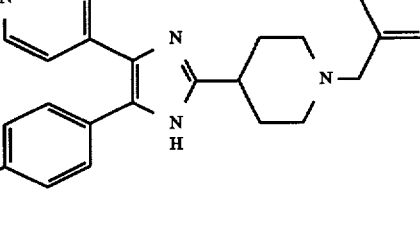 |
| 8 | 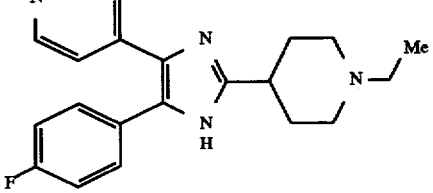 |

-continued

| No. | Compound |
|---|---|
| 9 | 4-(4-pyridyl)-5-(3,4-dichlorophenyl)-2-(4-piperidyl)-1H-imidazole |
| 10 | 4-(4-pyridyl)-5-(3,4-dichlorophenyl)-2-(1-methyl-4-piperidyl)-1H-imidazole |
| 11 | 4-(4-pyridyl)-5-(3,4-dichlorophenyl)-2-[1-(4-phthalimidobutyl)-4-piperidyl]-1H-imidazole |
| 12 | 4-(4-pyridyl)-5-(3,4-dichlorophenyl)-2-[1-(5-phthalimidopentyl)-4-piperidyl]-1H-imidazole |
| 13 | 4-(4-pyridyl)-5-(3,4-dichlorophenyl)-2-[1-(6-phthalimidohexyl)-4-piperidyl]-1H-imidazole |

| No. | Compound |
|---|---|
| 14 | [structure: 4-(4-pyridyl)-5-(3,4-dichlorophenyl)-2-(1-benzylpiperidin-4-yl)-1H-imidazole] |
| 15 | [structure: 4-(4-pyridyl)-5-(3,4-dichlorophenyl)-2-{1-[5-(2-benzoylisoindolin-N-yl)pentyl]piperidin-4-yl}-1H-imidazole] |
| 16 | [structure: 4-(4-pyridyl)-5-(3,4-dichlorophenyl)-2-{1-[2-(4-pyridyl)ethyl]piperidin-4-yl}-1H-imidazole] |
| 17 | [structure: 4-(4-pyridyl)-5-(3,4-dichlorophenyl)-2-{1-[4-(2-benzoylsulfonamido)butyl]piperidin-4-yl}-1H-imidazole, with N—SO$_2$ linkage] |

-continued

| No. | Compound |
|---|---|
| 18 | (4-pyridyl)(3,4-dichlorophenyl)imidazole-2-yl piperidine N-(4-(N-(2-sulfonylbenzoyl))butyl) |
| 19 | 4-(4-pyridyl)-5-(3-hydroxyphenyl)-2-(1-methyl-4-piperidyl)imidazole |
| 20 | 4-(4-pyridyl)-5-(4-fluorophenyl)-2-(3-piperidyl)imidazole |
| 21 | 4-(4-pyridyl)-5-(4-fluorophenyl)-2-(1-methyl-3-piperidyl)imidazole |
| 22 | 4-(4-pyridyl)-5-(4-fluorophenyl)-2-(1,4-dimethyl-4-piperidyl)imidazole |
| 23 | 4-(4-pyridyl)-5-(4-fluorophenyl)-2-(4-benzyl-4-piperidyl)imidazole |

-continued

| No. | Compound |
|---|---|
| 24 | (structure) |
| 25 | (structure) |
| 26 | (structure) |
| 27 | (structure) |
| 28 | (structure) | or a pharmaceutically acceptable salt thereof.

25. A compound in accordance with claim 1 selected from the group consisting of:

4-[5-(3,4-dichlorophenyl)-4-pyridin-4-yl-1H-imidazol-2-yl] piperidine-1-carboxylic acid benzyl ester;

4-[5-(3-methoxyphenyl)-4-pyridin-4-yl-1H-imidazol-2-yl] piperidine-1-carboxylic acid tert-butyl ester;

4-[5-(4-fluorophenyl)-4-pyridin-4-yl-1H-imidazol-2-yl]-4-methylpiperidine-1-carboxylic acid tert-butyl ester;

4-[1-propyl-5-pyridin-4-yl-4-(3-trifluoromethylphenyl)-1H-imidazol-2-yl]piperidine-1-carboxylic acid benzyl ester;

4-[1-hydroxy-5-(2-fluoropyridin-4-yl)-4-(3-trifluoromethylphenyl)-1H-imidazol-2-yl]piperidine-1-carboxylic acid benzyl ester;

4-[5-(2-fluoropyridin-4-yl)-4-(3-trifluoromethylphenyl)-1H-imidazol-2-yl]piperidine-1-carboxylic acid benzyl ester;

4-[5-(2-fluoropyridin-4-yl)-1-methyl-4-(3-trifluoromethylphenyl)-1H-imidazol-2-yl]-piperidine-1-carboxylic acid benzyl ester and (S)-4-[5-(2-(1-Phenylethylamino)pyridin-4-yl)-1-methyl-4-(3-trifluoromethylphenyl)-1H-imidazol-2-yl]-piperidine-1-carboxylic acid benzyl ester.

26. A pharmaceutical composition which is comprised of a compound in accordance with claim 1 in combination with a pharmaceutically acceptable carrier.

27. A pharmaceutical composition which is produced by combining a compound in accordance with claim 1 and a pharmaceutically acceptable carrier.

28. A method of treating cancers that respond to inhibition to RAF kinase which comprises administering to a mammalian patient in need of such treatment a compound in accordance with claim 1 in an amount which is effective to treat said cancers.

29. A method of treating a cytokine mediated disease in a mammal, comprising administering to a mammalian patient in need of such treatment an amount of a compound as described in claim 1 in an amount which is effective to treat said cytokine mediated disease.

30. A method of treating inflammation in a mammalian patient in need of such treatment, which is comprised of administering to said patient an anti-inflammatory effective amount of a compound as described in claim 1.

31. A method of treating osteoporosis in a mammalian patient in need of such treatment, which is comprised of administering to said patient an amount of a compound as described in claim 1 which is effective to treat osteoporosis.

32. A method of treating bone resorption in a mammalian patient in need of such treatment, which is comprised of administering to said patient an amount of a compound as described in claim 1 which is effective to treat bone resorption.

33. A method of treating Crohn's disease in a mammalian patient in need of such treatment which is comprised of administering to said patient an amount of a compound as described in claim 1 which is effective to treat Crohn's disease.

* * * * *